United States Patent
DelMonte et al.

(10) Patent No.: US 7,381,737 B2
(45) Date of Patent: Jun. 3, 2008

(54) CRYSTALLINE FORMS AND PROCESS FOR PREPARING SPIRO-HYDANTOIN COMPOUNDS

(75) Inventors: Albert J. DelMonte, Edison, NJ (US); T. G. Murali Dhar, Newtown, PA (US); Yu Fan, Highland Park, NJ (US); Jack Z. Gougoutas, Princeton, NJ (US); Mary F. Malley, Lawrenceville, NJ (US); Douglas D. McLeod, Kingston, NJ (US); Robert E. Waltermire, Hillsborough, NJ (US); Chenkou Wei, Princeton Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 146 days.

(21) Appl. No.: 11/238,427

(22) Filed: Sep. 29, 2005

(65) Prior Publication Data
US 2006/0074099 A1   Apr. 6, 2006

Related U.S. Application Data

(60) Provisional application No. 60/615,292, filed on Oct. 1, 2004, provisional application No. 60/617,905, filed on Oct. 12, 2004, provisional application No. 60/717,290, filed on Sep. 15, 2005.

(51) Int. Cl.
*A61K 31/4188* (2006.01)
*C07D 235/00* (2006.01)
(52) U.S. Cl. .................... 514/389; 548/301.4
(58) Field of Classification Search ............ 548/301.4; 514/389
See application file for complete search history.

(56) References Cited

U.S. PATENT DOCUMENTS

| 4,931,444 | A | 6/1990 | Van Wauwe et al. |
| 5,346,913 | A | 9/1994 | Hsu et al. |
| 5,434,176 | A | 7/1995 | Claussner et al. |
| 5,750,553 | A | 5/1998 | Claussner et al. |
| 6,087,509 | A | 7/2000 | Claussner et al. |
| 6,977,267 | B2 | 12/2005 | Dhar et al. |

FOREIGN PATENT DOCUMENTS

| WO | WO 98/39303 | 9/1998 |
| WO | WO 99/11258 | 3/1999 |
| WO | WO 99/20617 | 4/1999 |
| WO | WO 99/20618 | 4/1999 |
| WO | WO 99/49856 | 10/1999 |
| WO | WO 00/21920 | 4/2000 |
| WO | WO 00/39081 | 7/2000 |
| WO | WO 00/48989 | 8/2000 |
| WO | WO 00/59880 | 10/2000 |
| WO | WO 01/06984 | 2/2001 |
| WO | WO 01/07044 | 2/2001 |
| WO | WO 01/07048 | 2/2001 |
| WO | WO 01/07052 | 2/2001 |
| WO | WO 01/07440 | 2/2001 |
| WO | WO 01/30781 | 5/2001 |
| WO | WO 01/51508 | 7/2001 |
| WO | WO 01/58853 | 8/2001 |
| WO | WO 02/02522 | 1/2002 |
| WO | WO 02/02539 | 1/2002 |
| WO | WO 02/28832 | 4/2002 |
| WO | WO 02/42294 | 5/2002 |
| WO | WO 02/44181 | 6/2002 |
| WO | WO 02/059114 | 8/2002 |
| WO | WO 02/096426 | 12/2002 |
| WO | WO 03/029245 | 4/2003 |

OTHER PUBLICATIONS

Arseniyadis, S. et al., "Kinetic Resolution of Amines: A Highly Enantioselective and Chemoselective Acetylating Agent with a Unique solvent-Induced Reversal of Stereoselectivity", Angew. Chem. Int. Ed., vol. 43, pp. 3314-3317 (2004).

(Continued)

Primary Examiner—Rebecca Anderson
Assistant Examiner—Jason M Nolan
(74) Attorney, Agent, or Firm—Lucas & Mercanti, LLP

(57) ABSTRACT

A process is provided for preparing spiro-hydantoin compounds of the formula II

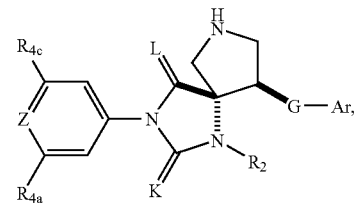

wherein Z is N or $CR_{4b}$; K and L are independently O or S; Ar is an optionally substituted aryl or heteroaryl; $A_2$ is a linker, G' is a linker; Q is a linker; and $R_2$, $R_{4a}$, $R_{4c}$, and $R_h$ are defined in the specification. The process optionally includes the enantiomeric separation of intermediates to allow preparation of enantiomers of the spiro-hydantoin compounds of formula II. Substituted spiro-hydantoin compounds may be prepared from the spiro-hydantoin compounds of formula II. The spiro-hydantoin compound of formula II and the substituted spiro-hydantoin compounds are useful in the treatment of immune or inflammatory diseases. Also, provided are products made by the instant inventive process and crystalline forms (prepared by any process) of the substituted spiro-hydantoin compound, 5-[(5S,9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid, including solvates and salts thereof, as well as methods of use thereof. Crystalline forms of certain intermediates are provided.

60 Claims, 14 Drawing Sheets

OTHER PUBLICATIONS

Diamond, M.S. et al., "The dynamic regulation of integrin adhesiveness", Current Biology, vol. 4, No. 6, pp. 506-517 (1994).

Joucla, M. et al., "Pyrrolidines from α-Amino-Acids Derivatives", Tetrahedron Letters, vol. 26, No. 23, pp. 2775-2778 (1985).

Sanfilippo, P.J. et al., "Novel Thiazole Based Heterocycles as Inhibitors of LFA-1/ICAM-1 Mediated Cell Adhesion", J. Med. Chem. vol. 38, No. 7, pp. 1057-1059 (1995).

Tsuge, O. et al., "Amino Acid Approach as a General Route to Nonstabilized Azomethine Ylides. Facile Generation of Parent Methaniminium Methylide and Its 1-Mono- and 1,1-Disubstituted Derivatives", Chemistry Letters, pp. 973-976 (1986).

Tsuge, O. et al., "Simple Generation of Nonstabilized Azomethine Ylides through Decarboxylative Condensation of α-Amino Acids with Carbonyl Compounds via 5-Oxazolidinone Intermediates", Bull. Chem. Soc. Jpn., vol. 60, pp. 4079-4089 (1987).

CRYSTALLINE FORMS AND PROCESS FOR PREPARING SPIRO-HYDANTOIN COMPOUNDS

RELATED APPLICATIONS

This application claims the benefit of U.S. Provisional Application Nos. 60/615,292 filed on Oct. 1, 2004; 60/617,905 filed on Oct. 12, 2004 and 60/717,290 filed on Sep. 15, 2005, incorporated herein by reference in its entirety.

FIELD OF INVENTION

The present invention relates to a process for preparing spiro-hydantoin compounds and substituted spiro-hydantoin compounds. Also provided are crystalline forms of the substituted spiro-hydantoin compound, 5-[(5S,9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid, including solvates and salts thereof as well as methods of use thereof. Crystalline forms of certain intermediates are also provided.

BACKGROUND OF INVENTION

A key event in an immune response involves the migration of leukocytes to a disease site. During an inflammatory response, leukocytes are recruited to the site of injury and are extravasated by a series of cellular interactions involving cell-cell and cell-substrate adhesion. The administration of compounds that inhibit these cellular interactions of leukocytes provides a route for treating inflammatory or immune diseases.

One family of molecules that serves an important adhesive function is integrins. Integrins are expressed on cell surfaces and function in cell-cell and cell-substrate adhesion. Integrins are alpha-beta heterodimers: each integrin has an alpha (α) subunit non-covalently bound to a beta (β) subunit. There are four known integrins having a $\beta_2$ or CD18 subunit, which comprise the CD11/CD18 integrin subfamily, namely, Lymphocyte Function-associated Antigen 1 (LFA-1) (CD11a/CD18 or $\alpha_L\beta_2$); Macrophage Antigen 1 (Mac-1) (CD11b/CD18 or $\alpha_M\beta_2$); p150, 95 (CD11c/CD18 or $\alpha_X\beta_2$); and $\alpha_D\beta_2$. The CD11/CD18 family of integrins is also referred to as Leukointegrins as they are expressed on the surface of various leukocyte cells, and they mediate a number of inflammation-related cellular interactions. See Diamond et al., "*The Dynamic Regulation of Integrin Adhesiveness,*" Current Biology, Vol. 4 (1994) at pp. 506-532.

When activated, the integrins bind to extracellular ligands and induce adhesion. Ligands to LFA-1 and Mac-1 comprise the intercellular adhesion molecule (ICAM) ICAM-1. The primary CD11/CD18 integrin is LFA-1, which also binds with ICAM-2 and ICAM-3. The interaction between the CD18 integrins, particularly LFA-1, and ICAMs mediates antigen presentation, T-cell proliferation, and adhesion between the endothelium and activated leukocytes, which is necessary for leukocytes to migrate from the circulatory system into tissue. Compounds inhibiting CD18 integrins, ICAMs, and/or the LFA-1: ICAM interaction have demonstrated a wide range of utilities in treating inflammatory or immune diseases. Compounds that reportedly inhibit LFA-1/ICAM for use as anti-inflammatory agents include thiadiazole-based compounds (see Intern. Pub. No. WO 99/20,618, "*Thiadiazole Amides Useful as Anti-Inflammatory Agents*" filed by Pharmacia & Upjohn Co.; and WO 99/20,617, also to Pharmacia and Upjohn); and thiazole compounds linked to phenyl and pyrazole rings (Sanfilippo et al., "*Novel Thiazole Based Heterocycles as Inhibitors of LFA-1/ICAM-1 Mediated Cell Adhesion,*" J. Med. Chem., Vol. 38 (1995) at pp. 1057-1059). Small molecules that reportedly are antagonists to the binding of ICAMs with CD18 integrins include various benzylamines and 2-bromobenzoyltryptophan compounds (see Intern. Pub. No. WO99/49,856, "*Antagonists for Treatment of CD11/CD18 Adhesion Receptor Mediated Disorders,*" filed by Genentech, Inc.), and 1-(3,5 dichlorophenyl) imidazolidines (see Intern. Pub. No. WO98/39303, "*Small Molecules Useful in the Treatment of Inflammatory Disease,*" filed by Boehringer Ingelheim Pharmaceuticals, Inc. See also Boehringer patent applications WO 01/07052, WO 01/07048, WO 01/07044, WO 01/06984, and WO 01/07440). Hydantoin compounds are disclosed in Intern. Pub. No's WO 00/59880, WO 00/39081, WO 02/02522, WO 02/02539 (all to Abbott Laboratories). LFA-1 antagonist compounds are also claimed in WO 02/059114 (to Genentech), WO 02/42294 (to Celltech), WO 01/51508 (to Science and Technology corporation), WO 00/21920 and WO 01/58853 (both to Hoffmann-LaRoche), WO 99/11258, WO 00/48989 and WO 02/28832 (all to Novartis). Hydantoin compounds are disclosed in Intern. Pub. No. WO 01/30781 A2 (published May 3, 2001) to Tanabe Seiyaku Co. Ltd, "*Inhibitors of $\alpha_L\beta_2$ Mediated Cell Adhesion,*" and in Intern. Pub. No. WO 02/44181 (published Jun. 6, 2002), "*Hydantoin Compounds Useful as Anti-Inflammatory Agents*", to the present assignee and having common inventors herewith.

U.S. patent application Publication 2004/0009998 A1 (to present assignee), incorporated herein by reference, discloses aryl or heteroaryl substituted spiro-hydantoin compounds that are effective as antagonists of Leukointegrins and/or ICAMs. The reference also discloses various processes to prepare these spiro-hydantoins, such as a multistep synthesis that includes the introduction and subsequent removal of protecting groups.

However, there are recognized difficulties associated with the adaptation of the disclosed multistep synthesis for preparing such spiro-hydantoin compounds to larger scale, such as production in a pilot plant or on a manufacturing scale. Desired in the art is a process suitable for the production of these aryl or heteroaryl substituted spiro-hydantoin compounds in larger quantities than typically prepared by laboratory scale processes. Also desired is a process that optionally provides facile separation of enantiomeric mixtures to allow the preparation of a specific enantiomer of these substituted spiro-hydantoin compounds. Additionally, there exists a need for crystalline forms of the aryl and heteroaryl substituted spiro-hydantoins as well as certain intermediates which may exhibit desirable and beneficial chemical and physical properties.

The present invention is directed to these, as well as other important aspects.

SUMMARY OF THE INVENTION

The present invention provides a process for preparing spiro-hydantoin compounds represented by formula II:

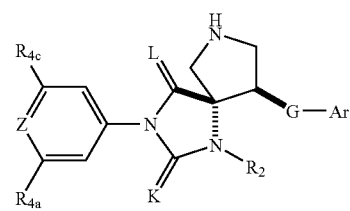

comprising: contacting alkene compound of formula I:

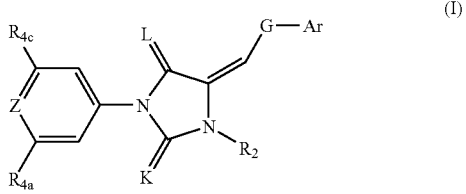

with:
i) a methylene precursor compound and
ii) glycine or glycine ester, in presence of polar solvent to afford the spiro-hydantoin compound (II) or a pharmaceutically-acceptable salt, hydrate, solvate, or prodrug thereof, wherein Ar, G, K, L, $R_2$, $R_{4a}$, $R_{4c}$, and Z are as defined herein below.

One aspect of the invention provides a process that includes the step of reacting a spiro-hydantoin compound (II) to afford a substituted spiro-hydantoin compound of formula III:

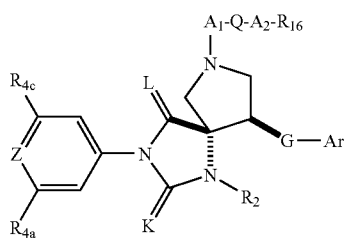

wherein $A_1$, $A_2$, Q, and $R_{16}$ are defined herein below.

The present invention also provides crystalline forms of the substituted spiro-hydantoin compound according to formula IIIn:

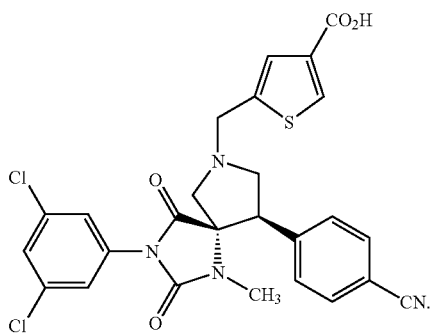

Also provided are crystalline forms of solvates and salts of the substituted spiro-hydantoin compound (IIIn).

The spiro-hydantoin compounds represented by formula II and the substituted spiro-hydantoin compounds represented by formula III are useful in the treatment of immune or inflammatory diseases.

DETAILED DESCRIPTION OF THE INVENTION

Figure 1:
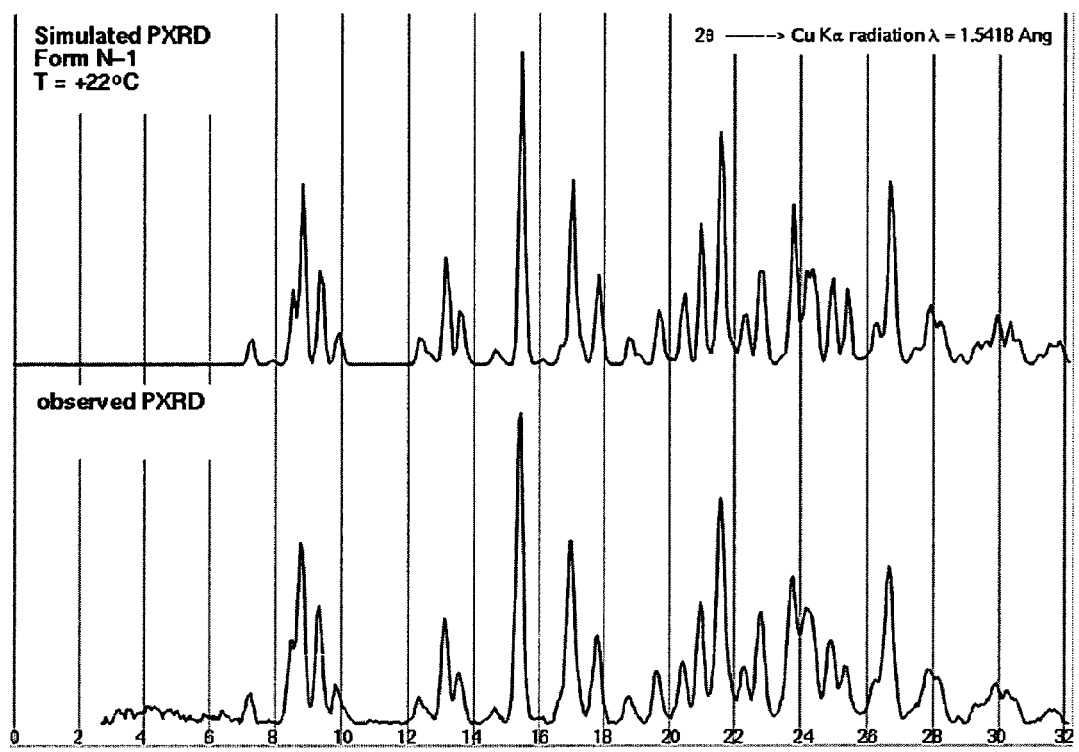
FIG. 1. shows observed and simulated powdered x-ray diffraction patterns (CuKα λ=1.5418 Å at T=22° C.) of the N-1 crystalline form of 5-[(5S,9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid.
Figure 2:
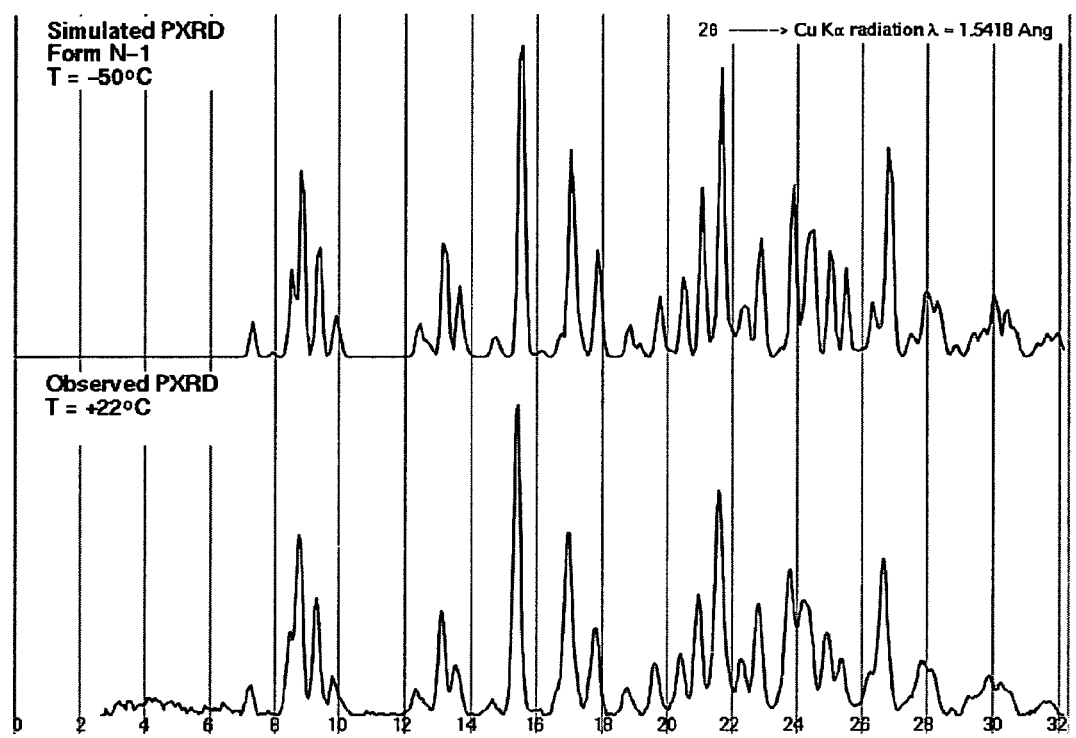
FIG. 2. shows observed and simulated powdered x-ray diffraction patterns (CuKα λ=1.5418 Å at T=−50° C.) of the N-1 crystalline form of 5-[(5S,9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid.
Figure 3:
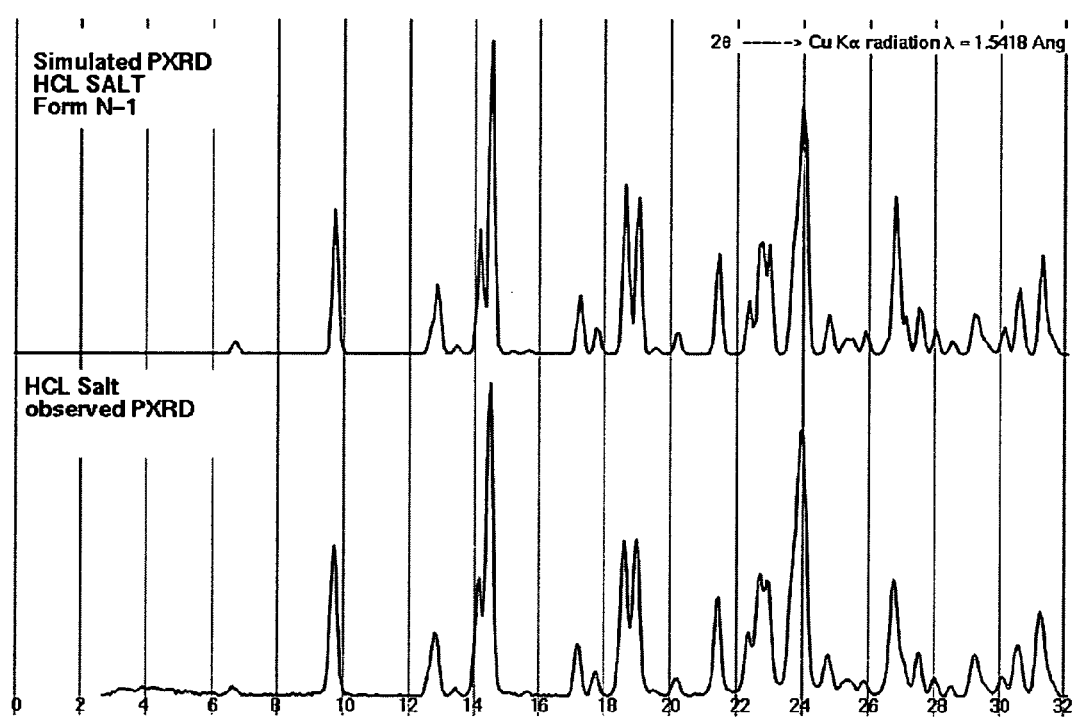
FIG. 3. shows observed and simulated powdered x-ray diffraction patterns (CuKα λ=1.5418 Å at T=22° C.) of the N-1 crystalline form of the hydrochloric acid salt of 5-[(5S,9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid.
Figure 4:
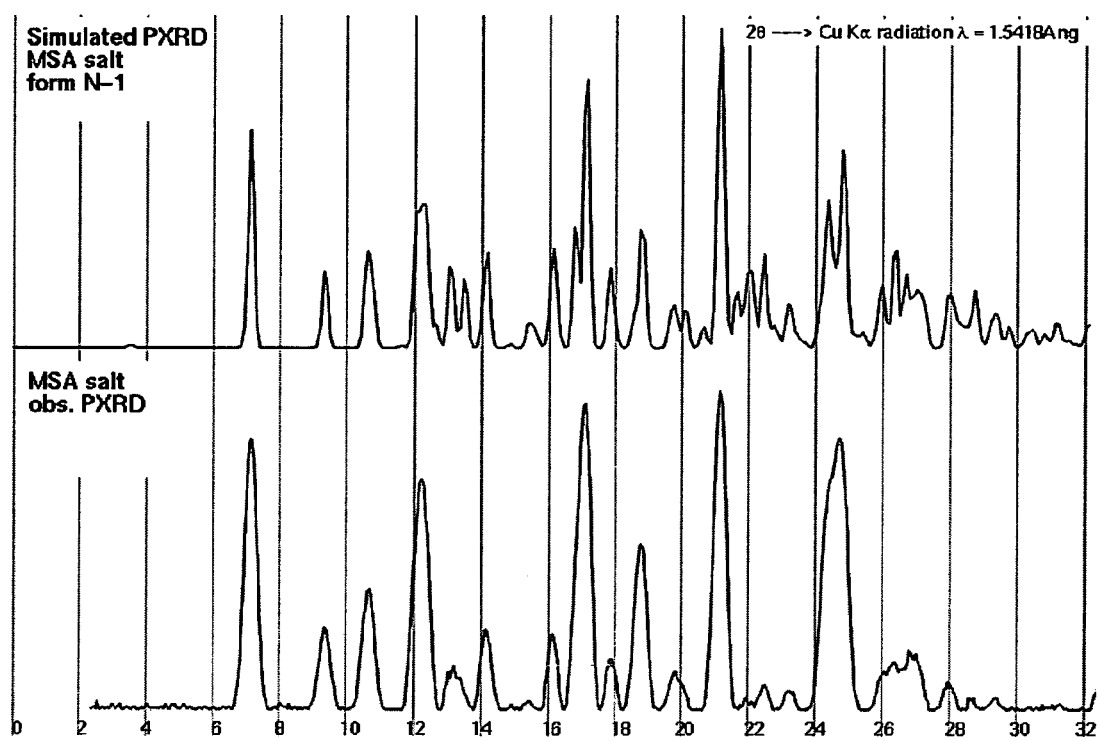
FIG. 4. shows observed and simulated powdered x-ray diffraction patterns (CuKα λ=1.5418 Å at T=22° C.) of the N-1 crystalline form of the methanesulfonic acid salt of 5-[(5S,9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid.
Figure 5:
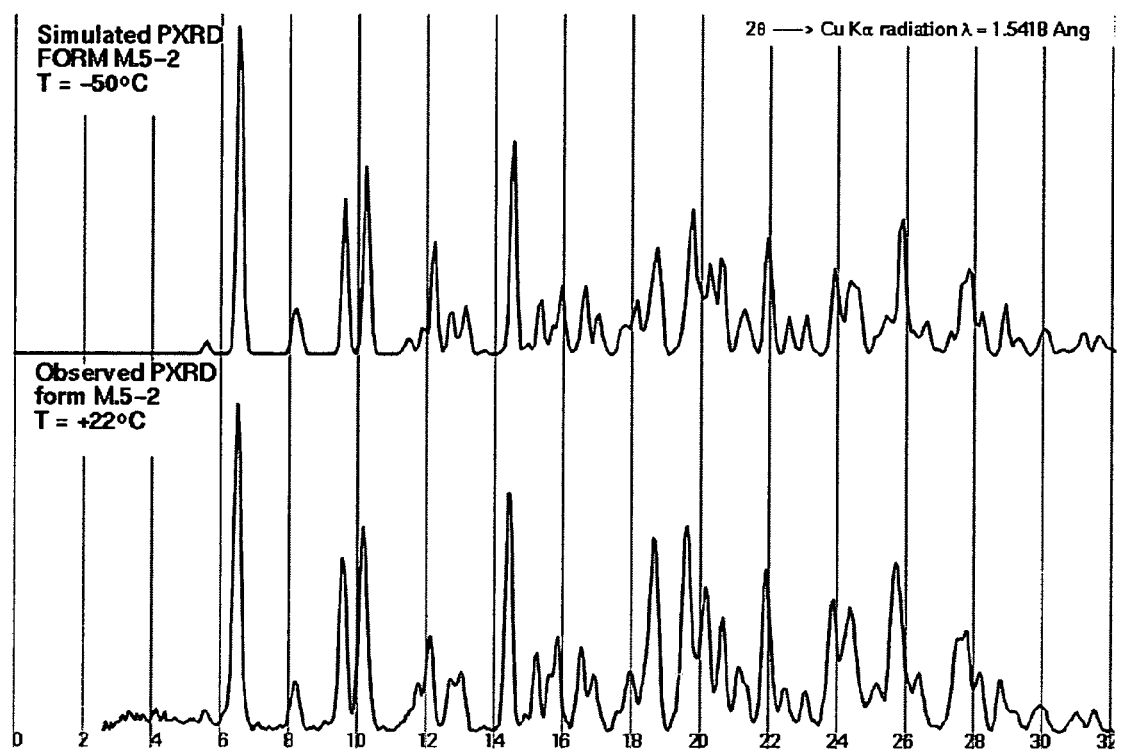
FIG. 5. shows observed and simulated powdered x-ray diffraction patterns (CuKα λ=1.5418 Å at T=−50° C.) of the crystalline form of the methanol solvate of 5-[(5S,9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid (M.5-2).
Figure 6:
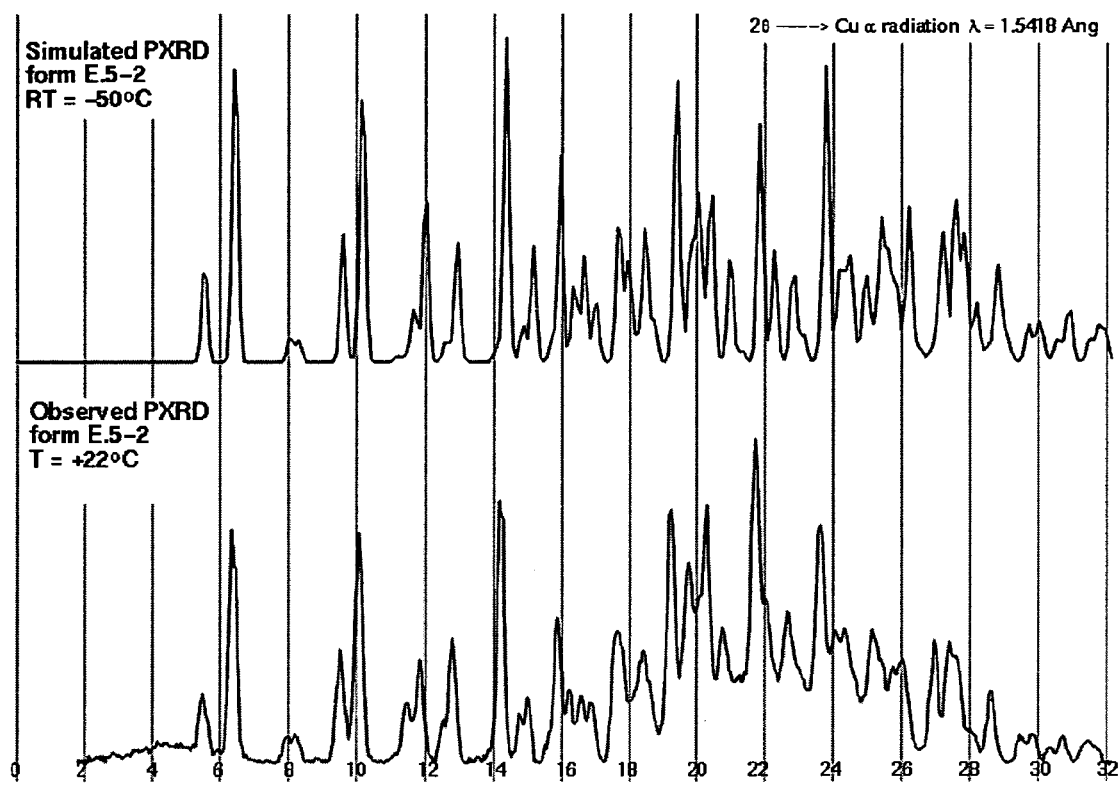
FIG. 6. shows observed and simulated powdered x-ray diffraction patterns (CuKα λ=1.5418 Å at T=−50° C.) of the crystalline form of the ethanol solvate of 5-[(5S,9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid (E.5-2).
Figure 7:
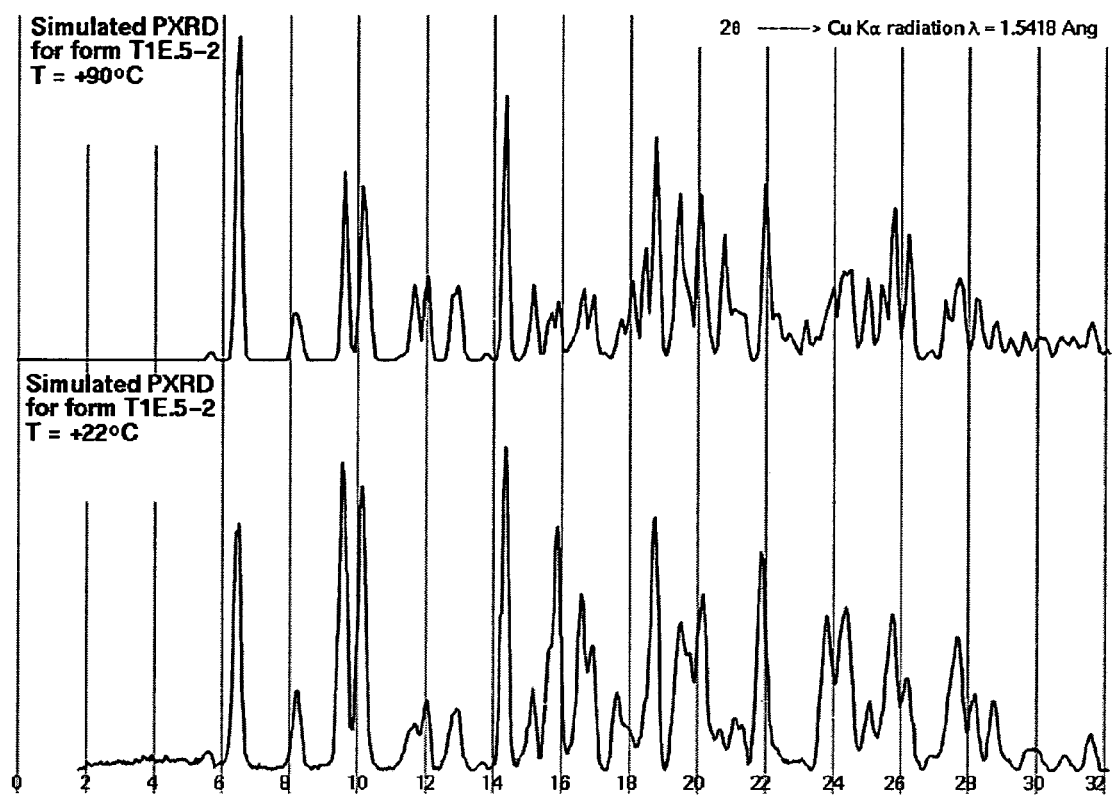
FIG. 7. shows observed and simulated powdered x-ray diffraction patterns (CuKα λ=1.5418 Å at T=−50° C.) of the desolvated crystalline form of 5-[(5S,9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid (T1E.5-2).
Figure 8:
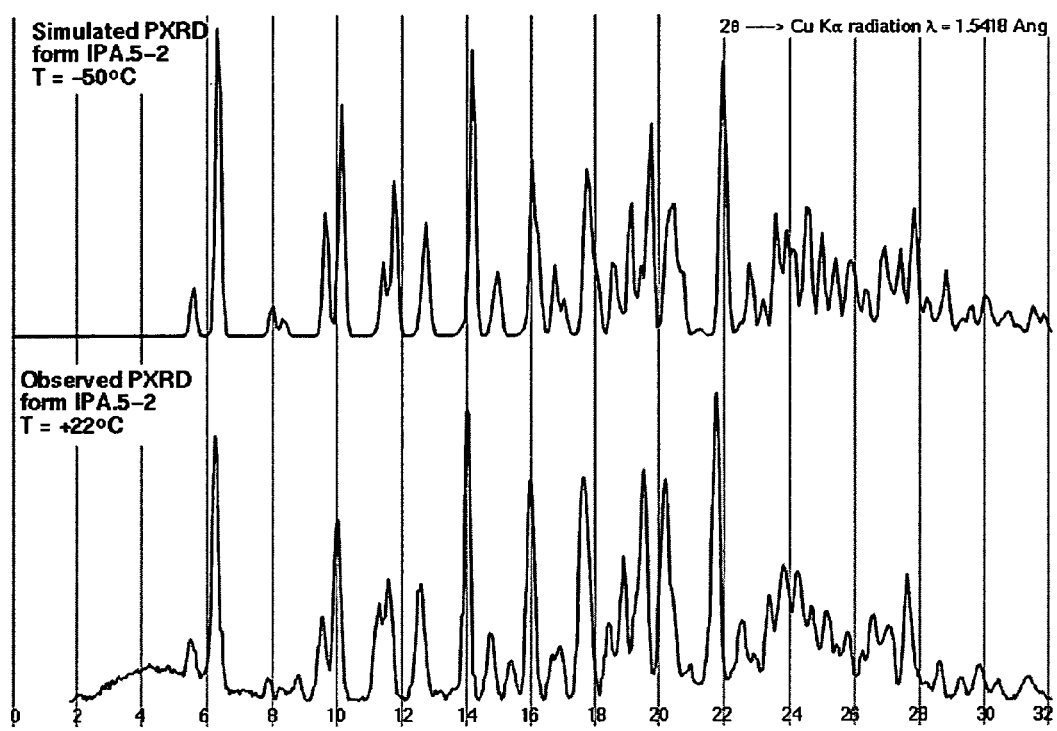
FIG. 8. shows observed and simulated powdered x-ray diffraction patterns (CuKα λ=1.5418 Å at T=−50° C.) of the crystalline form of the isopropanol solvate of 5-[(5S,9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid (IPA.5-2).
Figure 9:
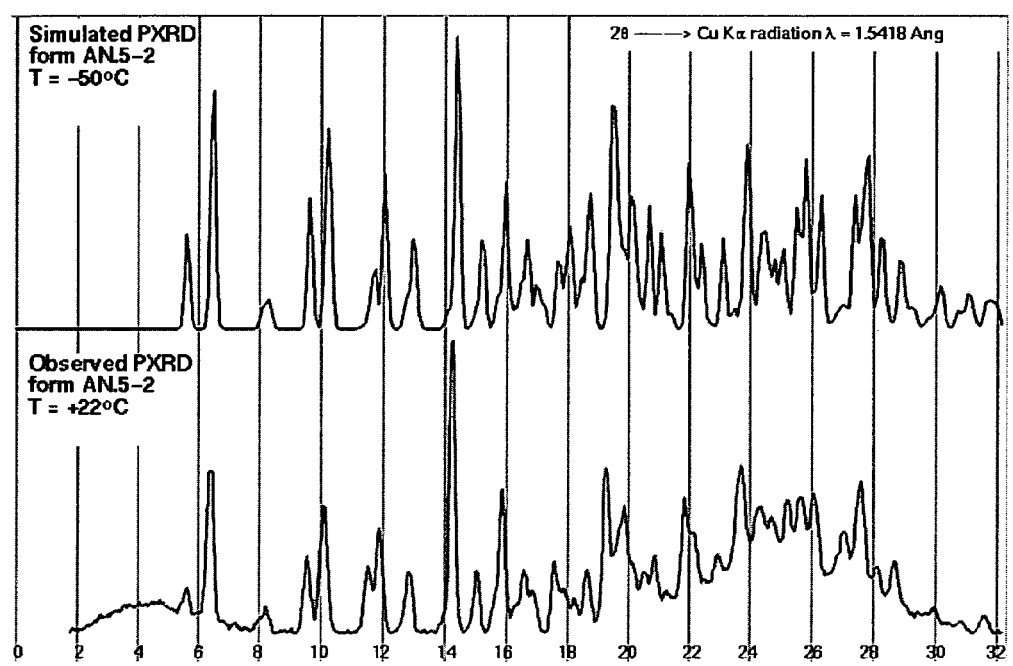
FIG. 9. shows observed and simulated powdered x-ray diffraction patterns (CuKα λ=1.5418 Å at T=−50° C.) of the crystalline form of the acrylonitrile solvate of 5-[(5S,9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid (AN.5-2).
Figure 10:
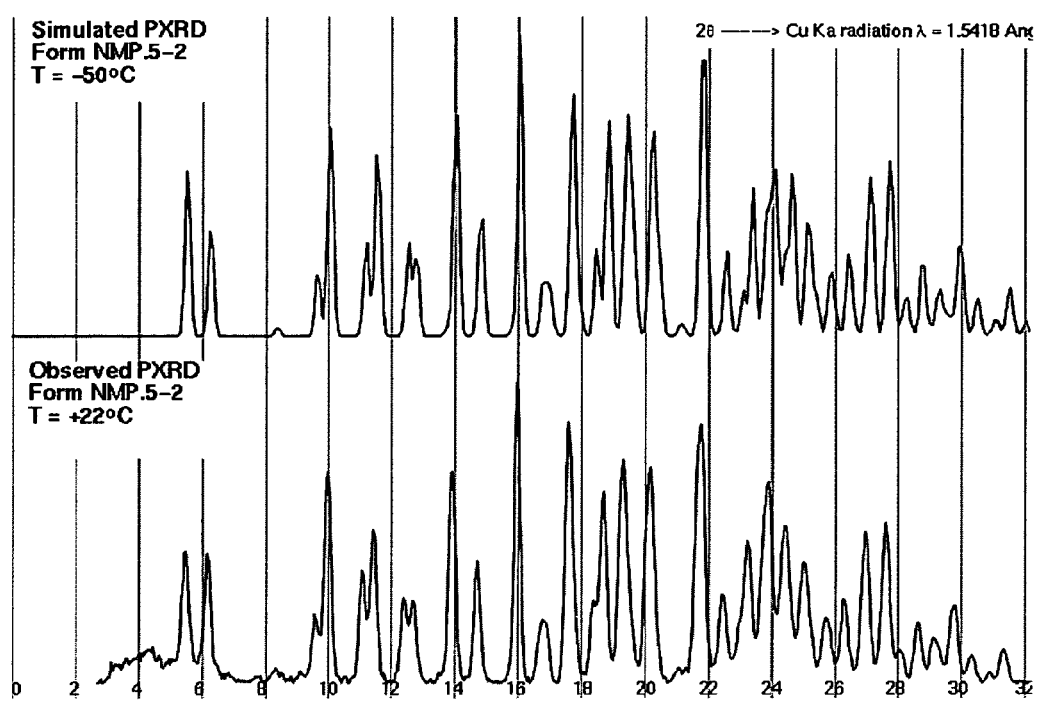
FIG. 10. shows observed and simulated powdered x-ray diffraction patterns (CuKα λ=1.5418 Å at T=−50° C.) of the crystalline form of the n-methylpyrrolidone solvate of 5-[(5S,9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid (NMP.5-2).
Figure 11:
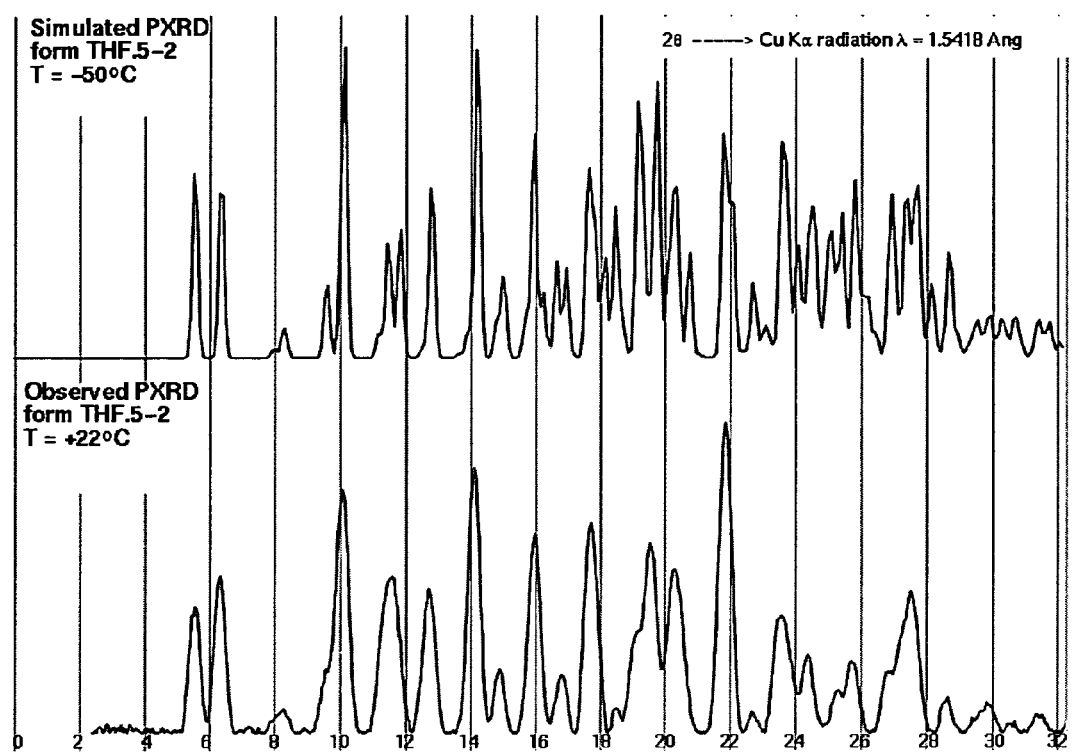
FIG. 11. shows observed and simulated powdered x-ray diffraction patterns (CuKα λ=1.5418 Å at T=−50° C.) of the crystalline form of the tetrahydrofuran solvate of 5-[(5S,9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid (THF.5-2).
Figure 12:
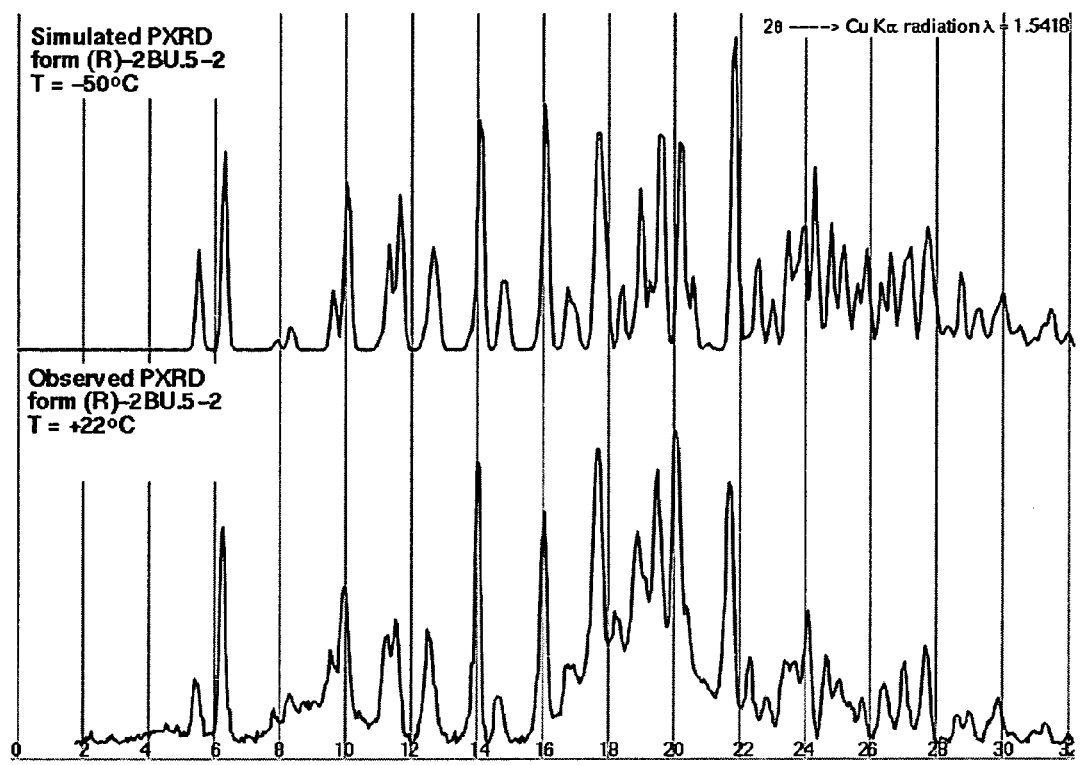
FIG. 12. shows observed and simulated powdered x-ray diffraction patterns (CuKα λ=1.5418 Å at T=−50° C.) of the crystalline form of the 1-R-(−)-2-butanol solvate of 5-[(5S,9R)-9-(4-Cyanophenyl)-3-(3,5-dichlorophenyl)-1-methyl-2, 4-dioxo-1,3,7-triazaspiro[4.4]non-7-ylmethyl]-thiophene-3-carboxylic acid ((R)-2BU.5-2).
Figure 13:
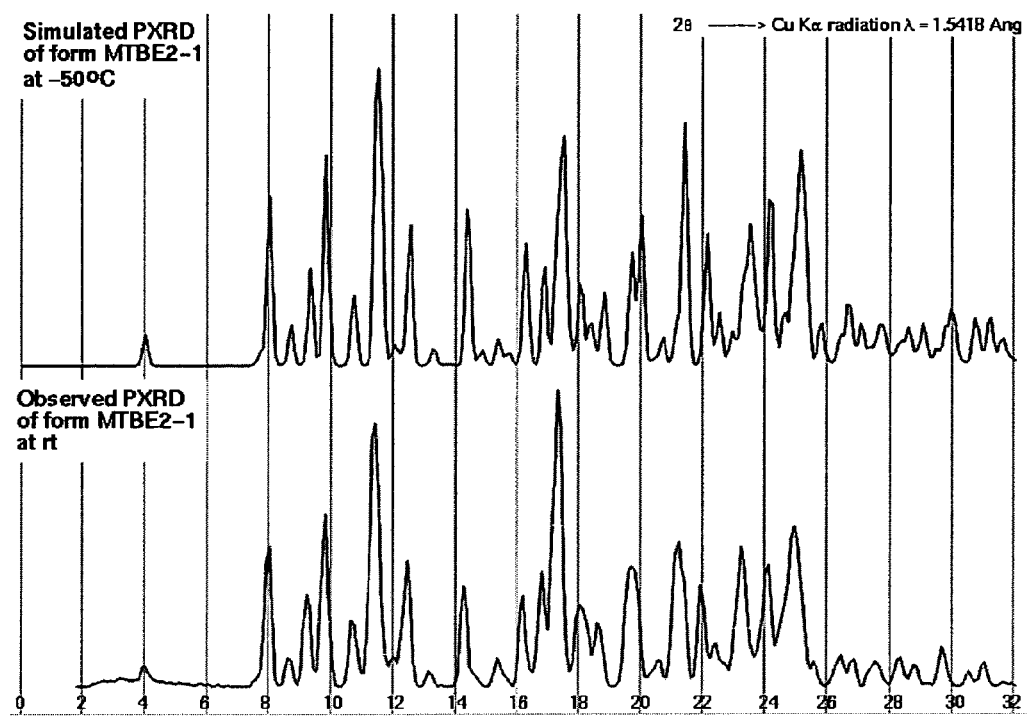
FIG. 13 shows observed (room temperature) and simulated (T=−50° C.) powdered x-ray diffraction patterns (CuKα λ=1.5418 Å) for the meso aminal dimer of 4-[3-(3, 5-Dichlorophenyl)-1-methyl-2,4-dioxo-1,3,7-triazaspiro [4.4]non-9-yl]-benzonitrile (MTBE2-1).
Figure 14:
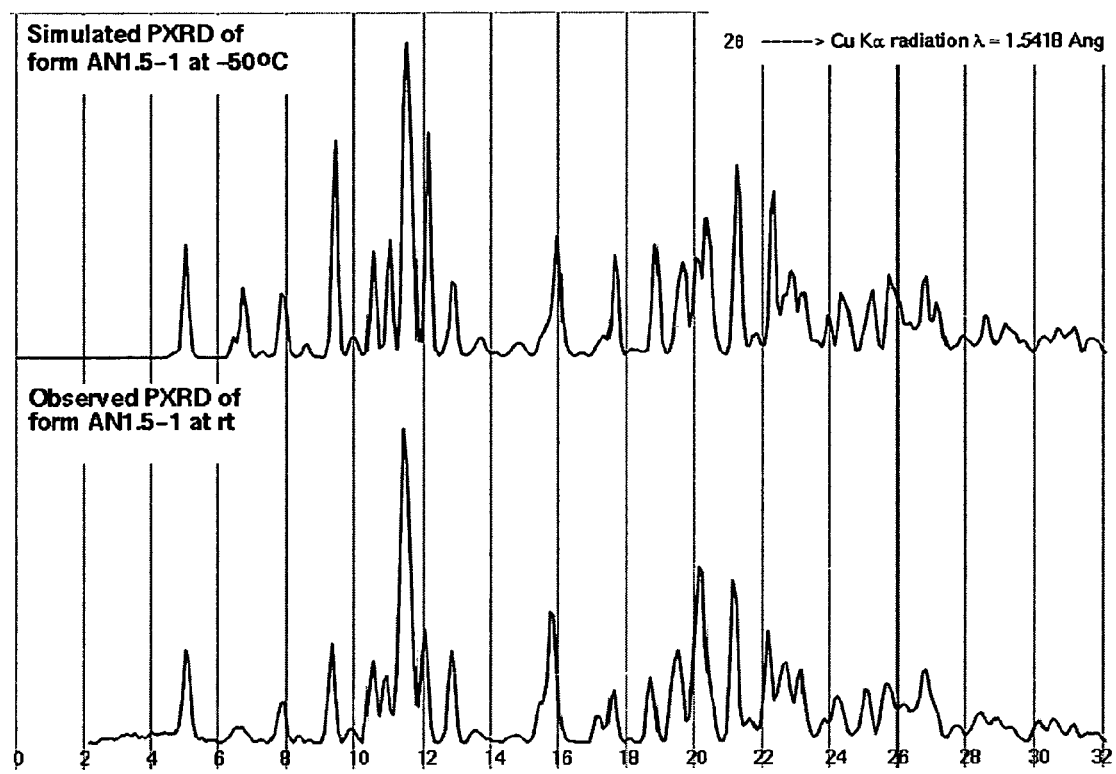
FIG. 14 shows observed (room temperature) and simulated (T=−50° C.) powdered x-ray diffraction patterns (CuKα λ=1.5418 Å) for the racemic aminal dimer of 4-[3-(3,5-Dichlorophenyl)-1-methyl-2,4-dioxo-1,3,7-triazaspiro [4.4]non-9-yl]-benzonitrile (AN1.5-1).

The following are definitions of terms used in this specification and appended claims. The initial definition provided for a group or term herein applies to that group or term throughout the specification and claims, individually or as part of another group, unless otherwise indicated.

The term "alkyl" refers to a straight or branched chain hydrocarbon groups having 1 to 12 carbon atoms, preferably 1 to 8 carbon atoms. Lower alkyl groups, that is, alkyl groups of 1 to 4 carbon atoms, are most preferred. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth. The subscript "0" refers to a bond. Thus, the term hydroxy ($C_{0-2}$)alkyl or ($C_{0-2}$)hydroxyalkyl includes hydroxy, hydroxymethyl and hydroxyethyl.

The term "substituted alkyl" refers to an alkyl group as defined above having one, two, or three substituents selected from halo (e.g., trifluoromethyl), alkenyl, substituted alkenyl, alkynyl, nitro, cyano, oxo (=O), —$OR_a$, —$SR_a$, (=S), —$NR_aR_b$, —$N(alkyl)_3^+$, —$NR_aSO_2$, —$NR_aSO_2R_c$, —$SO_2R_c$, —$SO_2NR_aR_b$, —$SO_2NR_aC(=O)R_b$, —$SO_3H$, —$PO(OH)_2$, —$C(=O)R_a$, —$CO_2R_a$, —$C(=O)NR_aR_b$, —$C(=O)(C_{1-4}alkylene)NR_aR_b$, —$C(=O)NR_a(SO_2)R_b$, —$CO_2(C_{1-4}alkylene)NR_aR_b$, —$NR_aC(=O)R_b$, —$NR_aCO_2R_b$, —$NR_a(C_{1-4}alkylene)CO_2R_b$, =N—OH, =N—O-alkyl, aryl, cycloalkyl, heterocyclo, and/or heteroaryl, wherein $R_a$ and $R_b$ are selected from hydrogen, alkyl, alkenyl, —$CO_2H$, —$CO_2$(alkyl), $C_{3-7}$cycloalkyl, phenyl, benzyl, phenylethyl, napthyl, a four to seven membered heterocyclo, and a five to six membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$ group optionally has up to three further substituents attached at any available carbon or nitrogen atom of $R_a$, $R_b$, and/or $R_c$, said substituent(s) selected from ($C_{1-6}$)alkyl, ($C_{2-6}$)alkenyl, hydroxy, halogen, cyano, nitro, $CF_3$, —$O(C_{1-6}alkyl)$, —$OCF_3$, —$C(=O)H$, —$C(=O)(C_{1-6}alkyl)$, —$CO_2H$, —$CO_2(C_{1-6}alkyl)$, —$NHCO_2(C_{1-6}alkyl)$, —$S(C_{1-6}alkyl)$, —$NH_2$, —$NH(C_{1-6}alkyl)$, —$N(C_{1-6}alkyl)_2$, —$N(CH_3)_3^+$, —$SO_2(C_{1-6}alkyl)$, —$(=O)(C_{1-4}alkylene)NH_2$, —$C(=O)(C_{1-4}alkylene)NH(alkyl)$, —$C(=O)(C_{1-4}alkylene)N(C_{1-4}alkyl)_2$, $C_{3-7}$cycloalkyl, phenyl, benzyl, phenylethyl, phenyloxy, benzyloxy, napthyl, a four to seven membered heterocyclo, or a five to six membered heteroaryl. When a substituted alkyl is substituted with an aryl, heterocyclo, cycloalkyl, or heteroaryl group, said ringed systems are as defined below and thus may have zero, one, two, or three substituents, also as defined below.

One skilled in the field will understand that, when the designation "$CO_2$" is used herein, this is intended to refer to the group

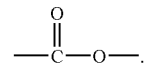

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkylene" refers to bivalent straight or branched chain hydrocarbon groups having 1 to 12 carbon atoms, preferably 1 to 8 carbon atoms, e.g., {—$CH_2$—}$_n$, wherein n is 1 to 12, preferably 1-8. Lower alkylene groups, that is, alkylene groups of 1 to 4 carbon atoms, are most preferred. The terms "alkenylene" and "alkynylene" refer to bivalent radicals of alkenyl and alkynyl groups, respectively, as defined above.

When reference is made to a substituted alkenyl, alkynyl, alkylene, alkenylene, or alkynylene group, these groups are substituted with one to three substituents as defined above for substituted alkyl groups.

The term "heteroalkylene" is used herein to refer to saturated and unsaturated bivalent straight or branched chain hydrocarbon groups having 2 to 12 carbon atoms, preferably 2 to 8 carbon atoms, wherein one or two carbon atoms in the straight chain are replaced by heteroatom(s) selected from —O—, —S—, —S(=O)—, —$SO_2$—, —NH—, and —$NHSO_2$—. Thus, the term "heteroalkylene" includes bivalent alkoxy, thioalkyl, and aminoalkyl groups, as defined below, as well as alkylene and alkenylene groups having a combination of heteroatoms in the alkyl chain. As an illustration, a "heteroalkylene" herein may comprise groups such as —$CH_2$—NH—, —S—$CH_2$)$_{1-5}$NH—$CH_2$—, —O—$(CH_2)_{1-5}$S(=O)—$CH_2$—, and so forth. Preferably, a heteroalkylene does not have two adjacent atoms simultaneously selected from —O— and —S—. When a subscript is used with the term heteroalkylene, e.g., as in $C_{2-3}$heteroalkylene, the subscript refers to the number of carbon atoms in the group in addition to heteroatoms. Thus, for example, a $C_{1-2}$heteroalkylene may include groups such as —NH—$CH_2$—, —$CH_2$—NH—$CH_2$—, —$CH_2$—$CH_2$—NH—, —S—$CH_2$—, —$CH_2$—S—$CH_2$—, —O—$CH_2$—NH—$CH_2$—, —$CH_2$—O—$CH_2$— and so forth.

The term "substituted heteroalkylene" refers to a heteroalkylene group as defined above wherein at least one of the nitrogen or carbon atoms in the heteroalkylene chain is bonded to (or substituted with) a group other than hydrogen.

Carbon atoms in the heteroalkylene chain may be substituted with a group selected from those recited above for substituted alkyl groups, or with a further alkyl or substituted alkyl group. Nitrogen atoms of the heteroalkylene chain may be substituted with a group selected from alkyl, alkenyl, alkynyl, cyano, and -$A_1$-Q-$A_2$-$R_{16}$, wherein $A_1$ is a bond, $C_{1-2}$alkylene, or $C_{2-3}$alkenylene; Q is a bond, —C(=O)—, —C(=O)NR$_d$—, —C(=S)NR$_d$—, —SO$_2$—, —SO$_2$NR$_d$—, —CO$_2$—, or —NR$_d$CO$_2$—; $A_2$ is a bond, $C_{1-3}$alkylene, $C_{2-3}$alkenylene, —$C_{1-4}$alkylene-NR$_d$—, —$C_{1-4}$ alkylene-NR$_d$C(=O)—, —$C_{1-4}$alkylene-S—, —$C_{1-4}$alkylene-SO$_2$—, or —$C_{1-4}$alkylene-O—, wherein said $A_2$ alkylene groups are branched or straight chain and, optionally, substituted as defined herein for substituted alkylene; each $R_{16}$ is independently hydrogen, alkyl, substituted alkyl, alkenyl, substituted alkenyl, aryl, heteroaryl, heterocyclo, or cycloalkyl; and $R_d$ is selected from hydrogen, alkyl, and substituted alkyl, as defined herein, provided, however, that $R_{16}$ is not hydrogen when $A_1$, Q, and $A_2$ are each bonds. When $R_{16}$ is aryl, heteroaryl, cycloalkyl, or heterocyclo, these rings are, in turn, optionally substituted with one to three groups as defined below in the definitions for these terms.

The term "alkoxy" refers to an alkyl or substituted alkyl group as defined above having one or two oxygen atoms (—O—) in the alkyl chain. For example, the term "alkoxy" includes the groups —O—$C_{1-12}$alkyl, —($C_{1-6}$alkylene)-O—$C_{1-6}$alkyl, —($C_{1-4}$alkylene-O—$C_{1-4}$alkylene)-O—$C_{1-4}$alkyl, and so forth.

The term "thioalkyl" or "alkylthio" refers to an alkyl or substituted alkyl group as defined having one or two sulfur atoms in the alkyl chain. For example, the term "thioalkyl" or "alkylthio" includes the groups —S—$C_{1-12}$alkyl, —(S—$C_{1-6}$alkylene)-S—$C_{1-6}$alkyl, and so forth.

The terms "aminoalkyl" or "alkylamino" refer to an alkyl or substituted alkyl group as defined above having one or two nitrogen (—NR—) atoms in the alkyl chain. For example, the term "aminoalkyl" includes the groups —NR—$C_{1-12}$alkyl, —NR—$C_{1-6}$alkylene-NR—$C_{1-6}$alkyl, etc. (where R is preferably hydrogen but may include alkyl or substituted alkyl as defined above.) When a subscript is used with reference to an alkoxy, thioalkyl or aminoalkyl, the subscript refers to the number of carbon atoms that the group may contain in addition to heteroatoms. Thus, for example, monovalent $C_{1-2}$aminoalkyl includes the groups —CH$_2$—NH$_2$, —NH—CH$_3$, —(CH$_2$)$_2$—NH$_2$, —NH—CH$_2$—CH$_3$, —CH$_2$—NH—CH$_3$, and —N—(CH$_3$)$_2$. A lower aminoalkyl comprises an aminoalkyl having one to four carbon atoms. "Amino" refers to the group NH$_2$.

The alkoxy, thioalkyl, or aminoalkyl groups may be monovalent or bivalent. By "monovalent" it is meant that the group has a valency (i.e., ability to combine with another group), of one, and by "bivalent" it is meant that the group has a valency of two. Thus, for example, a monovalent alkoxy includes groups such as —O—$C_{1-12}$alkyl, —$C_{1-6}$alkylene-O—$C_{1-6}$alkyl, —$C_{1-4}$alkylene-O—$C_{1-4}$alkylene-O—$C_{1-4}$alkyl, whereas a bivalent alkoxy includes groups such as —O—$C_{1-12}$alkylene-, —$C_{1-6}$alkylene-O—$C_{1-6}$-alkylene-, —$C_{1-4}$alkylene-O—$C_{1-4}$alkylene-O—$C_{1-4}$alkylene-, and so forth.

It should be understood that the selections for alkoxy, thioalkyl, and aminoalkyl will be made by one skilled in the field to provide stable compounds.

The term "acyl" refers to a carbonyl group linked to an organic radical, more particularly, the group —C(=O)R$_e$, as well as the bivalent groups —C(=O)— or —C(=O)R$_e$—, which are linked to organic radicals. The group R$_e$ can be selected from alkyl, alkenyl, alkynyl, aminoalkyl, substituted alkyl, substituted alkenyl, or substituted alkynyl, as defined herein, or when appropriate, the corresponding bivalent group, e.g., alkylene, alkenylene, etc. Accordingly, in alkene compound (I), spiro-hydantoin compound (II), and substituted spiro-hydantoin compound (III), when it is recited that G can be "acyl," this is intended to encompass a selection for G of —C(=O)— and also the groups —C(=O)R$_e$— or —R$_e$C(=O)—, wherein in this instance, the group R$_e$ will be selected from bivalent groups, e.g., alkylene, alkenylene, alkynylene, bivalent aminoalkyl, substituted alkylene, substituted alkenylene, or substituted alkynylene.

The term "alkoxycarbonyl" refers to a carboxy group

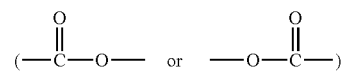

linked to an organic radical (CO$_2$R$_e$), as well as the bivalent groups —CO$_2$—, —CO$_2$R$_e$— which are linked to organic radicals in alkene compound (I), spiro-hydantoin compound (II) and substituted spiro-hydantoin compound (III), wherein R$_e$ is as defined above for acyl. The organic radical to which the carboxy group is attached may be monovalent (e.g., —CO$_2$-alkyl or —OC(=O)alkyl), or bivalent (e.g., —CO$_2$-alkylene, —OC(=O)alkylene, etc.). Accordingly, in alkene compound (I), spiro-hydantoin compound (II), and substituted spiro-hydantoin compound (III), when it is recited that G can be "alkoxycarbonyl," this is intended to encompass a selection for G of —CO$_2$— and also the groups —CO$_2$R$_e$— or —R$_e$CO$_2$—, wherein in this instance, the group R$_e$ will be selected from bivalent groups, e.g., alkylene, alkenylene, alkynylene, bivalent aminoalkyl, substituted alkylene, substituted alkenylene, or substituted alkynylene.

The term "amide" or "amidyl" refers to the group —C(=O)NR$_a$R$_b$, wherein the groups R$_a$ and R$_b$ are defined as recited above in the definition for substituted alkyl groups.

The term "sulfonyl" refers to a sulphoxide group linked to an organic radical, more particularly, the monovalent group —S(O)$_{1-2}$—R$_a$, or the bivalent group —S(O)$_{1-2}$-linked to organic radicals. Accordingly, in alkene compound (I), spiro-hydantoin compound (II), and substituted spiro-hydantoin compound (III), when it is recited that G can be "sulfonyl," this is intended to encompass a selection for G of —S(=O)— or —SO$_2$— as well as the groups —S(=O)R$_e$—, —R$_e$S(=O)—, —SO$_2$R$_e$—, or —R$_e$SO$_2$—, wherein in this instance, the group R$_e$ will be selected from those recited above for acyl and alkoxycarbonyl groups.

The term "sulfonamidyl" refers to the group —S(O)$_2$NR$_a$R$_b$, wherein R$_a$ and R$_b$ are as defined above for substituted alkyl groups. Additionally, the sulfonamidyl group may be bivalent, in which case one of the groups R$_a$ and R$_b$ will be a bond. Thus, in alkene compound (I), spiro-hydantoin compound (II), and substituted spiro-hydantoin compound (III), when it is stated that G may be sulfonamidyl, it is intended to mean that G is a group —S(O)$_2$NR$_a$—.

The term "cycloalkyl" refers to a fully saturated or partially saturated cyclic hydrocarbon group containing from 1 to 4 rings and 3 to 8 carbons per ring. Exemplary fully saturated cycloalkyl groups include cyclopropyl, cyclobutyl, cyclopentyl, and cyclohexyl. Exemplary partially saturated cycloalkyl groups include cyclobutenyl, cyclopentenyl, and cyclohexenyl. "Substituted cycloalkyl" refers to a cycloalkyl group substituted with one or more substituents, preferably 1 to 4 substituents, at any available point of attachment. Exemplary substituents include, but are not limited to, halogen, trifluoromethyl, trifluoromethoxy, alkyl, substituted alkyl, alkenyl, substituted alkenyl, alkynyl, nitro, cyano, oxo (=O), —$OR_a$, —$SR_a$, (=S), —$NR_aR_b$, —$N(alkyl)_3^+$, —$NR_aSO_2$, —$NR_aSO_2R_c$, —$SO_2R_c$, —$SO_2NR_aR_b$, —$SO_2NR_aC(=O)R_b$, —$SO_3H$, —$PO(OH)_2$, —$C(=O)R_a$, —$CO_2R_a$, —$C(=O)NR_aR_b$, —$C(=O)(C_{1-4}$alkylene)$NR_aR_b$, —$C(=O)NR_a(SO_2)R_b$, —$CO_2(C_{1-4}$alkylene)$NR_aR_b$, —$NR_aC(=O)R_b$, —$NR_aCO_2R_b$, —$NR_a(C_{1-4}$alkylene)$CO_2R_b$, =N—OH, =N—O-alkyl, aryl, cycloalkyl, heterocyclo, and/or heteroaryl, wherein $R_a$, $R_b$ and $R_c$ are as defined above for substituted alkyl groups, and are also in turn optionally substituted as recited above in the definition for substituted alkyl groups. The term "cycloalkyl" also includes such rings having a second ring fused thereto (e.g., including benzo, heterocyclo, or heteroaryl rings) or having a carbon-carbon bridge of 3 to 4 carbon atoms. When a cycloalkyl is substituted with a further ring (or has a second ring fused thereto), said ring in turn is optionally substituted with one to two of $(C_{1-4})$alkyl, $(C_{2-4})$alkenyl, halogen, hydroxy, cyano, nitro, $CF_3$, —$O(C_{1-4}$ alkyl), —$OCF_3$, —$C(=O)H$, —$C(=O)(C_{1-4}$ alkyl), —$CO_2H$, —$CO_2(C_{1-4}$alkyl), —$NHCO_2(C_{1-4}$alkyl), —$S(C_{1-4}$ alkyl), —$NH_2$, —$NH(C_{1-4}$alkyl), —$N(C_{1-4}$alkyl$)_2$, —$N(C_{1-4}$alkyl$)_3^+$, —$SO_2(C_{1-4}$alkyl), —$C(=O)(C_{1-4}$alkylene)$NH_2$, —$C(=O)(C_{1-4}$alkylene)NH(alkyl), and/or —$C(=O)(C_{1-4}$alkylene)$N(C_{1-4}$alkyl$)_2$.

The term "cycloalkyl" includes cyclopropyl, cyclobutyl, cyclopentyl, cyclohexyl, cycloheptyl, cyclooctyl, etc., as well as the following ring systems,

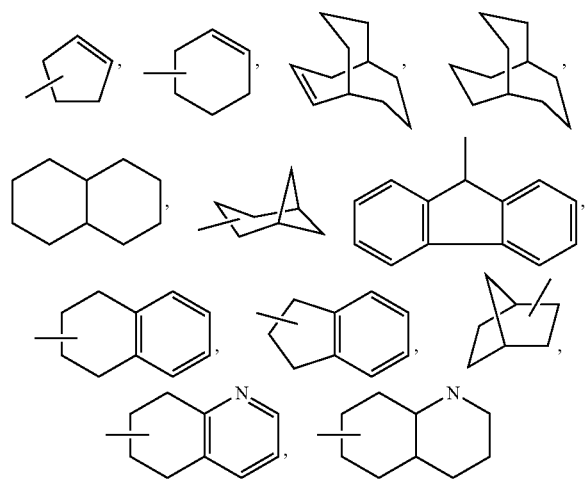

and the like, which optionally may be substituted at any available atoms of the ring(s). Preferred cycloalkyl groups include cyclopropyl, cyclobutyl, cyclopentyl, cyclohexyl, and

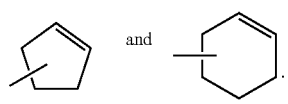

The term "halo" or "halogen" refers to fluoro, chloro, bromo, and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

The term "aryl" refers to phenyl, biphenyl, 1-naphthyl and 2-naphthyl. The term "aryl" includes such rings having zero, one, two or three substituents selected from halogen, trifluoromethyl, trifluoromethoxy, alkyl, substituted alkyl, alkenyl, substituted alkenyl, alkynyl, nitro, cyano, —$OR_a$, —$SR_a$, (=S), —$NR_aR_b$, —$N(alkyl)_3^+$, —$NR_aSO_2$, —$NR_aSO_2R_c$, —$SO_2R_c$—$SO_2NR_aR_b$, —$SO_2NR_aC(=O)R_b$, —$SO_3H$, —$PO(OH)_2$, —$C(=O)R_a$, —$CO_2R_a$, —$C(=O)NR_aR_b$, —$C(=O)(C_{1-4}$alkylene)$NR_aR_b$, —$C(=O)NR_a(SO_2)R_b$, —$CO_2(C_{1-4}$alkylene)$NR_aR_b$, —$NR_aC(=O)R_b$, —$NR_aCO_2R_b$, —$NR_a(C_{1-4}$alkylene)$CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. Additionally, two substituents attached to an aryl, particularly a phenyl group, may join to form a further ring such as a fused or spiro-ring, e.g., cyclopentyl or cyclohexyl, or fused heterocyclo or heteroaryl. When an aryl is substituted with a further ring (or has a second ring fused thereto), said ring in turn is optionally substituted with one to two of $(C_{1-4})$alkyl, $(C_{2-4})$alkenyl, halogen, hydroxy, cyano, nitro, $CF_3$, $O(C_{1-4}$alkyl), $OCF_3$, $C(=O)H$, $C(=O)(C_{1-4}$alkyl), $CO_2H$, $CO_2(C_{1-4}$alkyl), —$NHCO_2(C_{1-4}$alkyl), —$S(C_{1-4}$alkyl), —$NH_2$, —$NH(C_{1-4}$alkyl), —$N(C_{1-4}$alkyl$)_2$, —$N(C_{1-4}$alkyl$)_3^+$, —$SO_2(C_{1-4}$alkyl), —$C(=O)(C_{1-4}$alkylene)$NH_2$, —$C(=O)(C_{1-4}$alkylene)NH(alkyl), and/or —$C(=O)(C_{1-4}$alkylene)$N(C_{1-4}$alkyl$)_2$.

Thus, examples of aryl groups include:

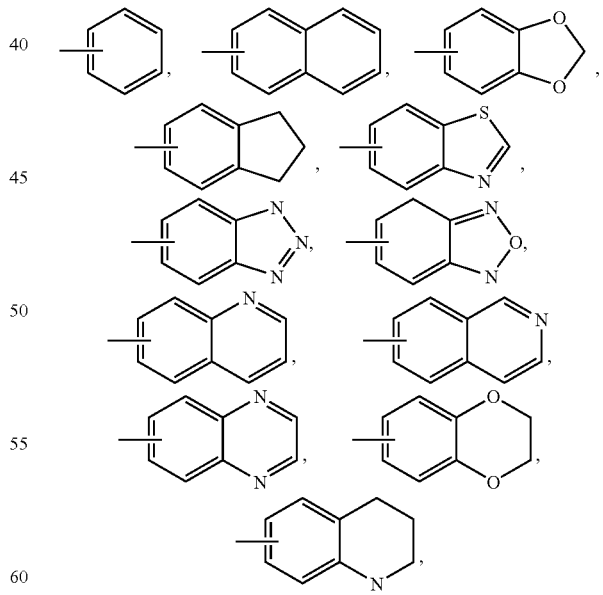

and the like, which optionally may be substituted at any available carbon or nitrogen atom. A preferred aryl group is optionally-substituted phenyl.

The terms "heterocyclo" or "heterocyclic" refers to substituted and unsubstituted non-aromatic 3- to 7-membered monocyclic groups, 7- to 11-membered bicyclic groups, and 10- to 15-membered tricyclic groups, in which at least one of the rings has at least one heteroatom (O, S or N). Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero, one, two or three substituents selected from halogen, trifluoromethyl, trifluoromethoxy, alkyl, substituted alkyl, alkenyl, substituted alkenyl, alkynyl, nitro, cyano, oxo (=O), —$OR_a$, —$SR_a$, (=S), —$NR_aR_b$, —$N(alkyl)_{3+}$, —$NR_aSO_2$, —$NR_aSO_2R_c$, —$SO_2R_c$, —$SO_2NR_aR_b$, —$SO_2NR_aC(=O)R_b$, —$SO_3H$, —$PO(OH)_2$, —$C(=O)R_a$, —$CO_2R_a$, —$C(=O)NR_aR_b$, —$NR_aC(=O)R_b$, —$C(=O)(C_{1-4}alkylene)NR_aR_b$, —$C(=O)NR_a(SO_2)R_b$, —$CO_2(C_{1-4}alkylene)NR_aR_b$, —$NR_aCO_2R_b$, —$NR_a(C_{1-4} alkylene)CO_2R_b$, =N—OH, =N—O-alkyl, aryl, cycloalkyl, heterocyclo, and/or heteroaryl, wherein $R_a$, $R_b$ and $R_c$ are as defined above for substituted alkyl groups, and are also in turn optionally substituted as recited above. When a heterocyclo is substituted with a further ring, said ring in turn is optionally substituted with one to two of $(C_{1-4})$alkyl, $(C_{2-4})$alkenyl, halogen, hydroxy, cyano, nitro, $CF_3$, $O(C_{1-4}$ alkyl), $OCF_3$, $C(=O)H$, $C(=O)(C_{1-4}alkyl)$, $CO_2H$, $CO_2(C_{1-4}alkyl)$, —$NHCO_2(C_{1-4}alkyl)$, —$S(C_{1-4}alkyl)$, —$NH_2$, —$NH(C_{1-4}alkyl)$, —$N(C_{1-4}alkyl)_2$, —$N(C_{1-4}alkyl)_{3+}$, —$SO_2(C_{1-4}alkyl)$, —$C(=O)(C_{1-4}alkylene)NH_2$, —$C(=O)(C_{1-4}alkylene)NH(alkyl)$, and/or —$C(=O)(C_{1-4}alkylene)N(C_{1-4}alkyl)_2$.

Exemplary monocyclic groups include azetidinyl, pyrrolidinyl, oxetanyl, imidazolinyl, oxazolidinyl, isoxazolinyl, thiazolidinyl, isothiazolidinyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

Preferred heterocyclo groups in alkene compound (I), spiro-hydantoin compound (II), and substituted spiro-hydantoin compound (III) include

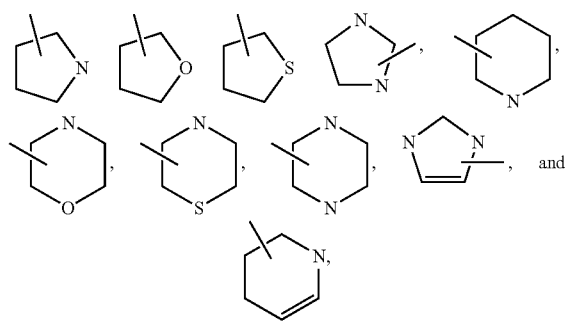

and which optionally may be substituted.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from halogen, trifluoromethyl, trifluoromethoxy, alkyl, substituted alkyl, alkenyl, substituted alkenyl, alkynyl, nitro, cyano, —$OR_a$ —$SR_a$, (=S), —$NR_aR_b$, —$N(alkyl)_3^+$, —$NR_aSO_2$, —$NR_aSO_2R_c$, —$SO_2R_c$, —$SO_2NR_aR_b$, —$SO_2NR_aC(=O)R_b$, —$SO_3H$, —$PO(OH)_2$, —$C(=O)R_a$, —$CO_2R_a$, —$C(=O)(C_{1-4}alkylene)NR_aR_b$, —$C(=O)NR_aR_b$, —$C(=O)NR_a(SO_2)R_b$, —$CO_2(C_{1-4}alkylene)NR_aR_b$, —$NR_aC(=O)R_b$, —$NR_aCO_2R_b$, —$NR_a(C_{1-4}alkylene)CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. When a heteroaryl is substituted with a further ring, said ring in turn is optionally substituted with one to two of $(C_{1-4})$alkyl, $(C_{2-4})$alkenyl, halogen, hydroxy, cyano, nitro, $CF_3$, —$O(C_{1-4}$ alkyl), —$OCF_3$, —$C(=O)H$, —$C(=O)(C_{1-4}$ alkyl), —$CO_2H$, —$CO_2(C_{1-4}alkyl)$, —$NHCO_2(C_{1-4}alkyl)$, —$S(C_{1-4}$ alkyl), —$NH_2$, —$NH(C_{1-4}alkyl)$, —$N(C_{1-4}alkyl)_2$, —$N(C_{1-4}alkyl)_{3+}$, —$SO_2(C_{1-4}alkyl)$, —$C(=O)(C_{1-4}alkylene)NH_2$, —$C(=O)(C_{1-4}alkylene)NH(alkyl)$, and/or —$C(=O)(C_{1-4}alkylene)N(C_{1-4}alkyl)_2$.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

In alkene compound (I), spiro-hydantoin compound (II), and substituted spiro-hydantoin compound (III), preferred heteroaryl groups include

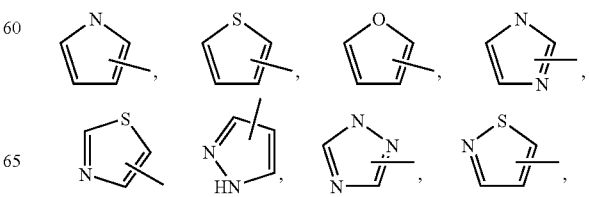

-continued

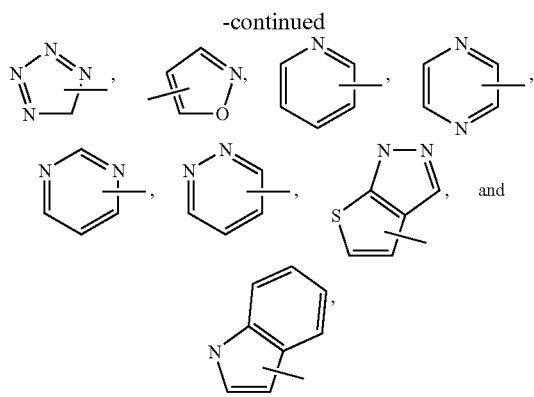

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., imidazolyl), unless otherwise specifically indicated the reference is intended to include rings having 0 to 3, preferably 0-2, substituents selected from those recited above for the aryl, cycloalkyl, heterocyclo, and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

As used herein, the structure of spiro-hydantoin compound (II) represents either enantiomer, spiro-hydantoin compound (IIa) or spiro-hydantoin compound (IIb), or mixtures thereof, including a racemic mixture.

As used herein, the structure of spiro-hydantoin compound (IIc) represents either enantiomer, spiro-hydantoin compound (IId) or spiro-hydantoin compound (IIe), or mixtures thereof, including a racemic mixture.

As used herein, the structure of spiro-hydantoin compound (IIf) represents either enantiomer, spiro-hydantoin compound (IIg) or spiro-hydantoin compound (IIh), or mixtures thereof, including a racemic mixture.

As used herein, the structure of substituted spiro-hydantoin compound (III) represents either enantiomer, substituted spiro-hydantoin compound (IIIa) or substituted spiro-hydantoin compound (IIIb), or mixtures thereof, including a racemic mixture.

As used herein, the structure of substituted spiro-hydantoin compound (IIIc) represents either enantiomer, substituted spiro-hydantoin compound (IIId) or substituted spiro-hydantoin compound (IIIe), or mixtures thereof, including a racemic mixture.

As used herein, the structure of substituted spiro-hydantoin compound (IIIf) represents either enantiomer, substituted spiro-hydantoin compound (IIIg) or substituted spiro-hydantoin compound (IIIh), or mixtures thereof, including a racemic mixture.

As used herein, the structure of substituted spiro-hydantoin compound (IIIm) represents either enantiomer, substituted spiro-hydantoin compound (IIIn) or substituted spiro-hydantoin compound (IIIp), or mixtures thereof, including a racemic mixture.

Throughout the specification, groups and substituents thereof may be chosen by one skilled in the field to provide stable moieties and compounds useful as pharmaceutically-acceptable compounds and/or intermediate compounds useful in making pharmaceutically-acceptable compounds.

The compounds of formulae I to III can form salts which are also within the scope of this invention. Unless otherwise indicated, reference to a compound of one of formulae I to III is understood to include reference to salts thereof. The term "salt(s)" denotes acidic and/or basic salts formed with inorganic and/or organic acids and bases. In addition, the term "salt(s) may include zwitterions (inner salts), e.g., when a compound of formulae I to III contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formulae I to III may be formed, for example, by reacting a compound of the formulae I to III with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

Prodrugs and solvates of the compounds of formulae II and III are also contemplated. The term "prodrug" denotes a compound which, upon administration to a subject, undergoes chemical conversion by metabolic or chemical processes to yield a compound of the formulae II or III, and/or a salt and/or solvate thereof. For example, compounds containing a carboxy group can form physiologically hydrolyzable esters which serve as prodrugs by being hydrolyzed in the body to yield formulae II or III compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formulae II and III include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

The compounds of the formulae I to III, and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. When diastereomeric products are prepared, they can be separated by conventional methods for example, chromatographic or fractional crystallization. The compounds of formulae I to III may be in the free or hydrate form.

Compounds of the formulae II and III may also have prodrug forms. Any compound that will be converted in vivo to provide the bioactive agent (i.e., the compound for formula II) is a prodrug within the scope and spirit of the invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 112, pp. 309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, Vol. 8, pp. 1-38 (1992), each of which is incorporated herein by reference.

It should further be understood that solvates (e.g., hydrates) of the compounds of formulae II and III are also with the scope of the present invention. Methods of solvation are generally known in the art.

The present invention provides a process for preparing a spiro-hydantoin compound represented by formula II

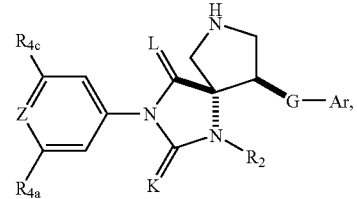

or a pharmaceutically-acceptable salt, hydrate, solvate, or prodrug thereof. This process comprises: contacting alkene compound (I) of formula

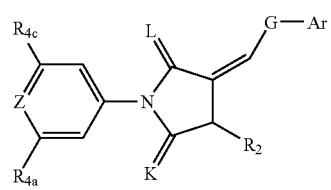

with: i) methylene precursor compound, and
ii) glycine or glycine ester,
in presence of a polar solvent to afford:
the spiro-hydantoin compound (II) or a pharmaceutically-acceptable salt, hydrate, solvate, or prodrug thereof;

wherein:
L and K are independently O or S;
Z is N or $CR_{4b}$;
Ar is aryl, substituted aryl, heteroaryl, or substituted heteroaryl;
G is a bond, —O—, —S—, —$NR_1$, $C_{1-3}$alkylene, $C_{1-3}$substituted alkylene, bivalent alkoxy, thioalkyl, aminoalkyl, sulfonyl, sulfonamidyl, acyl, or alkoxycarbonyl;
$R_1$ is independently hydrogen, alkyl, or substituted alkyl;
$R_2$ is hydrogen, alkyl, substituted alkyl, —$OR_{12}$, —$NR_{12}R_{13}$, —C(=O)$R_{12}$, —$CO_2R_{12}$, —C(=O)$NR_{12}R_{13}$, —$NR_{12}C(=O)R_{13}$, —$NR_{12}C(=O)OR_{13}$, —S(O)$_p R_{13a}$, —$NR_{12}SO_2R_{13a}$, —$SO_2NR_{12}R_{13}$, cycloalkyl, heterocyclo, aryl, or heteroaryl;
$R_{4a}$, $R_{4a'}$, and $R_{4c}$ are independently hydrogen, halogen, alkyl, substituted alkyl, alkenyl, substituted alkenyl, nitro, cyano, —$SR_{14}$, —$OR_{14}$, —$NR_{14}R_{15}$, —$NR_{14}C(=O)R_{15}$, —$CO_2R_{14}$, —C(=O)$R_{14}$, —C(=O)$NR_{14}R_{15}$, aryl, substituted aryl, heterocyclo, substituted heterocyclo, cycloalkyl, substituted cycloalkyl, heteroaryl, and/or substituted heteroaryl;
$R_{12}$, $R_{13}$, $R_{14}$, and $R_{15}$ are independently hydrogen, alkyl, substituted alkyl, cycloalkyl, substituted cycloalkyl, aryl, substituted aryl, heteroaryl, substituted heteroaryl, heterocyclo, and/or substituted heterocyclo; or (ii) $R_{12}$ is taken together with $R_{13}$, or $R_{14}$ is taken together with $R_{15}$ to form a heteroaryl, substituted heteroaryl, heterocyclo, or substituted heterocyclo ring;
$R_{13a}$ is alkyl, substituted alkyl, cycloalkyl, substituted cycloalkyl, aryl, substituted aryl, heteroaryl, substituted heteroaryl, heterocyclo, or substituted heterocyclo; and
p is 1 or 2.

Cycloadditions to alkene isomers are commonly conducted in a nonpolar solvent to minimize conversion between the cis and trans isomers of the alkene starting material, in order to obtain a high yield of product with a particular stereochemistry. Conversion between the cis and trans isomers can occur in the presence of polar solvent leading to the formation of diastereomer mixtures. In the cycloaddition to provide the spiro-hydantoin compound (II), the inventors have discovered that the reaction of the alkene compound (I) and glycine or glycine ester in only nonpolar solvent gave diminishing yields of spiro-hydantoin II as the reaction was scaled to produce larger quantities. Further, reaction yields in only nonpolar solvent were often nonreproducible for a given scale of reaction. However, in the presence of polar solvent, the inventors discovered it was possible to scale the reaction of the alkene compound (I) and glycine to provide a commercially viable process. Further, the inventors have surprisingly discovered that with the use of polar solvent in the present cycloaddition, significant isomerization between the trans isomer to the cis isomer of the alkene compound (I) did not occur. Surprisingly, the present cycloaddition was found to provide a reaction that could be scaled up to pilot plant scale without significant isomerization of the trans isomer to the cis isomer and concomitant loss of the desired diastereomeric product.

In the process of the invention, the alkene compound (I) is contacted with at least one methylene precursor compound, and glycine or glycine ester. The methylene precursor compound serves as a source of a methylene group. The methylene precursor compound may provide the methylene group directly, such as through decomposition of the methylene precursor compound, or indirectly through the formation of an intermediate compound that subsequently forms the methylene group. Examples of methylene precursor compounds include, for example, formaldehyde, dimethoxymethane, trioxane, paraformaldehyde, and hexamethylenetetramine. Formaldehyde may be provided, for example, as a gas, which can be bubbled into the reaction mixture, or as an aqueous formaldehyde solution. A preferred methylene precursor compound is hexamethylenetetramine. Suitable glycine esters include glycine alkyl esters such as glycine methyl ester and glycine ethyl ester. Glycine is preferred.

Alternatively, the methylene precursor compound and the glycine or glycine ester compound may be provided as a condensation product of the methylene precursor compound and the glycine or glycine ester. Examples of suitable condensation products of the methylene precursor compound include:

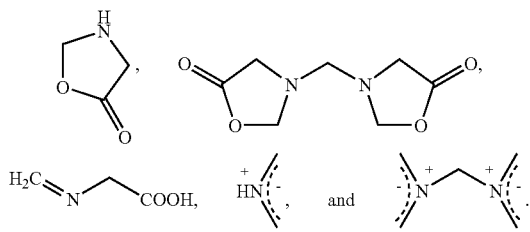

The alkene compound (I) may be contacted with the methylene precursor compound, and the glycine or glycine ester by admixing these ingredients in any order, such as, for example, combining the alkene compound (I) with glycine to form a mixture, and then adding to the methylene precursor compound to the mixture. The alkene compound (I), the methylene precursor compound, and the glycine or glycine ester may be combined prior to reaction, or alternatively, one or more of these ingredients may be gradually added to the reaction mixture during the course of the reaction.

The reaction is conducted in the presence of a polar solvent. As used herein, "polar solvent" refers to a solvent having a dielectric constant of at least 15. Preferably, the polar solvent has a dielectric constant of at least 30. Suitable polar solvents include, for example, acetone, acetonitrile, 1-butanol, 2-butanol, N,N-dimethylacetamide, dimethylformamide, isobutyl alcohol, methanol, 2-methoxyethanol, methylethylketone, 1-methyl-2-pyrrolidinone, 1-propanol, 2-propanol, tetramethyl urea, or mixtures thereof Preferred polar solvents include acetonitrile, N,N-dimethylacetamide, methanol, dimethylformamide, methylethylketone, 1-methyl-2-pyrrolidinone, or mixtures thereof. A more preferred polar solvent is 1-methyl-2-pyrrolidinone. Typically, the reaction may be conducted in a solvent mixture comprising the polar solvent and nonpolar solvent. As used herein, "nonpolar solvent" refers to refers to a solvent having a dielectric constant of less than 15. Preferably, the nonpolar solvent has a dielectric constant of less than 10, and more preferably, less than 5. Suitable nonpolar solvents include, for example, benzene; toluene; or xylene (ortho, meta, para, or a mixture thereof); alkanes such as hexane, heptane, and cyclohexane; and chlorinated solvents such as carbon tetrachloride and chloroform. Mixtures of nonpolar solvent may be employed. Examples of suitable polar/nonpolar solvent mixtures include ratios of polar solvent to nonpolar solvent in the range of about 95:5 to about 5:95, preferably in the range of from about 85:15 to about 45:55, and more preferably in the range of from about 75:25 to about 55:45, based on weight. A preferred polar/nonpolar solvent mixture is 1-methyl-2-pyrrolidinone and toluene in a ratio of about 67:33, based on weight.

Suitable reaction temperatures for this reaction include temperatures in the range of from about 100° C. to about 160° C. The reaction may be conducted in the presence of synthesis adjuvants such as water or metal salts with or without ligands. Preferably, the amount of water in the reaction mixture is minimized. For example, the reaction may be conducted with a reaction mixture that includes less than 3 weight %, preferably less than 2 weight %, and more preferably, less than 1 weight %, based on the weight of the reaction mixture. Techniques to minimize the level of water in the reaction mixture are known in the art, and include removing water from reagents and solvents prior conducting the reaction. The amount of water in the reaction mixture may be determined by Karl Fischer titration. The extent of reaction may be monitored by a suitable technique such as high pressure liquid chromatography (HPLC) or nuclear magnetic resonance detection. Examples of suitable yields of spiro-hydantoin compound (II) include greater than about 50 weight %, preferably greater than about 70 weight %, and more preferably, greater than about 85 weight %.

The process of this invention affords the spiro-hydantoin compound of formula II and, optionally, aminal of the spiro-hydantoin compound of formula II. An aminal has the structure:

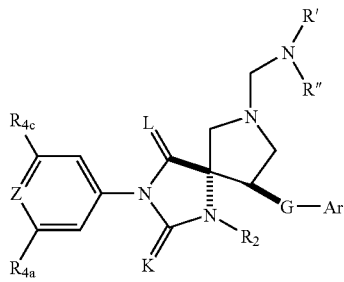

wherein R' and R" represent substituent groups. Optionally R' and R" may be joined to form a ring. In one embodiment, the aminal is an aminal dimer of the spiro-hydantoin compound of formula II and is formed between two molecules of the spiro-hydantoin compound of formula II that are linked together by a methylene bridge between the two ring amines. Examples of aminal dimers of the spiro-hydantoin compound of formula II include the racemic aminal dimer of formula IVa

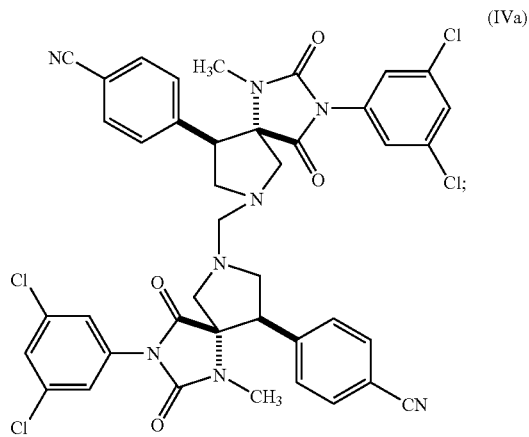

and the meso aminal dimer of formula IVb

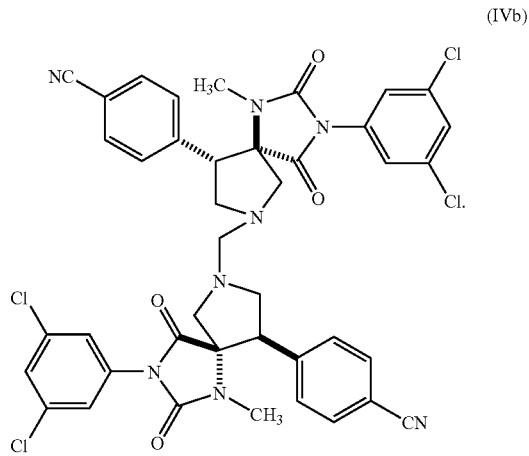

After completion of the reaction, the reaction mixture may contain a mixture of the spiro-hydantoin compound (II) and one or more aminals of the spiro-hydantoin compound (II). The aminal may be cleaved by acidifying the reaction mixture with the addition of an acid such as hydrochloric acid, hydrobromic acid, sulfuric acid, or methanesulfonic acid to afford the spiro-hydantoin compound (II) in greater yield. Another method to cleave the aminal dimer is addition of bisulfite salt. Alternatively, the aminal may be cleaved by treatment with an amine or diamine, for example, ethylene diamine, N-methyl diamine, or propylenediamine. A combination of the aforementioned methods may be employed to cleaved the aminal. The spiro-hydantoin compound (II) may be obtained by cooling the reaction mixture to a temperature below about 30° C., and filtering the spiro-hydantoin compound (II) from the reaction mixture. The resulting spiro-hydantoin compound (II) may be obtained as a salt, for example, as a hydrochloric acid salt; or worked up with an organic solvent and aqueous workup to afford spiro-hydantoin compound (II).

The process of the invention is useful for preparing the spiro-hydantoin compound (II), or enantiomers of the spiro-hydantoin compound (II), represented by spiro-hydantoin compound (IIa)

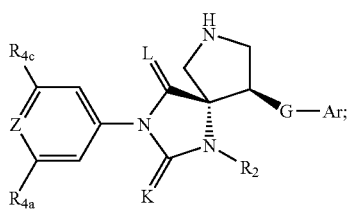

and spiro-hydantoin compound (IIb):

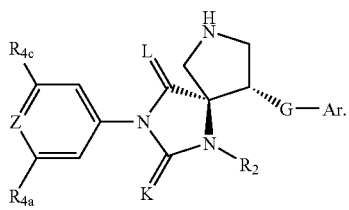

The process of the invention may optionally include a step for separating the enantiomers of spiro-hydantoin compound (II) to provide the individual enantiomers represented by formulae IIa and IIb. The enantiomers of the spiro-hydantoin compound (II) may be resolved from a racemic mixture by various methods known in the art, such as, for example, classical resolution, separation by chiral chromatography such as with a simulating moving bed or HPLC, or enzymatic resolution. In one non-limiting embodiment, the enantiomers of spiro-hydantoin compound. (II) are resolved by contacting the racemic mixture of spiro-hydantoin compound (II) with an enantiomeric acid. Examples of enantiomeric acids include tartaric acid; O-substituted tartaric acid such as (+)-di-p-toluoyl-D-tartaric acid, (+)-di-p-benzoyl-D-tartaric acid, (+)-di-p-o-toluoyl-D-tartaric acid, enantiomers of these acids, or a mixtures thereof. Preferred is (+)-di-p-toluoyl-D-tartaric acid. In this embodiment, the racemic mixture of spiro-hydantoin compound (II) is provided as a mixture in a suitable solvent, such as methyl tertiary butyl ether, methylene chloride, 2-butanone, methyl isobutylketone, or mixture thereof; and contacted with the enantiomeric acid. The resulting mixture is seeded and cooled to allow crystallization of the salt formed by an enantiomer of spiro-hydantoin compound (II) and the corresponding enantiomeric acid. Preferably, the enantiomer is resolved by crystallizing in the presence of alcohol, such as methanol, water, or a combination thereof. The enantiomer IIa or the enantiomer IIb may be employed as a reagent in a subsequent reaction, such as the preparation of a specific enantiomer of the substituted spiro-hydantoin compound of formula III.

In one embodiment, the process of the invention includes the step of reacting the spiro-hydantoin compound of formula II to obtain the substituted spiro-hydantoin compound of formula III:

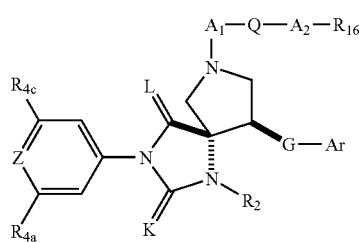

wherein:
  Ar, G, K, L, Z, $R_2$, $R_{4a}$, and $R_{4c}$ are defined hereinabove;
  $A_1$ is a bond, $C_{1-2}$alkylene, or $C_{2-3}$alkenylene;
  Q is a bond, —C(=O)—, —C(=O)NR$_{16}$—, —C(=S)NR$_{16}$—, —SO$_2$—, —SO$_2$NR$_{16}$—, —CO$_2$—, or —NR$_{16}$CO$_2$—;
  $A_2$ is a bond, $C_{1-3}$alkylene, $C_{2-3}$alkenylene, —C$_{1-4}$alkylene-NR$_{16}$—, —C$_{1-4}$alkylene-NR$_d$C(=O)—, —C$_{1-4}$alkylene-S—, —C$_{1-4}$alkylene-SO$_2$—, or —C$_{1-4}$alkylene-O—, wherein the $A_2$ alkylene groups are branched or straight chain, and, optionally, substituted alkylene; and
  $R_{16}$ is hydrogen, alkyl, substituted alkyl, alkenyl, substituted alkenyl, aryl, heteroaryl, heterocyclo, or cycloalkyl, provided that $R_{16}$ is not hydrogen when $A_1$, Q and $A_2$ are each bonds.

In this embodiment, the substituted spiro-hydantoin compound (III) may be prepared by contacting the spiro-hydantoin compound (II) with a halogen containing compound, X-$A_1$-Q-$A_2$-$R_{16}$, where X is a halogen such as chlorine, bromine or iodine, to afford a substituted spiro-hydantoin compound (III). Preferably, X is bromine. The reaction is conducted in a suitable solvent such as, for example, tetrahydrofuran, toluene, isopropyl acetate, isopropanol, or dimethylsulfoxide. Typical reaction temperatures for this reaction are in the range of from about 0° C. to about 30° C. The reaction may be conducted in the presence of synthesis adjuvants such as, for example, an organic base such as triethyl amine, diisopropylethyl amine, or pyridine. The extent of reaction may be monitored by a suitable technique such as high pressure liquid chromatography. After completion of the reaction, the reaction mixture may be cooled to below 30° C. and filtered to obtain the substituted spiro-hydantoin compound (II).

In an optional step, the substituted spiro-hydantoin compound (III) may be resolved into separate enantiomers, represented by formulae IIIa and IIIb

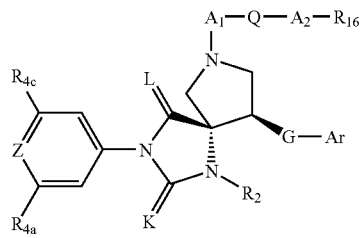

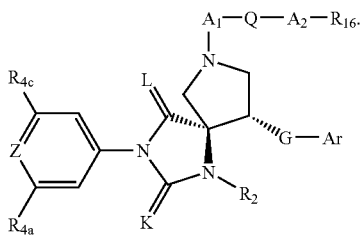

In a further embodiment, the process of this invention may be employed to prepare one of the enantiomers represented by formulae IIIa or IIIb by:
  a) contacting alkene compound (I) with i) methylene precursor compound, and ii) glycine or glycine ester, in presence of a polar solvent to afford spiro-hydantoin compound (II), and, optionally, aminal dimer of the spiro-hydantoin compound (II);
  b) optionally, cleaving the aminal dimer of the spiro-hydantoin compound (II), if present, to afford the spiro-hydantoin compound (II);
  c) resolving the spiro-hydantoin compound (II) into spiro-hydantoin compound (IIa) and spiro-hydantoin compound (IIb); and
  d) contacting either the spiro-hydantoin compound (IIa) or spiro-hydantoin compound (IIb) with a halogen containing compound, X-$A_1$-Q-$A_2$-$R_{16}$ to afford the substituted spiro-hydantoin compound (IIIa) or the substituted spiro-hydantoin compound (IIIb), respectively.

In a different embodiment, the substituted spiro-hydantoin compound (III) may be prepared by contacting the spiro-hydantoin compound (II) with aldehyde containing compound, HC(O)-Q-$A_2$-$R_{16}$ in the presence of a reducing agent, to afford the substituted spiro-hydantoin compound (III) in which $A_1$ is a methylene group, represented by substituted spiro-hydantoin compound (IIIc) of formula:

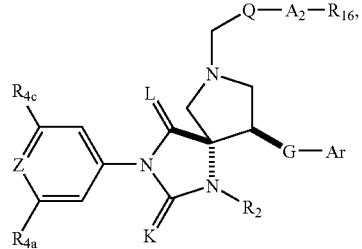

wherein $A_2$, Ar, G, K, L, Q, $R_2$, $R_{4a}$, $R_{4c}$, $R_{16}$, and Z are defined hereinabove. Examples of suitable reducing agents include, but are not limited to, sodium triacetoxy borohydride, sodium cyanoborohydride, and borane-pyridine complex. The reducing agent may be added to the reaction mixture prior to, during, or after the spiro-hydantoin compound (II) is contacted with the aldehyde containing compound. The reaction is conducted in a suitable solvent such as, for example, tetrahydrofuran, toluene, isopropyl acetate, isopropanol, or dimethylsulfoxide. Typical reaction temperatures for this reaction are in the range of from about 0C to about 30° C. The reaction may be conducted in the presence of synthesis adjuvants such as, for example, organic acids such as acetic acid, benzoic acid, or propionic acid. The extent of reaction may be monitored by a suitable technique such as high pressure liquid chromatography. After completion of the reaction and suitable workup, the reaction mixture may be cooled to below 30° C. and filtered to obtain the substituted spiro-hydantoin compound (IIIc).

In an optional step, the substituted spiro-hydantoin compound (IIIc) may be resolved into separate enantiomers, represented by formulae IIId and IIIe

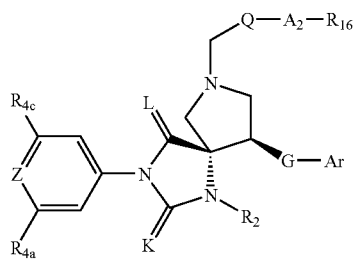

(IIId)

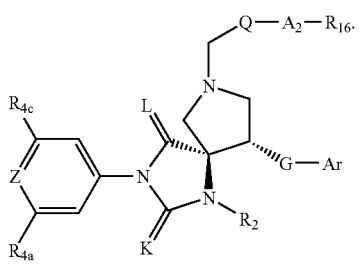

(IIIe)

In a still different embodiment, the process of this invention may be employed to prepare one of the enantiomers represented by formulae IIId or IIIe by:
a) contacting alkene compound (I) with i) methylene precursor compound, and ii) glycine or glycine ester, in presence of a polar solvent to afford spiro-hydantoin compound (II) and, optionally, aminal dimer of the spiro-hydantoin compound (II);
b) optionally, cleaving the aminal dimer of the spiro-hydantoin compound (II), if present, to afford the spiro-hydantoin compound (II);
c) resolving the spiro-hydantoin compound (II) into spiro-hydantoin compound (IIa) and spiro-hydantoin compound (IIb); and
d) contacting either the spiro-hydantoin compound (IIa) or spiro-hydantoin compound (IIb) with an aldehyde containing compound, HC(O)-Q-A$_2$-R$_{16}$ to afford the substituted spiro-hydantoin compound (IIId) or the substituted spiro-hydantoin compound (IIIe), respectively.

In another embodiment, the process of the invention is directed towards the preparation of the spiro-hydantoin compound (II) and, optionally, the substituted spiro-hydantoin compound (III) wherein Z is CR$_{4b}$; K is O; L is O; and Ar, G, R$_2$, R$_{4a}$, R$_{4c}$, A$_1$, A$_2$, Q, and R$_{16}$ are defined hereinabove. The spiro-hydantoin compound (II) of this embodiment has the formula IIf

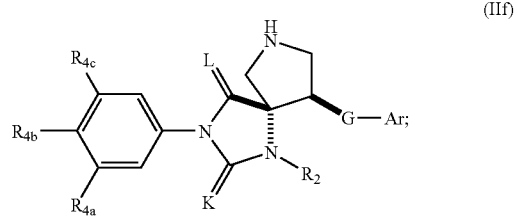

(IIf)

and the substituted spiro-hydantoin compound (III) of this embodiment has the formula IIIf

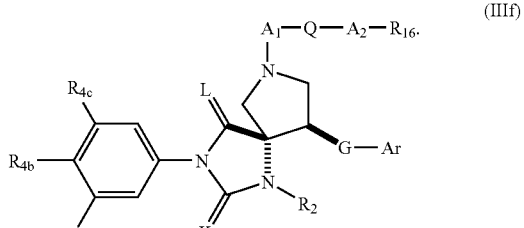

(IIIf)

The spiro-hydantoin compound (IIf) may be optionally resolved to provide either spiro-hydantoin compound (IIg):

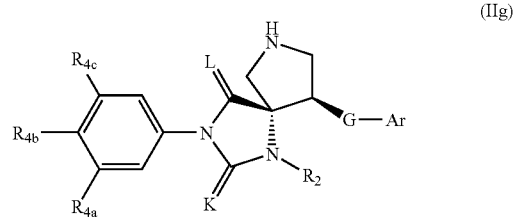

(IIg)

or spiro-hydantoin compound (IIh):

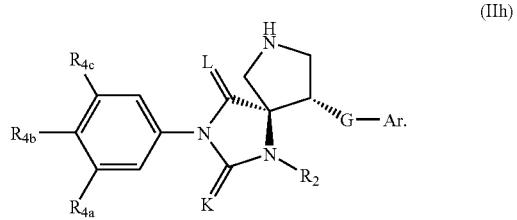

(IIh)

The spiro-hydantoin compounds (IIg) or (IIh) may be employed to prepare substituted spiro-hydantoin compound (IIg):

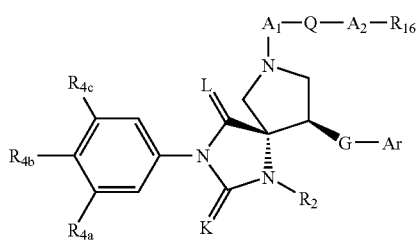

or substituted spiro-hydantoin compound (IIIh),

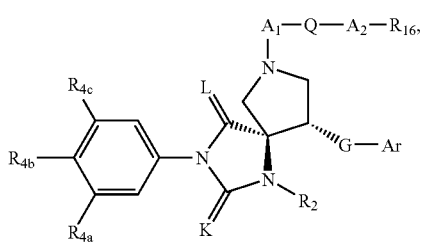

respectively.

In another different embodiment, the process of the invention is directed towards the preparation of the spiro-hydantoin compound (II) and, optionally, the substituted spiro-hydantoin compound (III) wherein: Z is $CR_{4b}$; K is O; L is O; Ar is aryl or substituted aryl; G is a bond, $C_{1-3}$alkylene, or $C_{1-3}$ substituted alkylene; $R_2$ is alkyl or substituted alkyl; and $R_{4a}$, $R_{4c}$, $A_1$, $A_2$, Q, and $R_{16}$ are defined hereinabove.

In a still different embodiment, the process of the invention is directed towards the preparation of the spiro-hydantoin compound (II) and, optionally, the substituted spiro-hydantoin compound (III) wherein: Z is $CR_{4b}$; $R_{4b}$ is H or lower alkyl; K is O; L is O; Ar is substituted aryl; G is a bond or methylene; $R_2$ is alkyl or substituted alkyl; $R_{4a}$ is F, Cl, or Br; $R_{4c}$ is F, Cl, or Br; $A_1$ is alkylene; $A_2$ is a bond; Q is a bond and $R_{16}$ is a heterocyclo or substituted heterocyclo.

In a preferred embodiment, the process of this invention is directed towards the preparation of a substituted spiro-hydantoin compound having the formula IIIm

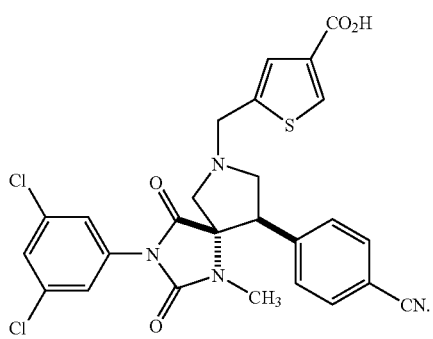

In this embodiment, the substituted spiro-hydantoin compound (IIIm) is prepared by:

a) reacting a methylene precursor compound, and glycine or glycine ester with alkene compound (Ia) of formula

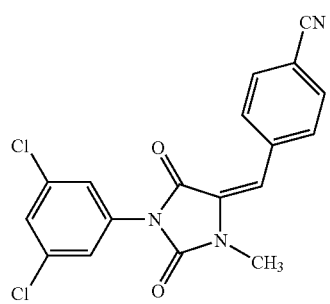

to afford spiro-hydantoin compound (IIc) of formula

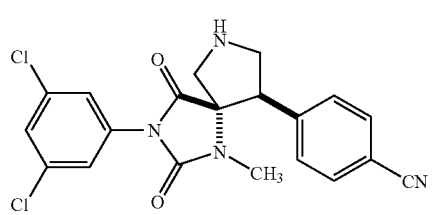

and, optionally, one or more aminal dimers of the spiro-hydantoin compound (IIc) of formula

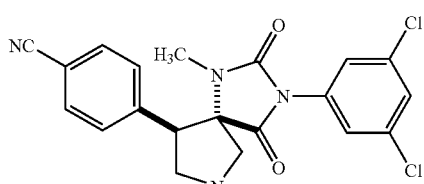

and/or

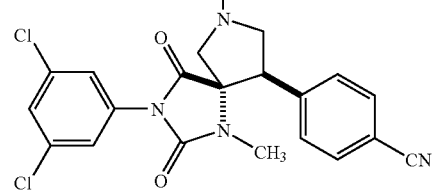

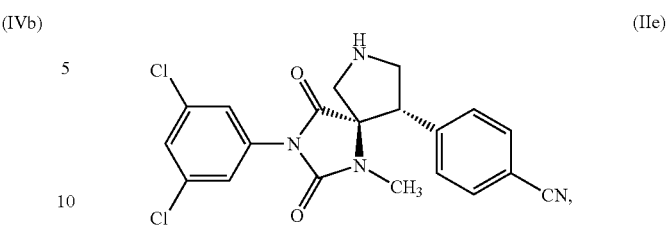

(IVb)

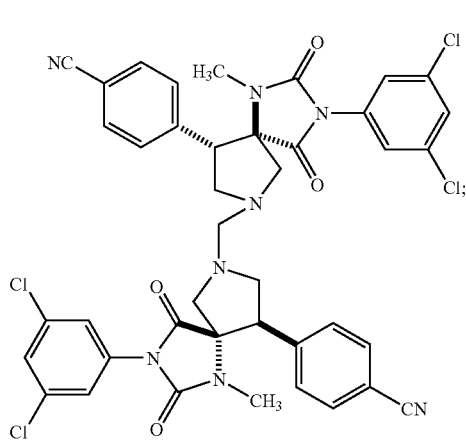

b) optionally, cleaving the one or more aminal dimers of the spiro-hydantoin compound (IIc) to afford the spiro-hydantoin compound (IIc);
c) reacting the spiro-hydantoin compound (IIc) with methyl 5-formylthiophene-3-carboxylate in the presence of a reducing agent, to afford the substituted spiro-hydantoin compound (IIIi)

(IIIi)

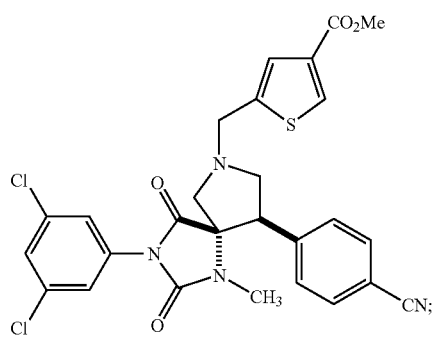

and d) hydrolyzing the methyl ester of the substituted spiro-hydantoin compound (IIIi) to afford the substituted spiro-hydantoin compound (IIIm). Further, the process of this embodiment may include the separation of enantiomers of spiro-hydantoin compound (IIc) to provide spiro-hydantoin compounds (IId) and (IIe):

(IId)

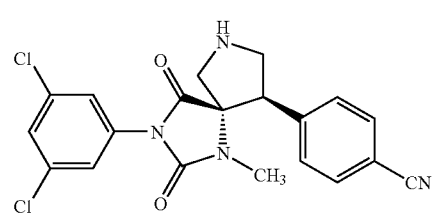

(IIe)

prior to step c, and then in step c, reacting the spiro-hydantoin compound (IId) or the spiro-hydantoin compound (IIe) with methyl 5-formylthiophene-3-carboxylate to afford the respective enantiomer of the substituted spiro-hydantoin compound (IIIi). In step d, the methyl ester of the enantiomer of substituted spiro-hydantoin compound (IIi) is subjected to hydrolysis to afford the respective enantiomer of substituted spiro-hydantoin compound (IIIm), represented by enantiomer IIIn or IIIp, respectively.

(IIIn)

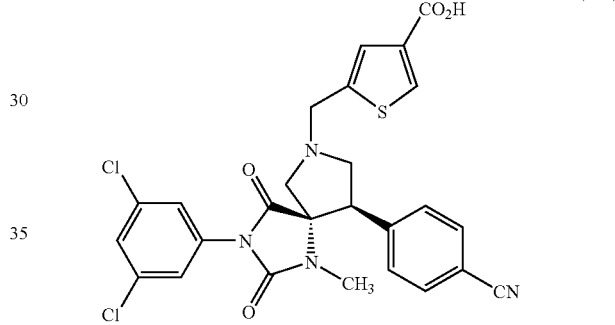

(IIIp)

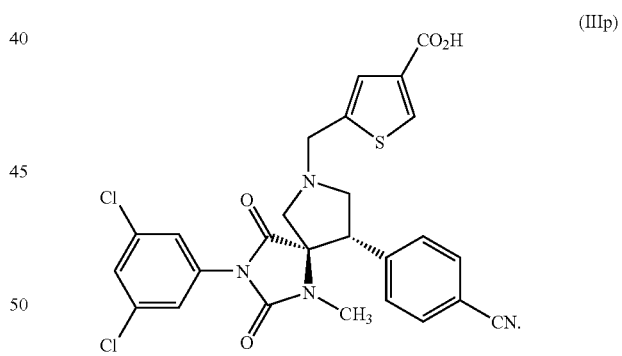

Alternatively, the substituted spiro-hydantoin compound (IIIi) may be resolved to provided the desired enantiomer of the substituted spiro-hydantoin compound (IIIi) prior to the hydrolysis of the methyl ester, to afford the substituted spiro-hydantoin compound (IIIn) or (IIIp). The process of this embodiment is suitable for preparing 5-[(5S,9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid from the (5S,9R) enantiomer of compound (IIc).

The compound (Ia) may be prepared by contacting 4-cyanobenzaldehyde with compound of formula IV:

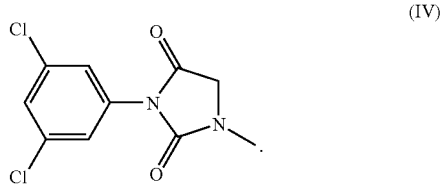

(IV)

For the process of this invention, starting materials are commercially available or can be readily prepared by one of ordinary skill in the art. Solvents, temperatures, pressures, starting materials having the desired groups, and other reaction conditions, may be readily selected as appropriate by one of ordinary skill in the art. The process can be scaled up in order to prepare larger quantities of the spiro-hydantoin compound (II) or the substituted spiro-hydantoin compound (III) or IIIa, such as in a commercial production facility.

Crystalline Forms of 5-[(5S,9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid, and Solvates and Salts Thereof The present invention provides, at least in part, crystalline forms of 5-[(5S,9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid (substituted spiro-hydantoin compound (IIIn)), salts, and solvates thereof.

As used herein "polymorph" refers to crystalline forms having the same chemical composition but different spatial arrangements of the molecules, atoms, and/or ions forming the crystal.

As used herein "solvate" refers to a crystalline form of a molecule and/or ions that further comprises molecules of a solvent or solvents incorporated into the crystalline lattice structure. The solvent molecules in the solvate may be present in a regular arrangement and/or a non-ordered arrangement. The solvate may comprise either a stoichiometric or nonstoichiometric amount of the solvent molecules. For example, a solvate with a nonstoichiometric amount of solvent molecules may result from partial loss of solvent from the solvate. Solvent molecules may occur as dimers or oligomers comprising more than one molecule of solvent within the crystalline lattice structure.

As used herein, "substantially pure," when used in reference to a crystalline form, means a compound having a purity greater than 90 weight %, including greater than 90, 91, 92, 93, 94, 95, 96, 97, 98, and 99 weight %, and also including equal to about 100 weight % of the compound, based on the weight of the compound. The remaining material comprises other form(s) of the compound, and/or reaction impurities and/or processing impurities arising from its preparation. For example, a crystalline form of a compound may be deemed substantially pure in that it has a purity greater than 90 weight % of the crystalline form of that compound, as measured by means that are at this time known and generally accepted in the art, where the remaining less than 10 weight % of material comprises other form(s) of the compound and/or reaction impurities and/or processing impurities. The presence of reaction impurities and/or processing impurities may be determined by analytical techniques known in the art, such as, for example, chromatography, nuclear magnetic resonance spectroscopy, mass spectrometry, or infrared spectroscopy.

As used herein, the unit cell parameter "molecules/unit cell" refers to the number of molecules of the compound in the unit cell.

Samples of the crystalline forms may be provided with substantially pure phase homogeneity, indicating the presence of a dominant amount of a single polymorph and, optionally, minor amounts of one or more other polymorphs. The presence of more than one polymorph in a sample may be determined by techniques such as powder x-ray diffraction (XRPD) or solid state nuclear magnetic resonance spectroscopy. For example, the presence of extra peaks in the comparison of an experimentally measured XRPD pattern with a simulated XRPD pattern may indicate more than one polymorph in the sample. The simulated XRPD may be calculated from single crystal x-ray data. see Smith, D. K., "A FORTRAN Program for Calculating X-Ray Powder Diffraction Patterns," Lawrence RadiationLaboratory, Livermore, Calif., UCRL-7196 (April 1963). Preferably, the crystalline form has substantially pure phase homogeneity as indicated by less than 10%, preferably less than 5%, and more preferably less than 2% of the total peak area in the experimentally measured XRPD pattern arising from the extra peaks that are absent from the simulated XRPD pattern. Most preferred is a crystalline form having substantially pure phase homogeneity with less than 1% of the total peak area in the experimentally measured XRPD pattern arising from the extra peaks that are absent from the simulated XRPD pattern.

Procedures for the preparation of crystalline forms are known in the art. The crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in Solid-State Chemistry of Drugs, S. R. Byrn, R. R. Pfeiffer, and J. G. Stowell, $2^{nd}$ Edition, SSCI, West Lafayette, Ind. (1999).

For crystallization techniques that employ solvent, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility. Suitable solvents for preparing crystals include polar and nonpolar solvents. Examples of solvents for crystallization include, for example, mesitylene, cis-decalin, p-xylene, m-xylene, toluene, n-pentane, n-hexane, n-heptane, n-octane, tetrachloroethene, benzene, n-decane, n-dodecane, carbon disulfide, butylamine, diethyl ether, methyl tertiary-butyl ether, triethylamine, diisopropyl ether, dibutylether, 1,4-dioxane, tetrahydrofuran, chloroform, anisole, o-dichlorobenzene, ethyl formate, trichloroethene, methyl benzoate, iodobenzene, chlorobenzene, methyl ethanoate, dimethyl disulfide, 1,1-dichloroethane, fluorobenzene, ethyl phenyl ether, ethyl acetate, 1,2-dichloroethane, 1,2-dibromoethane, 1-iodobutane, 1,1,1-trichloroethane, propyl ethanoate, diethyl sulfide, dichloromethane, butyl ethanoate, methyl methanoate, bromoform, dibromomethane, m-cresol, 2-methoxyethanol, 1-butanol, propanoic acid, morpholine, 2-methyl-2-propanol, pentanoic acid, acetic acid, 2-propanol, 1-propanol, 1-octanol, ethanol, methyl ethyl ketone, 2,4-dimethylpyridine, acetophenone, 2,6-dimethylpyridine, 3-pentanone, 2-pentanone, 4-methylpyridine, acetone, cyclohexanone, 2-hexanone, cyclopentanone, 2-heptanone, 4-methyl-2-pentanone, 1,3-dimethyl-3,4,5,6-tetrahydro-2(1H)-pyrimidinone, 1,3-dimethyl-2-imidazolidinone, pyrrolidinone, pyridine, N-methyl-2-pyrrolidone, N,N-dimethylformamide, N,N-dimethylacetamide, dimethylsulfoxide, benzonitrile, propanenitrile, acetonitrile, butanenitrile, nitromethane, nitrobenzene, aniline, benzyl alcohol, formic acid, ethylene glycol, methanol, diethylamine, diiodomethane, glycerol, water, formamide, N-methylacetamide, N-methylformamide, methyl acetate, isopropyl acetate, butyl acetate, t-butyl acetate, hexachloroacetone, N,N-dimethylpropionamide, and hexamethylphosphoramide, 2-butanol, t-butyl alcohol, 2-nitroethanol, 2-fluoroethanol, 2,2,2-trifluoroethanol, 2-ethoxyethanol, neo-pentyl alcohol, t-pentyl alcohol, cyclohexanol, and phenol, diethylene glycol, 1-, 2-, or 3-pentanol, 2-methyl-1-propanol, 2-butanol, diethylene glycol monomethyl ether, and methyl t-butyl ether.

In one method to prepare crystals, a compound is suspended and/or stirred in a suitable solvent to afford a slurry, which may be heated to promote dissolution. The term "slurry", as used herein, means a saturated solution of the compound, which may also contain an additional amount of the compound to afford a heterogeneous mixture of the compound and a solvent at a given temperature.

Seed crystals may be added to any crystallization mixture to promote crystallization. Seeding may be employed to control growth of a particular polymorph or to control the particle size distribution of the crystalline product. Accordingly, calculation of the amount of seeds needed depends on the size of the seed available and the desired size of an average product particle as described, for example, in "Programmed Cooling of Batch Crystallizers," J. W. Mullin and J. Nyvlt, *Chemical Engineering Science*, 1971,26, 369-377. In general, seeds of small size are needed to control effectively the growth of crystals in the batch. Seed of small size may be generated by sieving, milling, or micronizing of large crystals, or by micro-crystallization of solutions. Care should be taken that milling or micronizing of crystals does not result in any change in crystallinity form the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid state nuclear magnetic resonance, differential scanning calorimetry, x-ray powder diffraction, or the like, to assure formation of the preferred crystalline form of the product. The resulting crystalline form is typically produced in an amount of greater than about 70 weight % isolated yield, preferably greater than 90 weight % isolated yield, based on the weight of the compound originally employed in the crystallization procedure. The product may be comilled or passed through a mesh screen to delump the product, if necessary.

Crystalline forms may be prepared directly from the reaction medium of the final process for preparing the substituted spiro-hydantoin compound (IIIn). This may be achieved, for example, by employing in the final process step a solvent or a mixture of solvents from which the substituted spiro-hydantoin compound (IIIn) may be crystallized. Alternatively, crystalline forms may be obtained by distillation or solvent addition techniques. Suitable solvents for this purpose include, for example, the aforementioned nonpolar solvents and polar solvents, including protic polar solvents such as alcohols, and aprotic polar solvents such as ketones.

In one aspect of this invention, a crystalline form of the substituted spiro-hydantoin compound (IIIn) is provided. This crystalline form is preferentially a neat crystal and is referred to herein as the "N-1" form, which includes the substituted spiro-hydantoin compound (IIIn) and/or zwitterion thereof.

In one embodiment, the N-1 crystalline form may be characterized by unit cell parameters substantially equal to the following:

| | |
|---|---|
| Cell dimensions: | a = 12.07 Å |
| | b = 17.76 Å |
| | c = 13.12 Å |
| | α = 90.0 degrees |
| | β = 111.9 degrees |
| | γ = 90.0 degrees |
| Space group | P2$_1$ |
| Molecules/unit cell | 2 | wherein the crystalline form is at a temperature of about +22° C.

In a different embodiment, the N-1 crystalline form may be characterized by a powder x-ray diffraction pattern comprising four or more 2θ values (CuKα λ=1.5418 Å) selected from 7.3, 8.5, 8.8, 13.1, 13.7, 15.4, and 17.0, at a temperature of about 22° C. Preferably, the N-1 crystalline form may be characterized by a powder x-ray diffraction pattern comprising five or more 2θ values (CuKα λ=1.5418 Å) selected from 7.3, 8.5, 8.8, 13.1, 13.7, 15.4, and 17.0, at a temperature of about 22° C.

In a still different embodiment, the N-1 crystalline form may be characterized by: fractional atomic coordinates substantially as listed in Table 3.

In a further embodiment, the N-1 crystalline form may be characterized by unit cell parameters substantially equal to the following:

| | |
|---|---|
| Cell dimensions: | a = 12.05 Å |
| | b = 17.72 Å |
| | c = 13.07 Å |
| | α = 90.0 degrees |
| | β = 112.0 |
| | γ = 90.0 degrees |
| Space group | P2$_1$ |
| Molecules/unit cell | 2 | wherein the crystalline form is at a temperature of about −50° C.

In a still further embodiment, the N-1 crystalline form may be characterized by a powder x-ray diffraction pattern comprising four or more 2θ values (CuKα λ=1.5418 Å) selected from 7.9, 8.5, 8.8, 13.1, 15.4, 17.0, and 17.1, at a temperature of about −50° C. Preferably, the N-1 crystalline form may be characterized by a powder x-ray diffraction pattern comprising five or more 2θ values (CuKα λ=1.5418 Å) selected from 7.9, 8.5, 8.8, 13.1, 15.4, 17.0, and 17.1, at a temperature of about −50° C.

In another embodiment, the N-1 crystalline form may be characterized by: fractional atomic coordinates substantially as listed in Table 4.

In a different aspect of the invention, a crystalline form of the substituted spiro-hydantoin compound (IIIn) is provided. This crystalline form is a neat crystal and is referred to herein as "T1E.5-2" form, and includes the substituted spiro-hydantoin compound (IIIn) and/or zwitterion thereof.

In one embodiment, the T1E.5-2 crystalline form may be characterized by unit cell parameters substantially equal to the following:

| Cell dimensions: | a = 11.38 Å |
| --- | --- |
|  | b = 15.22 Å |
|  | c = 31.29 Å |
|  | α = 90.0 degrees |
|  | β = 90.0 degrees |
|  | γ = 90.0 degrees |
| Space group | P2$_1$2$_1$2$_1$ |
| Molecules/unit cell | 2 | wherein the crystalline form is at a temperature of about 90° C.

In a still different aspect of the invention, a crystalline form of a methanesulfonic acid salt of the substituted spiro-hydantoin compound (IIIn) is provided. This crystalline form is a salt formed between methanesulfonic acid and the substituted spiro-hydantoin compound (IIIn), and is referred to herein, as "MSA" form.

In one embodiment, the MSA form may be characterized by unit cell parameters substantially equal to the following:

| Cell dimensions: | a = 8.44 Å |
| --- | --- |
|  | b = 14.67 Å |
|  | c = 25.01 Å |
|  | α = 90.0 degrees |
|  | β = 97.1 degrees |
|  | γ = 90.0 degrees |
| Space group | P2$_1$ |
| Molecules/unit cell | 2 | wherein said crystalline form is at a temperature of about +22° C.

In a different embodiment, the MSA form may be characterized by a powder x-ray diffraction pattern comprising four or more 2θ values (CuKα λ=1.5418 Å) selected from 7.1, 9.3, 10.6, 14.1, 17.0, 21.1, 24.8, and 28.6, at a temperature of about 22° C. Preferably, the MSA form may be characterized by a powder x-ray diffraction pattern comprising five or more 2θ values (CuKα λ=1.5418 Å) selected from 7.1, 9.3, 10.6, 14.1, 17.0, 21.1, 24.8, and 28.6, at a temperature of about 22° C.

In a still different embodiment, the MSA form may be characterized by: fractional atomic coordinates substantially as listed in Table 6.

In another aspect of the present invention, a crystalline form of a hydrochloric acid salt of the substituted spiro-hydantoin compound (IIIn) is provided. This crystalline form is a salt formed between hydrochloric acid and the substituted spiro-hydantoin compound (IIIn), and is referred to herein, as "HCl" form.

In one embodiment, the HCl crystalline form may be characterized by unit cell parameters substantially equal to the following:

| Cell dimensions: | a = 8.26 Å |
| --- | --- |
|  | b = 12.56 Å |
|  | c = 13.22 Å |
|  | α = 90.0 degrees |
|  | β = 90.2 degrees |
|  | γ = 90.0 degrees |
| Space group | P2$_1$ |
| Molecules/unit cell | 1 | wherein said crystalline form is at a temperature of about +22° C.

In a different embodiment, the HCl crystalline form may be characterized by a powder x-ray diffraction pattern comprising four or more 2θ values (CuKα λ=1.5418 Å) selected from 9.7, 12.8, 14.1, 14.5, 18.6, 19.0, 21.4, 23.8, and 26.7, at a temperature of about 22° C. Preferably, the HCl crystalline form may be characterized by a powder x-ray diffraction pattern comprising five or more 2θ values (CuKα λ=1.5418 Å) selected from 9.7, 12.8, 14.1, 14.5, 18.6, 19.0, 21.4, 23.8, and 26.7, at a temperature of about 22° C.

In a still different embodiment, the HCl crystalline form may be characterized by: fractional atomic coordinates substantially as listed in Table 5.

In a further aspect of the present invention, a crystalline form, which optionally comprises solvent, is provided. These forms include solvates of the substituted spiro-hydantoin compound (IIIn) or zwitterion thereof. In one embodiment, these forms may be characterized by unit cell parameters substantially equal to the following:

| Volume is in the range of from about 5300 to about 5800 Å$^3$; |  |
| --- | --- |
| Space group | P2$_1$2$_1$2$_1$; |
| Z = 8; |  | and, optionally, comprising solvent. In a further embodiment, this crystalline form further comprises solvent, wherein the solvent is methanol, ethanol, n-propanol, iso-propanol, acetonitrile, N-methylpyrrolidinone, or tetrahydrofuran. In still further embodiment, the crystalline form comprises an asymmetric unit of 2 molecules of the substituted spiro-hydantoin compound (IIIn) or zwitterion thereof, and one molecule of said solvent. These crystalline forms may be characterized by unit cell parameters substantially equal to the following:

| Cell dimensions: | a is in the range of from about 11.1 to about 11.4 Å; |
| --- | --- |
|  | b is in the range of from about 14.9 to about 16.0 Å; |
|  | c is in the range of from about 31.4 to about 32.8 Å; |
|  | volume is in the range of from about 5300 to about 5800 Å$^3$; |
| Space group | P2$_1$2$_1$2$_1$ |
| Molecules/unit cell | 2 |

Density (calculated) (g/cm$^3$) is in the range of from about 1.380 to about 1.420; wherein said crystalline form is at a temperature of about −50° C.

In a different aspect of the present invention, a crystalline form of the mono isopropanol solvate of 4-[(5S*,9R*)-3-(3,5-Dichlorophenyl)-1-methyl-2,4-dioxo-1,3,7-triazaspiro[4.4]non-9-yl]-benzonitrile is provided. This crystalline form is referred to herein as the "IPA-1", which comprises the spiro-hydantoin compound (IIc) and isopropanol.

In one embodiment, the IPA-1crystalline form of spiro-hydantoin compound (IIc) may be characterized by unit cell parameters substantially equal to the following:

| Cell dimensions: | a = 9.93 Å |
| --- | --- |
|  | b = 10.76 Å |
|  | c = 12.80 Å |
|  | α = 111.7 degrees |
|  | β = 89.8 degrees |
|  | γ = 107.6 degrees |
| Space group | P-1 |
| Molecules/unit cell | 1 | wherein said crystalline form is at a temperature of about −50° C.

In a different embodiment, the IPA-1crystalline form of the spiro-hydantoin compound (IIc) may be characterized by: fractional atomic coordinates substantially as listed in Table 19.

In a still different aspect of the present invention, crystalline forms of the aminal dimer of 4-[3-(3,5-Dichlorophenyl)-1-methyl-2,4-dioxo-1,3,7-triazaspiro[4.4]non-9-yl]-benzonitrile are provided.

In one embodiment, a crystalline form comprising the meso aminal dimer, Compound (IVb), and methyl tertiary butyl ether is provided, and is referred to herein as the "MTBE2-1" form. The crystalline form comprises an asymmetric unit of one molecule of Compound (IVb) and two molecules of the methyl tertiary butyl ether solvent.

In a different embodiment, the MTBE2-1crystalline form may be characterized by unit cell parameters substantially equal to the following:

| Cell dimensions: | a = 10.22 Å |
| --- | --- |
|  | b = 11.51 Å |
|  | c = 22.23 Å |
|  | α = 85.4 degrees |
|  | β = 86.0 degrees |
|  | γ = 87.6 degrees |
| Space group | P-1 |
| Molecules/unit cell | 1 | wherein said crystalline form is at a temperature of about −50° C.

In a still different embodiment, the MTBE2-1crystalline form of the meso aminal dimer may be characterized by a powder x-ray diffraction pattern comprising four or more 2θ values (CuKα λ=1.5418 Å) selected from 8.0, 9.8, 11.4, 16.3, 17.3, 20.0, and 23.5, at a temperature of about −50° C. Preferably, the MTBE2-1crystalline form may be characterized by a powder x-ray diffraction pattern comprising five or more 2θ values (CuKα λ=1.5418 Å) selected from 8.0, 9.8, 11.4, 16.3, 17.3, 20.0, and 23.5, at a temperature of about −50° C.

In a still different embodiment, the MTBE2-1crystalline form of the meso aminal dimer may be characterized by: fractional atomic coordinates substantially as listed in Table 21.

In further embodiment, a crystalline form comprising the racemic aminal dimer, Compound (IVa), and acetonitrile is provided, and is referred to herein as the "AN1.5-1" form. The crystalline form comprises an asymmetric unit of one molecule of Compound (IVa) and two molecules of the methyl tertiary butyl ether solvent.

In still further embodiment, the AN1.5-1crystalline form may be characterized by unit cell parameters substantially equal to the following:

| Cell dimensions: | a = 13.33 Å |
| --- | --- |
|  | b = 17.95 Å |
|  | c = 19.13 Å |
|  | α = 85.2 degrees |
|  | β = 83.3 degrees |
|  | γ = 83.1 degrees |
| Space group | P-1 |
| Molecules/unit cell | 2 | wherein said crystalline form is at a temperature of about −50° C.

In another further embodiment, the AN1.5-1crystalline form of the racemic aminal dimer may be characterized by a powder x-ray diffraction pattern comprising four or more 2θ values (CuKα λ=1.5418 Å) selected from 5.0, 9.4, 11.4, 12.1, 18.8, 21.2, 22.3, and 26.8, at a temperature of about −50° C. Preferably, the AN1.5-1crystalline form may be characterized by a powder x-ray diffraction pattern comprising five or more 2θ values (CuKα λ=1.5418 Å) selected from 5.0, 9.4, 11.4, 12.1, 18.8, 21.2, 22.3, and 26.8, at a temperature of about −50° C.

In a different embodiment, the AN1.5-1crystalline form of the aminal dimer may be characterized by: fractional atomic coordinates substantially as listed in Table 22.

UTILITY

Crystalline forms of formula IIIn, including salts and solvates thereof, prepared by any process, including the instant inventive process, are antagonists and/or inhibitors of LFA-1, Mac-1, and/or ICAMs. Additionally, the substituted spiro-hydantoins, including salts and solvates thereof, that are prepared via the present inventive process that are generally described by formula III, are antagonists and/or inhibitors of LFA-1, Mac-1, and/or ICAMs. Both the aforementioned compounds, the crystalline forms of formula IIIn (and salts and solvates, thereof) made by any process, and the substituted spiro-hydantoin compounds made by the present inventive process (their salts and solvates thereof) are hereinafter referred to as the "compounds" or the "inventive compounds".

The present inventive compounds have utility in treating various inflammatory diseases and disorders associated with the action of LFA-1, Mac-1, and/or ICAMs, particularly LFA-1:ICAM-1. The term "Leukointegrin/ICAM-associated condition" is used herein for ease of reference to refer to those diseases or disorders that are associated with the action or levels of LFA-1, Mac-1 and/or ICAM-1, ICAM-2, or ICAM-3. As used herein, the term "treating" includes prophylactic and therapeutic uses and thus includes the alleviation of symptoms of a Leukointegrin/ICAM-associated condition in a patient, the improvement of an ascertainable measurement associated with such a condition, or the prevention of such a condition or its symptoms. The term "patient" refers to a mammal, preferably a human.

In view of their inhibition activity, the inventive compounds may be used to treat conditions involving the activation, co-stimulation, or infiltration of T-cells and/or leukocytes, including without limitation, conditions involving the influx of leukocytes in the skin, peritoneum, synovium, lung, kidney, and heart. These compounds may be used to treat conditions resulting from a response of the specific or non-specific immune system in a patient.

Leukointegrin/ICAM-associated conditions that may be treated with the instant inventive compounds include acute or chronic graft vs host reactions (e.g., pancreatic islet allograft); and acute or chronic transplant rejection (e.g., kidney, liver, heart, lung, pancreas, bone marrow, cornea, small bowel, skin allografts, skin homografts, heterografts, and/or cells derived from such organs). Additionally, these compounds may be useful in treating inflammatory conditions including, but not limited to, multiple sclerosis, rheumatoid arthritis, psoriatic arthritis, osteoarthritis, osteoporosis, diabetes (e.g., insulin dependent diabetes mellitus or juvenile onset diabetes), cystic fibrosis, inflammatory bowel disease, irritable bowel syndrome, Crohn's disease, ulcerative colitis, Alzheimer's disease, shock, ankylosing spondylitis, gastritis, conjunctivitis, pancreatis (acute or chronic), multiple organ injury syndrome (e.g., secondary to septicemia or trauma), myocardial infarction, atherosclerosis, stroke, reperfusion injury (e.g., due to cardiopulmonary bypass or kidney dialysis), acute glomerulonephritis, vasculitis, thermal injury (i.e., sunburn), necrotizing enterocolitis, granulocyte transfusion associated syndrome, and/or Sjogren's syndrome.

The instant inventive compounds may be used in treating inflammatory conditions of the skin. Such conditions include, without limit, eczema, atopic dermatitis, contact dermatitis, urticaria, schleroderma, psoriasis, and dermatosis with acute inflammatory components.

The present inventive compounds, may also be used in treating allergies and respiratory conditions. Such conditions include, without limit, asthma, pulmonary fibrosis, allergic rhinitis, oxygen toxicity, emphysema, chronic bronchitis, acute respiratory distress syndrome, and any chronic obstructive pulmonary disease (COPD).

The present inventive compounds may be useful in treating hepatitis infection, including hepatitis B and hepatitis C.

Further, the inventive compounds may be useful in treating autoimmune diseases and/or inflammation associated with autoimmune diseases. Such diseases include, without limit, organ-tissue auto immune diseases (e.g., Raynaud's syndrome), autoimmune thyroiditis, uveitis, systemic lupus erythematosis, Addison's disease, autoimmune polyglandular disease (also known as autoimmune polyglandular syndrome), and Grave's disease.

The instant inventive compounds may be useful in treating metastases or as an adjunct to minimize toxicity with cytokine therapy in the treatment of cancers.

The present inventive compounds may be useful in treating a number of conditions These conditions include, without limit, hypogonadism, frailty, sexual dysfunction, wasting, such as wasting syndromes associated with cancer and AIDS, and anemia. These compounds further have utility in treating cancers, including but not limited to cancers of the breast, brain, skin, ovary, endometrium, bladder, prostate, lung, colon, lymphatic system, liver and kidney. Other conditions include, without limit, hirsutism, acne, seborrhea, alopecia, fibroids, hyperpilosity, cachexia, polycystic ovarian syndrome, anorexia, contraception, drug withdrawal syndrome, pregnancy termination, and benign prostate hypertrophy. The aforementioned compounds may also be useful as antiangiogenic agents, as well as being useful as inhibitors of protein prenyltransferases, particularly farnesyltransferase and the prenylation of the oncogene protein Ras. Accordingly, these compounds may be useful for treating and/or preventing the diseases and disorders referred to in WO 01/45704, incorporated herein by reference.

In summary, the present inventive compounds may be particularly useful in treating acute or chronic graft vs host reactions, acute or chronic transplant rejection, multiple sclerosis, rheumatoid arthritis, psoriatic arthritis, osteoarthritis, osteoporosis, diabetes, cystic fibrosis, inflammatory bowel disease, irritable bowel syndrome, Crohn's disease, ulcerative colitis, Alzheimer's disease, shock, ankylosing spondylitis, gastritis, conjunctivitis, pancreatis, multiple organ injury syndrome, myocardial infarction, atherosclerosis, stroke, reperfusion injury, acute glomerulonephritis, vasculitis, thermal injury, necrotizing enterocolitis, granulocyte transfusion associated syndrome, Sjogren's syndrome, eczema, atopic dermatitis, contact dermatitis, urticaria, schleroderma, psoriasis, asthma, pulmonary fibrosis, allergic rhinitis, oxygen toxicity, emphysema, chronic bronchitis, acute respiratory distress syndrome, chronic obstructive pulmonary disease (COPD), hepatitis B, hepatitis C, organ-tissue autoimmune disease, autoimmune thyroiditis, uveitis, systemic lupus erythematosis, Addison's disease, autoimmune polyglandular disease, and Grave's disease. The present inventive compounds may be even more particularly useful in treating acute or chronic transplant rejection, rheumatoid arthritis, osteoarthritis, diabetes, asthma, inflammatory bowel disease, psoriasis, and chronic obstructive pulmonary disease.

When used as anti-inflammatory agents, the present inventive compounds may be administered prior to the onset of, at, or after the initiation of inflammation. When used prophylactically, these compounds are preferably provided in advance of any inflammatory response or symptom (for example, prior to, at, or shortly after the time of an organ or tissue transplant but in advance of any symptoms of organ rejection). Administration of the compounds may prevent or attenuate inflammatory responses or symptoms.

The present invention also provides pharmaceutical compositions capable of treating the above-referenced diseases and disorders, The inventive compositions may optionally contain other therapeutic agents and may be formulated with at least one pharmaceutically acceptable carrier or diluent. Such a formulation may employ, for example, conventional solid or liquid vehicles or diluents, as well as pharmaceutical additives of a type appropriate to the mode of desired administration (for example, excipients, binders, preservatives, stabilizers, flavors, etc.), according to techniques such as those well known in the art of pharmaceutical formulation.

The instant inventive compounds may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular, or intrasternal injection or infusion techniques (e.g., as sterile injectable aqueous or nonaqueous solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal administration via aerosol or inhalation include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a patient of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and the particular condition sought to be treated and its severity. Preferred subjects for treatment include animals, most preferably mammalian species such as humans, and domestic animals such as dogs, cats, horses, and the like, subject to Leukointegrin/ICAM associated conditions and/or subject to any of the above-referenced diseases and disorders.

The inventive compounds and compositions may be employed alone or in combination with each other and/or other suitable therapeutic agents useful in treating diseases and disorders referenced above, for example, where the second drug has the same or different mechanism of action than the present compounds. Exemplary of such other therapeutic agents include anti-inflammatory agents, antibiotics, anti-viral agents, anti-oxidants, and agents used to treat respiratory conditions such as COPD and asthma.

Examples of suitable other anti-inflammatory agents with which the inventive compounds may be used include aspirin, cromolyn, nedocromil, theophylline, zileuton, zafirlukast, montelukast, pranlukast, indomethacin, and lipoxygenase inhibitors; non-steroidal antiinflammatory drugs (NSAIDs) (such as ibuprofen and naproxin); TNF-α inhibitors (such as tenidap and rapamycin or derivatives thereof), or TNF-α antagonists (e.g., infliximab, Enbrel®, D2E7, OR1384), cytokine modulators (e.g. TNF-alpha converting enzyme [TACE] inhibitors, Interleukin-1 converting enzyme (ICE) inhibitors, Interleukin-1 receptor antagonists), prednisone, dexamethasone, cyclooxygenase inhibitors (i.e., COX-1 and/or COX-2 inhibitors such as Naproxen®, Celebrex®, or Vioxx®), CTLA4-Ig agonists/antagonists (LEA29Y), CD40 ligand antagonists, IMPDH inhibitors (such as mycophenolate [CellCept®] and VX-497), methotrexate (FK506), integrin antagonists (e.g., alpha-4 beta-1, alpha-V-beta-3), cell adhesion inhibitors, interferon gamma antagonists, prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, therapies for the treatment of irritable bowel syndrome (e.g., Zelmac®, Zelnorm®, and Maxi-K® openers such as those disclosed in U.S. Pat. No. 6,184,231 B1), or NF-κB inhibitors (such calphostin, CSAIDs, and quinoxalines as disclosed in U.S. Pat. No. 4,200,750); disassociated steroids; chemokine receptor modulators (including CCR1, CCR2, CCR3, CCR4, and CXCR2 receptor antagonists); secretory and cytosolic phospholipase A2 inhibitors, glucocorticoids, salicylates, nitric oxide, and other immunosuppressants; and nuclear translocation inhibitors, such as deoxyspergualin (DSG).

The inventive compounds may be used in combination with other agents used to treat respiratory conditions such as asthma, COPD, and allergic rhinitis, such as β-adrenergic agonists (such as albuterol, terbutaline, formoterol, salbutamol, salmeterol, bitolterol, pilbuterol, and fenoterol); corticosteroids (such as beclomethasone, triamcinolone, budesonide, fluticasone, flunisolide, dexamethasone, prednisone, and dexamethasone); leukotriene antagonists (e.g., Accolate [Zafirlukast®], and Singulair [Montelukast®]); Muscarinic M3 cholinergic antagonists (e.g., Spiriva®), PDE 4 inhibitors (e.g. rolipram, cilomilast [Ariflo®], piclamilast, or roflumilast), histamine $H_1$ antagonists, Allegra® (fexofenadine), Claritin® (loratidine), and/or Clarinex® (desloratidine).

Examples of suitable antiviral agents for use with the inventive compounds include nucleoside-based inhibitors, protease-based inhibitors, and viral-assembly inhibitors.

Examples of suitable anti-osteoporosis agents for use in combination with the compounds of the present invention include alendronate, risedronate, PTH, PTH fragment, raloxifene, calcitonin, RANK ligand antagonists, calcium sensing receptor antagonists, TRAP inhibitors, selective estrogen receptor modulators (SERM) and AP-1inhibitors.

Examples of suitable anti-oxidants for use in combination with the compounds of the present invention include lipid peroxidation inhibitors such as probucol, BO-653, Vitamin A, Vitamin E, AGI-1067, and α-lipoic acid.

The inventive compounds also may be used in combination with anti-diabetic agents, such as biguanides (e.g. metformin), glucosidase inhibitors (e.g. acarbose), insulins (including insulin secretagogues or insulin sensitizers), meglitinides (e.g. repaglinide), sulfonylureas (e.g., glimepiride, glyburide and glipizide), biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1(GLP-1), glucagon phosphorylase, and dipeptidyl peptidase IV (DP4) inhibitors.

In addition, the inventive compounds may be used with agents that increase the levels of cAMP or cGMP in cells for a therapeutic benefit. For example, the compounds of the invention may have advantageous effects when used in combination with phosphodiesterase inhibitors, including PDE1inhibitors (such as those described in Journal of Medicinal Chemistry, Vol. 40, pp. 2196-2210 [1997]), PDE2 inhibitors, PDE3 inhibitors (such as revizinone, pimobendan, or olprinone), PDE4 inhibitors (referenced above), PDE7 inhibitors, or other PDE inhibitors such as dipyridamole, cilostazol, sildenafil, denbutyline, theophylline (1,2-dimethylxanthine), ARIFLO™ (i.e., cis-4-cyano-4-[3-(cyclopentyloxy)-4-methoxyphenyl]cyclohexane-1-carboxylic acid), arofyline, C-11294A, CDC-801, BAY-19-8004, cipamfylline, SCH351591, YM-976, PD-189659, mesiopram, pumafentrine, CDC-998, IC-485, and KW-4490.

In view of their usefulness in treating ischemia, the inventive compounds may be used in combination with agents for inhibiting $F_1F_0$-ATPase, including efrapeptin, oligomycin, autovertin B, azide, and compounds described in U.S. patent application Ser. No. 60/339,108, filed Dec. 10, 2001 and assigned to the present assignee; -alpha- or beta-adrenergic blockers (such as propranolol, nadolol, carvedilol, and prazosin), antianginal agents such as nitrates, for example, sodium nitrates, nitroglycerin, isosorbide mononitrate, isosorbide dinitrate, and nitrovasodilators; antiarrhythmic agents including Class I agents (such as propafenone); Class II agents (propranolol); Class III agents (such as sotalol, dofetilide, amiodarone, azimilide and ibutilide); Class IV agents (such as ditiazem and verapamil); $K^+$ channel modulators such as $I_{Ach}$ inhibitors and inhibitors of the $K_v1$ subfamily of $K^+$ channel openers such as $I_{Kur}$ inhibitors (e.g., compounds disclosed in U.S. application Ser. No. 09/729,731, filed Dec. 5, 2000); and gap-junction modulators such as connexions; anticoagulant or antithrombotic agents including aspirin, warfarin, ximelagtran, low molecular weight heparins (such as lovenox, enoxaparain, and dalteparin), anti-platelet agents such as GPIIb/GPIIIa blockers, (e.g., abciximab, eptifibatide, and tirofiban), thromboxane receptor antagonists (e.g., ifetroban), $P2Y_1$ and $P2Y_{12}$ antagonists (e.g., clopidogrel, ticlopidine, CS-747, and aspirin/clopidogrel combinations), and Factor Xa inhibitors (e.g., fondaprinux); and diuretics such as sodium-hydrogen exchange inhibitors, chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, and amiloride.

The inventive compounds may also be useful in combination with antiangiogenic agents, such as compounds that are inhibitors of VEGF receptors, or in conjunction with antitumor agents such as paclitaxel, adriamycin, epothilones, cisplatin, and carboplatin. Examples of anticancer and other cytotoxic agents that may be used in combination with the inventive compounds include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416; and prenyl-protein transferase inhibitors as found in WO 97/30992 and WO 98/54966.

The combination of the inventive compounds with other therapeutic agents may prove to have additive and synergistic effects. The combination may be advantageous to increase the efficacy of the administration or decrease the dosage to reduce possible side-effects.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The present inventive compounds, including the substituted spiro-hydantoin compounds described in the examples herein, have been tested in assay(s) described below and have shown a measurable level of activity as inhibitors of LFA-1and/or ICAM-1.

ASSAYS

H1-Hela Adhesion Assay

H1-Hela cells were released from their growth flask using versene (Gibco, Grand Island, N.Y.). Following centrifugation, the cells were resuspended in growth medium: DMEM (Gibco), 10% fetal calf serum (Hyclone, Logan, Utah), 1% Pen-Strep (Gibco), and 1% L-glutamine (Gibco) and plated for growth at 5,000 cells/well in a 96-well plate.

The next day, HSB-2 cells were divided to $2 \times 10^5$/ml in growth medium: RPMI 1640 (Gibco), 10% FCS, 1% Pen-Strep, and 1% L-glutamine. The next day (day #3), the cells were centrifuged at 534×G for 8 minutes, washed, and resuspended in HBSS at $5 \times 10^7$/ml. Calcein-AM, 10 μM (Molecular Probes, Eugene, Oreg.) and 100 nM phorbol myristate acetate (SIGMA, St. Louis, Mo.) were added to the labeling and activation mix. Following incubation at 37°

C. for 30 minutes, ten ml of HBSS was added and the cells centrifuged as above. The cell pellet was then resuspended and counted.

While the HSB-2 cells were labeling, the medium was aspirated from the H1-HeLa cells and the plates washed once with HBSS, followed by the addition of 50 µl of HBSS. An additional 50 µl of HBSS containing compound solution, DMSO, or anti-CD18 antibody was then added to each well. To the H1-HeLa cells were added 200,000 HSB-2 cells/well in 100 µl, followed by incubation in the dark for 30 minutes. The wells were then washed three times to remove the unbound cells. A fluorescence plate reader was then used to determine the number of bound HSB-2 cells. The percent inhibition due to the compound was calculated using the vehicle control as 0% inhibition and the antibody blocked adhesion as 100% inhibition.

Huvec Adhesion Assay

On day 1, human umbilical vein endothelial cells (HUVEC) (passage 3, Clonetics, San Diego, Calif.) were placed into a T-75 flask containing EGM bulletkit media (Clonetics) for growth.

When the HUVEC were 90% confluent (typically day 4), 96-well tissue culture plates were coated with 100 µl/well of 2.5 µg/ml mouse Type IV collagen (Trevigen) diluted in 0.1 M acetic acid. Following incubation for at least three hours, the collagen was removed and the plate washed three times with HBSS (Gibco). The HUVEC flask was trypsinized, and HUVEC were plated on the collagen coated wells at 1250 cells/200 µl/well for use four days later. Twenty hours prior to use, the medium was removed and cells were stimulated with 200 µl of 10 nM phorbol myristate acetate (PMA, Sigma, St. Louis, Mo.) in EGM. When the cells were 90% confluent (typically day 8), the PMA-containing medium was removed, the wells were washed with HBSS, and 50 µl of HBSS was added-to the wells. An additional 50 µl containing compound solution, DMSO or blocking anti-CD18 was then added to each well.

On day 7, HSB-2 cells were then divided to 2×10$^5$/Ml in RPMI 1640 (Gibco), 10% FCS (Hyclone, Logan, Utah), 1% Pen-Strep (Gibco), and 1% L-glutamine (Gibco). The following day, the cells were centrifuged at 534×G for 8 minutes, washed, and resuspended in HBSS at 5×10$^7$/ml. For activation and labeling, calcein-AM, 10 µM (Molecular Probes, Eugene, Oreg.) and 100 nM phorbol myristate acetate (Sigma, St. Louis, Mo.) were added and the cells incubated at 37° C. for 30 minutes. Following the addition of ten ml of HBSS, the cells were centrifuged, resuspended, and counted.

To the HUVEC cells were added 200,000 labeled and activated HSB-2 cells/well in 100 µl, followed by incubation in the dark for 30 minutes. To remove unbound cells, the wells were washed three times with HBSS. A fluorescence plate reader was used to determine the number of HSB-2 cells bound. The percent inhibition due to the compound was calculated with the vehicle control set at 0% inhibition and the antibody-blocked adhesion set at 100% inhibition.

EXAMPLES

The following examples illustrate embodiments of the inventive process, and are not intended to limit the scope of the claims. For ease of reference, the following abbreviations are used herein:

ABBREVIATIONS

DMSO=dimethyl sulfoxide
DTTA=(+)-Di-p-toluoyl-D-tartaric acid
EtOH=ethanol
HCl=hydrochloric acid
HPLC=high performance liquid chromatography
kg=kilogram
L=liter
M=molar
MTBE=methyl tertiary butyl ether
MeOH=methanol
mol=mole
mp=melting point
NMR=nuclear magnetic resonance
TBME=t-butyl methyl ether
THF=tetrahydrofuran Preparation 1

3-(3,5-dichlorophenyl)-1-methylimidazolidine-2,4-dione

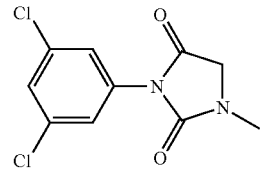

Triethylamine (0.78 kg, 7.75 mol) was added in 15-30 minutes with stirring to a thin suspension of sarcosine ethylene hydrochloride (1.00 kg, 6.51 mol) in dichloromethane (6.00 L). After stirring at room temperature for 1.5-2.0 hours, the mixture was filtered to remove the resulting triethylamine hydrochloride salt. The salt cake was washed with dichloromethane (2.00 L). The filtrate was cooled to 0-5° C.

A solution of 3,5-dichlorophenyl isocyanate (1.47 kg, 7.81 mol) in dichloromethane was prepared at 20-25° C. The solution was added to the above cooled filtrate slowly in 30-60 minutes. The temperature was maintained below 10° C. during the addition. After the addition, the mixture was stirred at 20-25° C. for 12-14 hours. The completeness of the reaction was followed by HPLC. Upon reaction completion, TBME (16.00 L) was added in one portion. The resulting suspension was stirred at 20-25° C. for 2-3 hours and was then filtered. The filter cake was washed with TBME (4.50 L) and dried at maximum 40° C. to a constant weight. A suspension of the above filter cake in water (17.0 L, 10 L/kg input) was prepared and stirred at 20-25° C. for at least 16 hours. The suspension was filtered and the filter cake was washed with water (3×1.36 L) and dried at maximum 40° C. to a constant weight to a constant weight. 3-(3,5-dichlorophenyl)-1-methylimidazolidine-2,4-dione (1.52 kg, 90%) was obtained as a white crystalline solid. mp=202-204° C. $^1$H NMR (DMSO-d$_6$): 7.66 (1H, m), 7.51 (2H, m), 4.10 (2H, s), 3.35 (3H, s). $^{13}$C NMR (DMSO-d$_6$): 8 Carbons (169.30, 155.00, 134.98, 134.15, 127.59, 125.30, 51.75, 29.79). Anal. Calcd for $C_{10}H_8Cl_2N_2O_2$: C, 46.35; H, 3.11; N, 10.81; Cl, 27.36. Found: C, 46.43; H, 2.9; N, 10.73; Cl, 27.33.

Preparation 2

(E)-4-((1-(3,5-dichlorophenyl)-3-methyl-2,5-dioxoimidazolidin-4-ylidene)methyl)benzonitrile

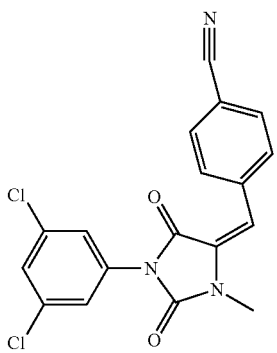

A mixture of 3-(3,5-dichlorophenyl)-1-methylimidazolidine-2,4-dione (1.00 kg, 3.86 mol), 4-cyanobenzaldehyde (0.70 kg, 5.79 mol) and pyrrolidone (0.27 kg, 3.86 mmol) was refluxed in EtOH (13.00 L) for 20-24 hours at a temperature of 78° C. The completeness of the reaction was followed by HPLC. Upon reaction completion, the suspension was cooled to 65° C. and THF (4.33 L) was added in 5-10 minutes. The suspension was cooled to 20-25° C. in 3-4 hours and was then filtered. The filter cake was washed with EtOH (4×2.00 L) and dried at maximum 40° C. to a constant weight. (E)-4-((1-(3,5-dichlorophenyl)-3-methyl-2,5-dioxoimidazolidin-4-ylidene)methyl)benzonitrile (1.24 kg, 86%) was obtained as a fluffy, yellowish crystalline solid. mp=239-241° C. $^1$H NMR (DMSO-$d_6$): 8.07 (2H, d, J=8.3 Hz), 7.86 (2H, d, J=8.4 Hz), 7.72 (1H, m), 7.59 (2H, m), 6.72 (1H, s), 3.35 (3H, s). $^{13}$C NMR (DMSO-$d_6$): 14 Carbons (159.80, 151.48, 137.64, 133.83, 133.70, 131.80, 130.80, 130.68, 127.71, 125.51, 118.83, 114.48, 110.32, 26.72). Anal. Calcd for $C_{18}H_{11}Cl_2N_3O_2$: C, 58.08; H, 2.97; N, 11.29; Cl, 19.05. Found: C, 58.14; H, 2.72; N, 11.14; Cl, 19.15.

Example 1

4-[(5S*,9R*)-3-(3,5-Dichlorophenyl)-1-methyl-2,4-dioxo-1,3,7-triazaspiro[4.4]non-9-yl]-benzonitrile hydrochloride salt

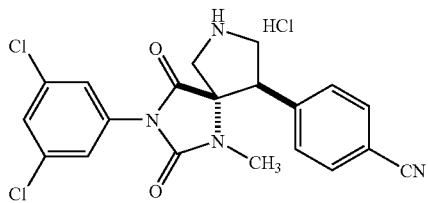

A mixture of (E)-4-((1-(3,5-dichlorophenyl)-3-methyl-2,5-dioxoimidazolidin-4-ylidene)methyl)benzonitrile (1.00 kg, 2.69 mol), glycine (0.50 kg, 6.72 mol) and hexamethylenetetramine (0.28 kg, 2.02 mol) in 1-methyl-2-pyrrolidinone (5.00 L) and toluene (2.50 L) was heated at 140° C. for 7-8 hours. The completeness of the reaction was followed by HPLC. Upon reaction completion, the mixture was cooled to 40-50° C. and filtered. The filtered solid was washed with toluene (0.67 L). To the filtrate was added HCl (1M, 13.33 L, 13.33 mol). The resulting biphasic mixture was heated to 50-60° C. and was stirred for 10-15 minutes. The aqueous phase was separated and the organic phase was washed with HCl (1M, 1.67 L, 1.67 mol) at 60-80° C. The aqueous phases were combined and were stirred at 80° C. for 2 hours. The solution was cooled slowly in 3-4 hours to 20-25° C. with gentle stirring and seeding. Crystallization occurred and the resulting suspension was put aside at 20-25° C. for at least 16 hours with occasional stirring, cooled to 0-5° C. in 2 hours, stirred gently at 0-5° C. for 2 hours and then filtered. The filter cake was washed with ice water (2×2.50 L) and dried at maximum 40° C. to a constant weight. 4-[(5S*,9R*)-3-(3,5-Dichlorophenyl)-1-methyl-2,4-dioxo-1,3,7-triazaspiro[4.4]non-9-yl]-benzonitrile hydrochloride salt (1.09 kg, 90%) was obtained as beige crystalline solid. mp=183-185° C. $^1$H NMR (DMSO-$d_6$): 7.87(2H, d, J=8.1 Hz), 7.61 (1H, m), 7.40 (2H, d, J=8.1 Hz), 6.68 (2H, m), 4.17 (1H, m), 3.85 (2H, m), 3.76 (2H, m), 3.43 (3H, s), 3.24(2H, s). $^{13}$C NMR (DMSO-$d_6$): 14 Carbons (170.84, 152.92, 137.35, 133.94, 132.87, 132.35, 128.01, 124.50, 118.12, 111.30, 71.42, 46.57, 45.11, 25.51). Anal. Calcd for $C_{20}H_{17}Cl_3N_4O_2+1.3$ $H_2O$: C, 50.51; H, 3.91; N, 11.79; Cl, 22.39. Found: C, 50.56; H, 3.86; N, 11.58; Cl, 21.98; KF, 5.12.

Example 2a

4-[(5S,9R)-3-(3,5-Dichlorophenyl)-1-methyl-2,4-dioxo-1,3,7-triazaspiro[4.4]non-9-yl]-benzonitrile semi (+)-DTTA salt

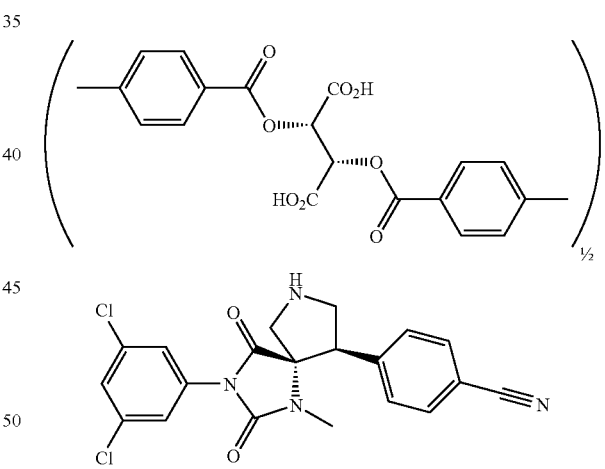

To a suspension of 4-[(5S*,9R*)-3-(3,5-Dichlorophenyl)-1-methyl-2,4-dioxo-1,3,7-triazaspiro[4.4]non-9-yl]-benzonitrile hydrochloric acid salt (1.00 kg, 2.21 mol) in dichloromethane (10.67 L) was added diispopropylethylamine (0.29 kg, 2.21 mol). The mixture was stirred to a clear solution, to which (+)-Di-p-toluoyl-D-tartaric acid (0.21 kg, 0.55 mol) was added. The resulting solution was warmed to 34-36° C. and seeded immediately. It was cooled to 20-25° C. in 1.5-2.0 hours. Crystallization occurred during cooling. TBME (2.75 L) was added in 0.5 hours. The suspension was stirred at 20-25° C. for 16 hours and then filtered. The filter cake was washed with dichloromethane/TBME (2/1, 1.00 L), TBME (1 L) and dried at maximum 35° C. to a constant weight. 4-[(5S,9R)-3-(3,5-Dichlorophenyl)-

1-methyl-2,4-dioxo-1,3,7-triazaspiro[4.4]non-9-yl]-benzonitrile semi (+)-DTTA salt (0.47 kg, 35%) was obtained as a white crystalline solid. mp=175-177° C. $^{1}$H NMR (DMSO-d$_6$): 7.86 (2H, d, J=8.1 Hz), 7.81 (2H, d, J=8.3 Hz), 7.61 (1H, m), 7.28 (2H, d, J=8.1 Hz), 7.22 (2H, 8.5 Hz), 6.68 (2H, m), 5.71 (1H, s), 3.81(1H, m), 3.50 (4H, m), 3.06 (3H, s), 2.34 (3H, s). $^{13}$C NMR (DMSO-d$_6$): 24 Carbons (171.45, 169.40, 165.04, 152.88, 143.61, 138.99, 133.88, 133.08, 132.16, 129.26, 129.20, 128.76, 127.84, 126.99, 124.51, 118.25, 110.78, 72.81, 73.38, 48.15, 47.51, 46.30, 24.90, 21.14). Anal. Calcd for $C_{30}H_{25}Cl_2N_4O_6$+0.5 $H_2O$: C, 58.40; H, 4.17; N, 9.08; Cl, 11.49. Found C, 58.58; H, 4.06; N, 8.94; Cl, 11.38; KF, 1.59.

Example 2b

4-[(5S,9R)-3-(3,5-Dichlorophenyl)-1-methyl-2,4-dioxo-1,3,7-triazaspiro[4.4]non-9-yl]-benzonitrile semi (+)-DTTA salt

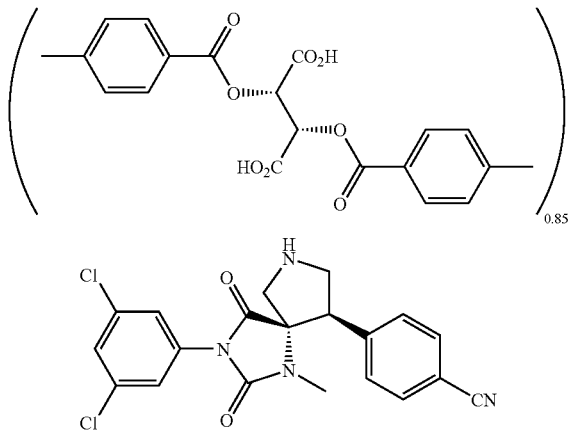

A mixture of (E)-4-((1-(3,5-dichlorophenyl)-3-methyl-2,5-dioxoimidazolidin-4-ylidene)methyl)benzonitrile (10.0 g, 26.9 mmol), glycine (5.06 g, 67.4 mmol), hexamethylenetetramine (2.82 g, 20.1 mmol) in 50 mL N-methylpyrrolidinone and 25 mL of toluene under nitrogen was heated to 138° C. for approximately 12 h. Next, 25 mL toluene and 25 mL H$_2$O were added. The aqueous and nonaqueous layers were split, and the aqueous layer was washed with 25 mL of toluene, and the nonaqueous layers were combined to form a nonaqueous mixture. The nonaqueous mixture was heated to 45-50° C. and ethylene diamine (7.0 mL) was added. The nonaqueous mixture was stirred for 3 hours and then cooled to room temperature. Next, 50 mL H$_2$O was added, followed by the addition of 10 mL brine. The next addition was 25 mL toluene, which was followed by the addition of 125 mL CH$_2$Cl$_2$. The bottom layer of the mixture was removed through a filter. Next, (+)-Di-p-toluoyl-D-tartaric acid (2.59 g, 6.7 mmol) was added and the mixture was stirred for 18 h to form a slurry. Slowly 40 mL of MTBE was added to the slurry. A wash solution containing 7 mL of MTBE and 11 mL of CH$_2$Cl$_2$ was prepared. Filter paper was wetted with 1 mL of the wash solution. The slurry was filtered and then the filtered to form a cake. The filter, the wash reaction flask, and the cake were washed with the remaining 16 mL of the wash solution. Next, the cake was washed with 10 mL MTBE. 4-[(5S, 9R)-3-(3,5-Dichlorophenyl)-1-methyl-2,4-dioxo-1,3,7-triazaspiro[4.4]non-9-yl]-benzonitrile semi (+)-DTTA salt (4.0 g, 20% yield) was obtained as a white solid (98.7% HPLC AP and 98.3% ee).

Example 2c

4-[(5S,9R)-3-3,5-Dichlorophenyl)-1-methyl-2,4-dioxo-1,3,7-triazaspiro[4.4]non-9-yl]-benzonitrile semi (+)-DTTA salt A mixture of (E)-4-((1-(3,5-dichlorophenyl)-3-methyl-2,5-dioxoimidazolidin-4-ylidene)methyl)benzonitrile (40.0 g, 107.5 mmol), glycine (19.76 g, 263.2 mmol), hexamethylenetetramine (9.07 g, 64.7 mmol) in 200 mL N-methyl-2-pyrrolidinone and 100 mL of toluene was heated under nitrogen to 143° C. for approximately 5.5 h. Next, the mixture was cooled to 50° C. and a solution of 25 mL of ethylenediamine in 200 mL of tetrahydrofuran was added. The mixture was maintained at a temperature of 50° C. for 30 minutes and then was cooled to room temperature. Next, 520 mL of 20 wt % NaCl aqueous solution was added. The aqueous and nonaqueous layers were separated. The nonaqueous layer was transferred to a vacuum distillation apparatus and solvent was distilled off until the temperature of the residue in the flask reached 58° C. at a pressure of 60 torr. Next, 360 mL of methylene chloride was added, followed by the additions of 20 mL of methanol and 2 mL of water. The next addition was (+)-Di-p-toluoyl-D-tartaric acid (10.38 g, 26.9 mmol), followed by 120 mL of methylene chloride and 0.200 g of seeds of 4-[(5S,9R)-3-(3,5-Dichlorophenyl)-1-methyl-2,4-dioxo-1,3,7-triazaspiro[4,4] non-9-yl]-benzonitrile semi (+)-DTTA salt. A-slurry was formed and was stirred at room temperature for 24 hours. The slurry was filtered and the cake of crystals was washed with 200 mL of methylene chloride in two portions. The washed cake was then dried at 50° C. under vacuum for 24 hours. A total amount of 20.11 g (yield 31%) of 4-[(5S,9R)-3-(3,5-Dichlorophenyl)-1-methyl-2,4-dioxo-1,3,7-triazaspiro[4,4]non-9-yl]-benzonitrile semi (+)-DTTA salt, which was of greater than 99.5% area percent purity, 98.4% potency and 99.2% ee was obtained after drying.

Example 3

5-[(5S,9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid methyl ester hydrochloride salt

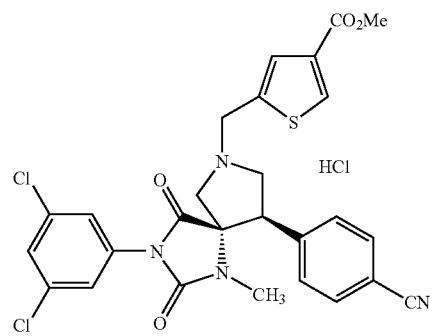

To a suspension of 4-[(5S,9R)-3-(3,5-Dichlorophenyl)-1-methyl-2,4-dioxo-1,3,7-triazaspiro[4.4]non-9-yl]-benzonitrile semi (+)-DTTA salt (7.50 kg, 12.30 mmol) and methyl 5-formylthiophene-3-carboxylate (2.2 kg, 13.10 mol) was added triethylamine (2.08 kg, 20.60 mol) at 20-25° C. The mixture was stirred to a clear solution, to which acetic acid (1.24 kg, 20.60 mol) was added. The resulting mixture was stirred at 20-25° C. for 1 hour and then cooled to 15° C. Solid sodium triacetoxyborohydride (1.31 kg, 6.17 mol) was added and the reaction mixture was stirred for 0.5 hours. The addition of sodium triacetoxyborohydride was repeated three more times. At the end, a total of 5.22 kg (24.7 mol) sodium triacetoxyborohydride was added in 2 hours. The reaction mixture was stirred at 20-25° C. for 16 hours. The completeness of the reaction was followed by HPLC. Upon reaction completion, TBME (48.1 L) was added to the resulting jelly reaction mixture. The mixture was washed with saturated sodium hydrogen carbonate solution (60.0 L×3). The combined aqueous phase was extracted with TBME (48.1 L). All organic layers were combined, washed with brine (48.1 L) and concentrated in vacuum to a volume of 10.6 L. Isopropanol (192.3 L) was added to the residue and the resulting oil precipitates were dissolved upon warming up to 70-75° C. The solvent volume was reduced to 160.0 L by distillation at 70-75° C. Concentrated HCl (1.5 L) was added at 75° C. in 10 minutes followed by the addition of seed crystals. Crystallization occurred upon cooling to 20-25° C. in 16 hours. The mixture was filtered. The cake was washed with isopropanol (9.6 L×2) and dried at maximum 40° C. to a constant weight. 5-[(5S,9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid methyl ester hydrochloride salt (6.57 kg, 88.0%) was obtained as white crystalline solid. mp=204-207° C. $^1$H NMR (CDCl$_3$): 14.22 (1H, b), 8.18 (1H, d, J=0.9 Hz), 7.86 (1H, m), 7.67 (2H, d, J=8.1 Hz), 7.24 (1H, m), 7.23 (2H, d, J=8.1 Hz), 6.67 (2H, m), 4.76 (2H, m), 4.46 (1H, m), 4.16 (1H, m), 4.02 (2H, m), 3.86 (3H, s), 3.75 (1H, m), 3.38 (3H, s). $^{13}$C NMR (CDCl$_3$): 18 Carbons (171.24, 162.32, 152.98, 136.05, 135.27, 134.03, 132.83, 131.94, 130.46, 128.85, 128.56, 123.92, 117.52, 113.43, 71.13, 52.43, 52.22, 46.73). Anal. Calcd for C$_{27}$H$_{23}$Cl$_3$N$_4$O$_4$S: C, 53.52; H, 3.83; N, 9.25; S, 5.29; Cl, 17.55. Found: C, 53.07; H, 3.69; N, 9.08; S, 5.23; Cl, 17.20.

Example 4

5-[(5S,9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid

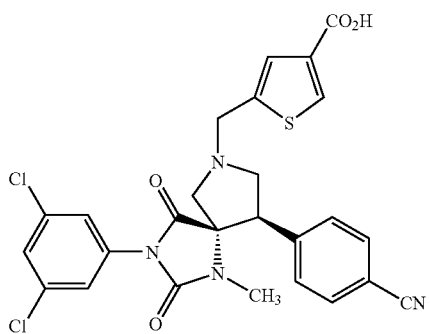

To a solution of 5-[(5S,9R)-9-(4-Cyanophenyl)-3-(3,5-dichlorophenyl)-1-methyl-2,4-dioxo-1,3,7-triazaspiro[4.4] non-7-ylmethyl]-thiophene-3-carboxylic acid methyl ester hydrochloride salt (20.00 g, 33.00 mmol) and 1,2-propanediol (5.0 g) in tetrahydrofuran (200 mL) and water (100 mL) was added slowly potassium hydroxide solution (0.85M, 116 mL) at 8-12° C. in 0.5 hours. The resulting biphasic mixture was stirred at 8-12° C. for 20-27 hours until the reaction was complete. The reaction mixture was washed with n-heptane (200 mL). The pH was adjusted to 6.5 with addition of water (100 mL) and acetic acid (2.5 mL). Tetrahydrofuran was removed under reduced pressure at internal temperature <40° C. The pH was adjusted to 4.5 with addition of isopropyl acetate (400 mL) and acetic acid (11 mL). After 10 minutes of stirring, the aqueous layer was separated and was extracted with isopropylacetate (200 mL). The organic layers were combined, washed with water (100 mL) and concentrated under reduced pressure to a volume of 190 mL at bath temperature <40° C. Crystallization occurred during concentration. The crystal slurry was stirred at 20-25° C. for 16 hours and was then filtered. The cake was washed with cold isopropylacetate (15 mL×3) and dried in vacuum at 35-40° C. to a constant weight. 5-[(5S,9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid (14.35 g, 78.3%) was obtained as white and sandy crystalline solid. mp=209-230° C. $^1$H NMR (Acetone-d$_6$): 8.19 (1H, d, J=1.3 Hz), 7.76 (2H, d, J=8.4 Hz), 7.49 (2H, d, J=8.2 Hz), 7.43 (1H, d, J=1.0 Hz), 7.41 (1H, t, J=1.9 Hz), 6.87 (2H, d, J=1.9 Hz), 4.16 (1H, dd, J1=13.9 Hz J2=0.8 Hz), 4.10 (1H, dd, J1=11.7 Hz, J2=6.2 Hz), 3.99 (1H, d, J=14.0 Hz), 3.48 (1H, d, J=10.6 Hz), 3.47 (1H, dd, J1=9.6 Hz, J2=6.2 Hz), 3.25 (3H, s), 3.24 (1H, dd, J1=9.6 Hz, J2=11.7 Hz), 3.01 (1H, d, J=11.3 Hz). $^{13}$C NMR (Acetone-d$_6$): 22 Carbons (172.69, 163.7, 153.98, 144.55, 142.23, 135.26, 135.09, 134.41, 133.89, 132.96, 130.33, 128.27, 126.98, 125.18, 119.07, 112.44, 74.28, 59.09, 56.45, 54.33, 50.73, 25.75). Anal. Calcd for C$_{26}$H$_{20}$Cl$_2$N$_4$O$_4$S: C, 56.22; H, 3.62; N, 10.08; S, 5.77; Cl, 12.76. Found: C, 56.27; H, 3.20; N, 9.97; S, 5.65; Cl, 12.68.

Crystalline Forms of 5-[(5S,9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid, and Solvates and Salts Various crystalline forms of the substituted spiro-hydantoin compound (IIIn), its solvates and salts were prepared and are tabulated in Table 1. The unit cell data and other properties for these examples are tabulated in Tables 2a and 2b. The unit cell parameters were obtained from single crystal X-ray crystallographic analysis. A detailed account of unit cells can be found in Chapter 3 of Stout & Jensen, "*X-Ray Structure Determination: A Practical Guide*", (MacMillian, 1968). The fractional atomic coordinates for the various crystalline forms are tabulated in Tables 3 to 16.

X-ray powder diffraction (PXRD) data were obtained using a Bruker GADDS (General Area Detector Diffraction System) manual chi platform goniometer. Powder samples were placed in thin walled glass capillaries of 1 mm or less in diameter; the capillary was rotated during data collection. The sample-detector distance was 17 cm. The radiation was Cu Kα (λ=1.5418 Å). Data were collected for 3<2θ<35° with a sample exposure time of at least 300 seconds.

Single crystal X-ray data were collected on a Bruker-Nonius CAD4 serial diffractometer (Bruker Axs, Inc., Madison Wis.). Unit cell parameters were obtained through least-squares analysis of the experimental diffractometer settings of 25 high-angle reflections. Intensities were measured using Cu Kα radiation (λ=1.5418 Å) at a constant temperature with the θ-2θ variable scan technique and were corrected only for Lorentz-polarization factors. Background counts were collected at the extremes of the scan for half of the time of the scan. Alternately, single crystal data were collected on a Bruker-Nonius Kappa CCD 2000 system using Cu Kα radiation (λ=1.5418 Å). Indexing and processing of the measured intensity data were carried out with the HKL2000 software package in the Collect program suite R. Hooft, Nonius B. V. (1998). When indicated, crystals were cooled in the cold stream of an Oxford cryogenic system during data collection.

The structures were solved by direct methods and refined on the basis of observed reflections using either the SDP software package SDP, Structure Determination Package, Enraf-Nonius, Bohemia, N.Y.) with minor local modifications or the crystallographic package, MAXUS (maXus solution and refinement software suit: S. Mackay, C. J. Gilmore, C. Edwards, M. Tremayne, N. Stewart, and K. Shankland. maXus is a computer program for the solution and refinement of crystal structures from diffraction data.

The derived atomic parameters (coordinates and temperature factors) were refined through full matrix least-squares. The function minimized in the refinements was $\Sigma_w(|F_o|-|F_c|)^2$. R is defined as $\Sigma||F|-|F||/\Sigma|F_o|$ while $R^w=[\Sigma_w(|F_o|-|F_c|)^2/\Sigma_w|F_o|^2]^{1/2}$ where w is an appropriate weighting function based on errors in the observed intensities. Difference maps were examined at all stages of refinement. Hydrogen atoms were introduced in idealized positions with isotropic temperature factors, but no hydrogen parameters were varied.

Melting points for the crystals were determined by hot stage microscopy. Crystals were placed on a glass slide, covered with a cover slip, and heated on a Linkam LTS350 hot stage mounted on a microscope (Linkham Scientific Instruments Ltd, Tadworth, U.K.). The heating rate was controlled at 10° C./min for the temperature range, ambient to 300° C. The crystals were observed visually for evidence of phase transformation, changes in birefringence, opacity, melting, and/or decomposition.

The differential scanning calorimetry was used to test the crystalline forms was a TA Instruments™ model Q1000. The DSC cell/sample chamber was purged with 100 ml/min of ultra-high purity nitrogen gas. The instrument was calibrated with high purity indium. The heating rate was 10° C. per minute in the temperature range between 25 and 300° C. The heat flow, which was normalized by sample weight, was plotted versus the measured sample temperature. the data were reported in units of watts/gram ("W/g"). The plot was made with the endothermic peaks pointing down. The endothermic melt peak (melting point) was evaluated for extrapolated onset temperature.

Crystals of form N-1 were grown from ethylene glycol mixture with ethyl acetate as an counter-solvent (determination at −50° C.), or by slow evaporation of a solution of (S)-2methyl-1-butanol (determination at 22° C.).

Crystals of the methanesulfonic acid salt form were prepared by dissolving the methanesulfonic acid salt of substituted spiro-hydantoin compound (IIIn) in a minimum volume of warm (~50° C.) acetonitrile and allowing the mixture to cool slowly to ambient temperature. The crystals appeared as the solution evaporated.

Crystals of the hydrochloric acid salt form were prepared by dissolving the hydrochloric acid salt of substituted spiro-hydantoin compound (IIIn) in a minimum volume of a warm (~50° C.) mixture of ethanol/acetonitrile and allowing the resulting mixture to cool slowly to ambient temperature. The crystals appeared as the solution evaporated.

Crystals of the solvated forms were prepared by heating a concentrated solution of Example 4 in the desired solvent followed by cooling to ambient temperature and slow evaporation. In the case of the acetonitrile and n-methylpyrrolidone forms, water was added to the warm solution as a counter-solvent.

Crystals of the desolvated form were prepared by heating crystals of the ethanol containing solvate form (E.5-2) under vacuum (~30 mm) at 90° C. for 90 minutes, to yield single crystals of the desolvated form, TIE.5-2.

TABLE 1

| Form | |
|---|---|
| N-1 | Neat crystal |
| MSA | Methanesulfonic acid salt |
| HCl | Hydrochloric acid salt |
| M.5-2 | Methanol solvate crystal |
| E.5-2 | Ethanol solvate crystal |
| IPA.5-2 | Isopropanol solvate crystal |
| PR.5-2 | n-propanol solvate crystal |
| AN.5-2 | Acrylonitrile solvate crystal |
| NMP.5-2 | n-methylpyrrolidone solvate crystal |
| THF.5-2 | Tetrahydrofuran solvate crystal |
| S2BU.5-2 | S-(+)-2-butanol solvate crystal |
| R2BU.5-2 | R-(−)-2-butanol solvate crystal |
| SA-2 | S-2-methyl-1-butanol/H$_2$O solvate crystal |
| T1E.5-2 | Neat crystal obtained by desolvating ethanol solvate crystal |

Notes for Table 1:
T is the temperature of the crystal.
Z is the number of molecules of the substituted spiro-hydantoin compound (IIIq) in each unit cell.

TABLE 2a

| | Unit Cell Parameters | | | | | | | |
|---|---|---|---|---|---|---|---|---|
| Form | a(Å) | b(Å) | c(Å) | α | β | γ | V(Å$^3$) | T(° C.) |
| N-1 | 12.05 | 17.72 | 13.07 | 90.0 | 112.0 | 90.0 | 2588.3 | −50 |
| N-1 | 12.07 | 17076 | 13.12 | 90.0 | 111.9 | 90.0 | 2608 | +22 |
| MSA | 8.44 | 14.67 | 25.01 | 90.0 | 97.1 | 90.0 | 3075.4 | +22 |
| HCl | 8.26 | 12.56 | 13.22 | 90.0 | 90.2 | 90.0 | 1372.17 | +22 |
| M.5-2 | 11.34 | 14.95 | 31.67 | 90.0 | 90.0 | 90.0 | 5369.6 | −50 |
| E.5-2 | 11.32 | 15.22 | 31.88 | 90.0 | 90.0 | 90.0 | 5493.2 | −50 |
| IPA.5-2 | 11.27 | 15.54 | 31.72 | 90.0 | 90.0 | 90.0 | 5554.1 | −50 |
| PR.5-2 | 11.28 | 15.38 | 31.96 | 90.0 | 90.0 | 90.0 | 5544 | −50 |
| AN.5-2 | 11.26 | 15.18 | 31.45 | 90.0 | 90.0 | 90.0 | 5409.0 | −50 |
| NMP.5-2 | 11.23 | 15.81 | 31.98 | 90.0 | 90.0 | 90.0 | 5679.8 | −50 |
| THF.5-2 | 11.35 | 15.47 | 31.94 | 90.0 | 90.0 | 90.0 | 5607.8 | −50 |
| S2BU.5-2 | 11.25 | 15.68 | 32.10 | 90.0 | 90.0 | 90.0 | 5662.3 | −50 |

TABLE 2a-continued

Unit Cell Parameters

| Form | a(Å) | b(Å) | c(Å) | α | β | γ | V(Å$^3$) | T(° C.) |
|---|---|---|---|---|---|---|---|---|
| R2BU.5-2 | 11.22 | 15.42 | 32.75 | 90.0 | 90.0 | 90.0 | 5666.4 | −50 |
| SA-2 | 11.18 | 15.94 | 32.14 | 90.0 | 90.0 | 90.0 | 5421.6 | −50 |
| T1E.5-2 | 11.38 | 15.22 | 31.29 | 90.0 | 90.0 | 90.0 | 5421.6 | +90 |

TABLE 2b

Unit Cell Parameters (continued)

| Form | Z | V$_m$ | SG | D$_{calc}$ (g/cm$^3$) | MP (° C.) |
|---|---|---|---|---|---|
| N-1 | 2 | 647 | P2$_1$ | 1.425 | 233-236 |
| N-1 | 2 | 652 | P2$_1$ | 1.425 | — |
| MSA | 2 | 769 | P2$_1$ | 1.405 | 228-288 (d) |
| HCl | 2 | 686 | P2$_1$ | 1.433 | 183-250 (d) |
| M.5-2 | 2 | 671 | P2$_1$2$_1$2$_1$ | 1.414 | 193-196 |
| E.5-2 | 2 | 687 | P2$_1$2$_1$2$_1$ | 1.399 | 234-237 |
| IPA.5-2 | 2 | 694 | P2$_1$2$_1$2$_1$ | 1.400 | 233-238 |
| PR.5-2 | 2 | 693 | P2$_1$2$_1$2$_1$ | 1.403 | 232-236 |
| AN.5-2 | 2 | 676 | P2$_1$2$_1$2$_1$ | 1.414 | 234-237 |
| NMP.5-2 | 2 | 710 | P2$_1$2$_1$2$_1$ | 1.415 | 240-243 |
| THF.5-2 | 2 | 701 | P2$_1$2$_1$2$_1$ | 1.401 | 232-237 |
| S2BU.5-2 | 2 | 708 | P2$_1$2$_1$2$_1$ | 1.390 | 236-240 |
| R2BU.5-2 | 2 | 708 | P2$_1$2$_1$2$_1$ | 1.390 | 238-241 |
| SA-2 | 2 | 716 | P2$_1$2$_1$2$_1$ | 1.412 | 234-240 |
| T1E.5-2 | 2 | 678 | P2$_1$2$_1$2$_1$ | 1.361 | — |

V$_m$ is the molar volume.
SG is the crystallographic space group.
D$_{calc}$ is the calculated density.
MP is the melting point or temperature of decomposition (d).

TABLE 3

Positional Parameters for 5-[(5S, 9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid form N-1 at +22° C.

| Atom | X | Y | Z | Atom | X | Y | Z |
|---|---|---|---|---|---|---|---|
| CL12 | 0.8320 | 0.5937 | 0.7092 | CL52 | −0.0041 | 1.0060 | −0.0061 |
| CL14 | 0.4726 | 0.3962 | 0.5697 | CL54 | 0.4364 | 0.9044 | 0.0567 |
| S25 | −0.0350 | 0.7224 | 0.9936 | S65 | −0.0641 | 0.5380 | 0.4600 |
| O2 | 0.6393 | 0.5998 | 1.0048 | O42 | 0.1333 | 0.8758 | 0.3723 |
| O4 | 0.2963 | 0.6345 | 0.7037 | O44 | 0.2477 | 0.6839 | 0.1995 |
| O29 | −0.3565 | 0.8834 | 0.7640 | O69 | −0.3766 | 0.3748 | 0.2225 |
| O30 | −0.4184 | 0.8043 | 0.8654 | O70 | −0.4379 | 0.4507 | 0.3246 |
| N1 | 0.4483 | 0.6355 | 0.9879 | N41 | 0.1558 | 0.7483 | 0.4060 |
| N3 | 0.4802 | 0.6064 | 0.8367 | N43 | 0.1923 | 0.7933 | 0.2639 |
| N7 | 0.1664 | 0.7169 | 0.9055 | N47 | 0.1365 | 0.5570 | 0.3856 |
| N22 | 0.1992 | 0.2288 | 0.7263 | N62 | 0.8565 | 0.7833 | 0.5488 |
| C2 | 0.5324 | 0.6124 | 0.9494 | C42 | 0.1564 | 0.8119 | 0.3535 |
| C4 | 0.3615 | 0.6301 | 0.7983 | C45 | 0.1882 | 0.6825 | 0.3581 |
| C5 | 0.3336 | 0.6471 | 0.8975 | C46 | 0.0897 | 0.6210 | 0.3134 |
| C6 | 0.2801 | 0.7290 | 0.8917 | C48 | 0.2632 | 0.5565 | 0.4051 |
| C8 | 0.1208 | 0.6450 | 0.8504 | C49 | 0.2949 | 0.6373 | 0.4413 |
| C9 | 0.2315 | 0.5956 | 0.9044 | C50 | 0.2001 | 0.8463 | 0.1863 |
| C10 | 0.5347 | 0.5718 | 0.7691 | C51 | 0.1045 | 0.8954 | 0.1355 |
| C11 | 0.6434 | 0.5990 | 0.7712 | C52 | 0.1163 | 0.9457 | 0.0606 |
| C12 | 0.6956 | 0.5614 | 0.7080 | C53 | 0.2177 | 0.9503 | 0.0357 |
| C13 | 0.6465 | 0.5000 | 0.6448 | C54 | 0.3067 | 0.9015 | 0.0866 |
| C14 | 0.5353 | 0.4756 | 0.6446 | C55 | 0.3024 | 0.8489 | 0.1622 |
| C15 | 0.4798 | 0.5110 | 0.7037 | C56 | 0.4201 | 0.6664 | 0.4596 |
| C16 | 0.2237 | 0.5163 | 0.8573 | C57 | 0.4836 | 0.6449 | 0.3957 |
| C17 | 0.1577 | 0.4986 | 0.7504 | C58 | 0.5980 | 0.6739 | 0.4164 |
| C18 | 0.1500 | 0.4248 | 0.7126 | C59 | 0.6479 | 0.7218 | 0.5014 |
| C19 | 0.2117 | 0.3688 | 0.7843 | C60 | 0.5864 | 0.7437 | 0.5657 |

TABLE 3-continued

Positional Parameters for 5-[(5S, 9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid form N-1 at +22° C.

| Atom | X | Y | Z | Atom | X | Y | Z |
|---|---|---|---|---|---|---|---|
| C20 | 0.2786 | 0.3848 | 0.8898 | C61 | 0.4729 | 0.7150 | 0.5462 |
| C21 | 0.2866 | 0.4603 | 0.9281 | C62 | 0.7675 | 0.7544 | 0.5273 |
| C22 | 0.2024 | 0.2911 | 0.7480 | C63 | 0.0729 | 0.4860 | 0.3444 |
| C23 | 0.0859 | 0.7806 | 0.8629 | C64 | −0.0463 | 0.4870 | 0.3561 |
| C24 | −0.0266 | 0.7747 | 0.8868 | C66 | −0.2089 | 0.5082 | 0.4223 |
| C26 | −0.1804 | 0.7485 | 0.9645 | C67 | −0.2409 | 0.4630 | 0.3359 |
| C27 | −0.2178 | 0.7955 | 0.8775 | C68 | −0.1471 | 0.4499 | 0.2980 |
| C28 | −0.1303 | 0.8120 | 0.8336 | C69 | −0.3578 | 0.4270 | 0.2916 |
| C29 | −0.3367 | 0.8321 | 0.8336 | C71 | 0.1137 | 0.7460 | 0.4980 |
| C31 | 0.4740 | 0.6495 | 1.1008 | H70 | −0.518 | 0.428 | 0.283 |
| H71 | −0.496 | 0.831 | 0.828 | — | — | — | — |

TABLE 4

Positional Parameters for 5-[(5S, 9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid form N-1 at −50° C.

| Atom | X | Y | Z | Atom | X | Y | Z |
|---|---|---|---|---|---|---|---|
| CL12 | 0.8357 | 0.5938 | 0.7095 | CL52 | −0.0091 | 1.0057 | −0.0086 |
| CL14 | 0.4755 | 0.3943 | 0.5696 | CL54 | 0.4335 | 0.9070 | 0.0533 |
| S25 | −0.0333 | 0.7208 | 0.9965 | S65 | −0.0633 | 0.5386 | 0.4605 |
| O2 | 0.6426 | 0.6011 | 1.0065 | O42 | 0.1318 | 0.8757 | 0.3719 |
| O4 | 0.2970 | 0.6342 | 0.7036 | O44 | 0.2506 | 0.6839 | 0.1999 |
| O29 | −0.3553 | 0.8836 | 0.7676 | O69 | −0.3762 | 0.3730 | 0.2240 |
| O30 | −0.4177 | 0.8027 | 0.8665 | O70 | −0.4382 | 0.4518 | 0.3241 |
| N1 | 0.4501 | 0.6354 | 0.9891 | N41 | 0.1559 | 0.7476 | 0.4072 |
| N3 | 0.4825 | 0.6058 | 0.8368 | N43 | 0.1928 | 0.7931 | 0.2642 |
| N7 | 0.1681 | 0.7165 | 0.9072 | N47 | 0.1376 | 0.5555 | 0.3863 |
| N22 | 0.1973 | 0.2258 | 0.7214 | N62 | 0.8598 | 0.7840 | 0.5508 |
| C2 | 0.5368 | 0.6129 | 0.9539 | C42 | 0.1547 | 0.8120 | 0.3526 |
| C4 | 0.3656 | 0.6299 | 0.7991 | C44 | 0.2169 | 0.7176 | 0.2642 |
| C5 | 0.3358 | 0.6473 | 0.9004 | C45 | 0.1893 | 0.6815 | 0.3593 |
| C6 | 0.2831 | 0.7280 | 0.8946 | C46 | 0.0911 | 0.6203 | 0.3131 |
| C8 | 0.1231 | 0.6437 | 0.8530 | C48 | 0.2661 | 0.5553 | 0.4075 |
| C9 | 0.2335 | 0.5945 | 0.9056 | C49 | 0.2981 | 0.6369 | 0.4429 |
| C10 | 0.5386 | 0.5715 | 0.7689 | C50 | 0.1988 | 0.8467 | 0.1846 |
| C11 | 0.6470 | 0.5988 | 0.7721 | C51 | 0.1020 | 0.8949 | 0.1343 |
| C12 | 0.6994 | 0.5613 | 0.7079 | C52 | 0.1130 | 0.9463 | 0.0591 |
| C13 | 0.6482 | 0.4988 | 0.6448 | C53 | 0.2141 | 0.9523 | 0.0322 |
| C14 | 0.5385 | 0.4740 | 0.6444 | C54 | 0.3049 | 0.9021 | 0.0836 |
| C15 | 0.4814 | 0.5099 | 0.7053 | C55 | 0.3012 | 0.8493 | 0.1598 |
| C16 | 0.2281 | 0.5148 | 0.8592 | C56 | 0.4207 | 0.6657 | 0.4602 |
| C17 | 0.1572 | 0.4976 | 0.7494 | C57 | 0.4865 | 0.6439 | 0.3961 |
| C18 | 0.1490 | 0.4239 | 0.7109 | C58 | 0.6012 | 0.6735 | 0.4170 |
| C19 | 0.2125 | 0.3674 | 0.7818 | C59 | 0.6506 | 0.7224 | 0.5038 |
| C20 | 0.2828 | 0.3832 | 0.8907 | C60 | 0.5879 | 0.7438 | 0.5686 |
| C21 | 0.2897 | 0.4576 | 0.9292 | C61 | 0.4745 | 0.7156 | 0.5479 |
| C22 | 0.2018 | 0.2887 | 0.7449 | C62 | 0.7691 | 0.7552 | 0.5285 |
| C23 | 0.0873 | 0.7798 | 0.8643 | C63 | 0.0748 | 0.4849 | 0.3462 |
| C24 | −0.0251 | 0.7745 | 0.8899 | C64 | −0.0458 | 0.4859 | 0.3571 |
| C26 | −0.1781 | 0.7461 | 0.9673 | C66 | −0.2077 | 0.5093 | 0.4239 |
| C27 | −0.2180 | 0.7952 | 0.8802 | C67 | −0.2403 | 0.4623 | 0.3370 |
| C28 | −0.1292 | 0.8122 | 0.8356 | C68 | −0.1458 | 0.4479 | 0.2986 |

TABLE 4-continued

Positional Parameters for 5-[(5S, 9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid form N-1 at −50° C.

| Atom | X | Y | Z | Atom | X | Y | Z |
|---|---|---|---|---|---|---|---|
| C29 | −0.3363 | 0.8304 | 0.8342 | C69 | −0.3575 | 0.4257 | 0.2904 |
| C31 | 0.4777 | 0.6506 | 1.1064 | C71 | 0.1120 | 0.7447 | 0.4982 |
| H71 | −0.4958 | 0.8314 | 0.8282 | H70 | −0.5181 | 0.4278 | 0.2831 |

TABLE 5

Positional Parameters for 5-[(5S, 9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid hydrochloric acid salt form N-1 at +22° C.

| Atom | X | Y | Z | Atom | X | Y | Z |
|---|---|---|---|---|---|---|---|
| CL | 0.1121 | 0.3033 | 0.0351 | C11 | −0.2752 | 0.6987 | 0.4733 |
| CL12- | 0.3080 | 0.7480 | 0.6709 | C12 | −0.3418 | 0.7682 | 0.5435 |
| CL14- | 0.5749 | 0.9780 | 0.3722 | C13 | −0.4385 | 0.8540 | 0.5136 |
| S25 | 0.5294 | 0.6673 | −0.0499 | C14 | −0.4614 | 0.8694 | 0.4111 |
| O2 | −0.4392 | 0.5139 | 0.3138 | C15 | −0.3986 | 0.8023 | 0.3395 |
| O4 | −0.0187 | 0.7353 | 0.2445 | C16 | 0.1149 | 0.5204 | 0.3537 |
| O30 | 0.6522 | 0.2985 | −0.1412 | C17 | 0.0355 | 0.4535 | 0.4201 |
| O31 | 0.8587 | 0.4144 | −0.1563 | C18 | 0.0418 | 0.4737 | 0.5245 |
| N1 | −0.2085 | 0.4890 | 0.2212 | C19 | 0.1292 | 0.5582 | 0.5610 |
| N3 | −0.2408 | 0.6431 | 0.3009 | C20 | 0.2148 | 0.6230 | 0.4952 |
| N7 | 0.1463 | 0.5347 | 0.0708 | C21 | 0.2062 | 0.6033 | 0.3924 |
| N38 | 0.1366 | 0.6019 | 0.7499 | C23 | 0.2167 | 0.5990 | −0.0131 |
| C2 | −0.3107 | 0.5422 | 0.2813 | C24 | 0.3854 | 0.5692 | −0.0391 |
| C4 | −0.1017 | 0.6558 | 0.2482 | C26 | 0.6707 | 0.5812 | −0.0942 |
| C5 | −0.0641 | 0.5498 | 0.1979 | C27 | 0.6109 | 0.4804 | −0.1000 |
| C6 | −0.0302 | 0.5619 | 0.0846 | C28 | 0.4483 | 0.4728 | −0.0680 |
| C8 | 0.2251 | 0.5448 | 0.1709 | C29 | 0.7088 | 0.3885 | −0.1347 |
| C9 | 0.0955 | 0.5008 | 0.2414 | C32 | −0.2491 | 0.3829 | 0.1834 |
| C10 | −0.3047 | 0.7164 | 0.3723 | C37 | 0.1375 | 0.5826 | 0.6677 |

TABLE 6

Positional Parameters for 5-[(5S, 9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid methanesulfonic acid salt form N-1 at +22°

| Atom | X | Y | Z | Atom | X | Y | Z |
|---|---|---|---|---|---|---|---|
| CL12 | 0.9261 | 0.1154 | 0.1538 | C17 | 0.6361 | 0.5517 | 0.3910 |
| CL14 | 0.4307 | 0.1900 | 0.0063 | C19 | 0.7794 | 0.4800 | 0.4692 |
| CL52 | −0.2242 | 0.5704 | 0.1814 | C20 | 0.6522 | 0.5279 | 0.4828 |
| CL54 | 0.0628 | 0.6946 | 0.0161 | C21 | 0.5696 | 0.5700 | 0.4365 |
| S1 | 0.2956 | 0.6806 | 0.6536 | C22 | 0.6088 | 0.5350 | 0.5371 |
| S2 | 0.8484 | 1.2036 | 0.6446 | C25 | 0.2242 | 0.4769 | 0.1741 |
| S18 | 0.8009 | 0.4823 | 0.4036 | C26 | 0.3196 | 0.5174 | 0.1378 |
| S58 | 0.7139 | 0.7779 | 0.4150 | C27 | 0.2860 | 0.5033 | 0.0831 |
| O1 | 0.6042 | 0.4185 | 0.2207 | C28 | 0.1568 | 0.4495 | 0.0635 |
| O3 | 0.2595 | 0.1812 | 0.2152 | C29 | 0.0611 | 0.4106 | 0.0978 |
| O23 | 0.6598 | 0.4837 | 0.5738 | C30 | 0.0947 | 0.4246 | 0.1527 |
| O24 | 0.5175 | 0.6029 | 0.5446 | C31 | 0.1220 | 0.4379 | 0.0056 |
| O41 | 0.4508 | 0.7693 | 0.2123 | C33 | 0.1317 | 0.3021 | 0.2896 |
| O43 | −0.0252 | 0.9049 | 0.2297 | C41 | 0.3538 | 0.8255 | 0.2224 |
| O63 | 0.7690 | 0.9012 | 0.5832 | C43 | 0.1152 | 0.8946 | 0.2334 |
| O64 | 0.8275 | 1.0297 | 0.5401 | C45 | 0.3874 | 0.9136 | 0.2559 |
| O81 | 0.3670 | 0.7576 | 0.6820 | C46 | 0.4948 | 0.8915 | 0.3099 |
| O82 | 0.4073 | 0.6118 | 0.6395 | C48 | 0.6600 | 0.9642 | 0.2502 |
| O83 | 0.1765 | 0.6387 | 0.6821 | C49 | 0.4913 | 0.9813 | 0.2256 |
| O85 | 0.7335 | 1.2429 | 0.6758 | C50 | 0.1068 | 0.7628 | 0.1712 |
| O86 | 0.8125 | 1.1097 | 0.6334 | C51 | −0.0028 | 0.7060 | 0.1917 |
| O87 | 1.0113 | 1.2155 | 0.6676 | C52 | −0.0910 | 0.6478 | 0.1562 |
| N2 | 0.4422 | 0.2927 | 0.2028 | C53 | −0.0740 | 0.6438 | 0.1017 |
| N4 | 0.2636 | 0.3183 | 0.2589 | C54 | 0.0358 | 0.6999 | 0.0840 |
| N7 | 0.4240 | 0.5370 | 0.3128 | C55 | 0.1308 | 0.7603 | 0.1177 |

TABLE 6-continued

Positional Parameters for 5-[(5S, 9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid methanesulfonic acid salt form N-1 at +22°

| Atom | X | Y | Z | Atom | X | Y | Z |
|---|---|---|---|---|---|---|---|
| N32 | 0.0939 | 0.4281 | −0.0395 | C56 | 0.7898 | 0.9057 | 0.3386 |
| N42 | 0.1940 | 0.8265 | 0.2060 | C57 | 0.7716 | 0.8858 | 0.3964 |
| N44 | 0.2299 | 0.9449 | 0.2615 | C59 | 0.7212 | 0.8100 | 0.4801 |
| N47 | 0.6416 | 0.9485 | 0.3091 | C60 | 0.7672 | 0.8991 | 0.4881 |
| N72 | 0.3239 | 0.9315 | −0.0495 | C61 | 0.7988 | 0.9421 | 0.4391 |
| C1 | 0.4878 | 0.3743 | 0.2263 | C62 | 0.7877 | 0.9426 | 0.5417 |
| C3 | 0.3146 | 0.2551 | 0.2252 | C65 | 0.4629 | 0.9729 | 0.1645 |
| C5 | 0.3564 | 0.3993 | 0.2602 | C66 | 0.3222 | 1.0102 | 0.1375 |
| C6 | 0.4319 | 0.4338 | 0.3162 | C67 | 0.2864 | 1.0008 | 0.0822 |
| C8 | 0.3704 | 0.5639 | 0.2551 | C68 | 0.3895 | 0.9509 | 0.0545 |
| C9 | 0.2633 | 0.4858 | 0.2346 | C69 | 0.5274 | 0.9154 | 0.0793 |
| C10 | 0.5218 | 0.2477 | 0.1623 | C70 | 0.5656 | 0.9256 | 0.1351 |
| C11 | 0.6706 | 0.2098 | 0.1768 | C71 | 0.3545 | 0.9399 | −0.0042 |
| C12 | 0.7413 | 0.1667 | 0.1374 | C73 | 0.1936 | 1.0198 | 0.2961 |
| C13 | 0.6712 | 0.1592 | 0.0858 | C84 | 0.1971 | 0.7235 | 0.5931 |
| C14 | 0.5247 | 0.1990 | 0.0725 | C88 | 0.8291 | 1.2606 | 0.5819 |
| C15 | 0.4464 | 0.2425 | 0.1102 | H641 | 0.8200 | 1.0618 | 0.5791 |
| C16 | 0.5780 | 0.5803 | 0.3335 | H241 | 0.4804 | 0.5991 | 0.5847 |

TABLE 7

Positional Parameters for 5-[(5S, 9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid form AN.5-2 at −50° C.

| Atom | X | Y | Z | Atom | X | Y | Z |
|---|---|---|---|---|---|---|---|
| CL1 | 0.4762 | 0.8582 | 0.2241 | C38 | 0.7741 | 0.7541 | 0.3671 |
| CL2 | 0.1783 | 1.0036 | 0.1116 | C39 | 0.8648 | 0.7844 | 0.3399 |
| CL3 | 0.5656 | 0.6748 | 0.3782 | C40 | 0.8598 | 0.7784 | 0.2979 |
| CL4 | 0.9866 | 0.8327 | 0.3645 | C41 | 1.0153 | 0.8147 | 0.1862 |
| S1 | 0.8472 | 0.4402 | 0.0504 | C42 | 1.0276 | 0.9059 | 0.2052 |
| S2 | 0.5018 | 0.9512 | 0.0562 | C43 | 1.1014 | 0.9120 | 0.2404 |
| O1 | 0.1093 | 0.6619 | 0.0999 | C44 | 1.1579 | 0.8343 | 0.2562 |
| O2 | 0.5123 | 0.6594 | 0.0895 | C45 | 1.1450 | 0.7523 | 0.2388 |
| O3 | 0.8015 | 0.1829 | −0.0391 | C46 | 1.0768 | 0.7450 | 0.2027 |
| O4 | 0.9853 | 0.2002 | −0.0151 | C47 | 1.2338 | 0.8515 | 0.2960 |
| O5 | 0.7639 | 0.5814 | 0.2270 | C48 | 0.6338 | 0.8934 | 0.0494 |
| O6 | 0.7653 | 0.8841 | 0.2176 | C49 | 0.4333 | 0.8810 | 0.0213 |
| O7 | 0.3670 | 0.7678 | −0.0448 | C50 | 0.5062 | 0.8230 | 0.0050 |
| O8 | 0.5321 | 0.6872 | −0.0327 | C51 | 0.6215 | 0.8288 | 0.0216 |
| N1 | 0.2395 | 0.5582 | 0.0720 | C52 | 0.4687 | 0.7490 | −0.0252 |
| N2 | 0.3145 | 0.6834 | 0.0991 | C98 | 0.2593 | 0.6946 | 0.4089 |
| N3 | 0.5239 | 0.4627 | 0.0386 | C99 | 0.1563 | 0.6482 | 0.4167 |
| N4 | 0.3323 | 0.5860 | 0.3112 | H | 0.5474 | 0.5694 | 0.2364 |
| N5 | 0.7949 | 0.6776 | 0.1702 | H11 | 0.1985 | 0.4383 | 0.0431 |
| N6 | 0.7591 | 0.7350 | 0.2351 | H12 | 0.1032 | 0.4696 | 0.0848 |
| N7 | 0.7973 | 0.8515 | 0.0972 | H13 | 0.0928 | 0.5219 | 0.0348 |
| N8 | 1.2859 | 0.8573 | 0.3274 | H31 | 0.5095 | 0.4019 | 0.0259 |
| N99 | 0.0738 | 0.6082 | 0.4264 | H51 | 0.4528 | 0.5808 | 0.0137 |
| C1 | 0.1526 | 0.4926 | 0.0575 | H52 | 0.3588 | 0.4886 | 0.0092 |
| C2 | 0.2084 | 0.6365 | 0.0912 | H61 | 0.5725 | 0.3920 | 0.0942 |
| C3 | 0.4102 | 0.6354 | 0.0884 | H62 | 0.5984 | 0.5065 | 0.0964 |
| C4 | 0.3663 | 0.5439 | 0.0723 | H71 | 0.3564 | 0.4120 | 0.1009 |
| C5 | 0.4211 | 0.5188 | 0.0301 | H71 | 0.3452 | 0.7134 | −0.0666 |
| C6 | 0.5364 | 0.4544 | 0.0844 | H91 | 0.4377 | 0.7157 | 0.1706 |
| C7 | 0.4114 | 0.4720 | 0.1027 | H111 | 0.3347 | 0.9853 | 0.1801 |
| C8 | 0.3163 | 0.7656 | 0.1209 | H131 | 0.1943 | 0.8325 | 0.0767 |
| C9 | 0.3869 | 0.7704 | 0.1579 | H151 | 0.5788 | 0.5242 | 0.1600 |
| C10 | 0.3885 | 0.8511 | 0.1772 | H181 | 0.1777 | 0.5143 | 0.2237 |
| C11 | 0.3279 | 0.9235 | 0.1637 | H191 | 0.2062 | 0.4772 | 0.1470 |
| C12 | 0.2599 | 0.9151 | 0.1289 | H211 | 0.6100 | 0.5093 | −0.0165 |
| C13 | 0.2497 | 0.8358 | 0.1058 | H212 | 0.6604 | 0.5555 | 0.0317 |
| C14 | 0.3977 | 0.4953 | 0.1482 | H231 | 1.0052 | 0.3318 | 0.0395 |
| C15 | 0.4920 | 0.5209 | 0.1747 | H251 | 0.6702 | 0.3385 | −0.0291 |
| C16 | 0.4760 | 0.5463 | 0.2175 | H271 | 0.7104 | 0.9736 | 0.0983 |
| C17 | 0.3626 | 0.5457 | 0.2325 | H272 | 0.8040 | 0.9563 | 0.0542 |
| C18 | 0.2653 | 0.5186 | 0.2087 | H281 | 0.8315 | 0.6433 | 0.1058 |

TABLE 7-continued

Positional Parameters for 5-[(5S, 9R)-9-(4-Cyanophenyl)-
3-(3,5-dichlorophenyl)-1-methyl-2,4-dioxo-1,3,7-
triazaspiro[4.4]non-7-ylmethyl]-thiophene-3-carboxylic
acid form AN.5-2 at −50° C.

| Atom | X | Y | Z | Atom | X | Y | Z |
|---|---|---|---|---|---|---|---|
| C19 | 0.2817 | 0.4957 | 0.1673 | H282 | 0.8885 | 0.5686 | 0.1435 |
| C20 | 0.3447 | 0.5645 | 0.2764 | H283 | 0.7361 | 0.5695 | 0.1321 |
| C21 | 0.6301 | 0.4944 | 0.0163 | H321 | 0.6633 | 0.8570 | 0.1437 |
| C22 | 0.7241 | 0.4312 | 0.0189 | H322 | 0.6678 | 0.7579 | 0.1145 |
| C23 | 0.9170 | 0.3516 | 0.0314 | H331 | 0.9748 | 0.9030 | 0.1012 |
| C24 | 0.8445 | 0.3107 | 0.0009 | H332 | 0.8800 | 0.9416 | 0.1416 |
| C25 | 0.7365 | 0.3573 | −0.0061 | H341 | 0.9806 | 0.7526 | 0.1320 |
| C26 | 0.8773 | 0.2264 | −0.0190 | H361 | 0.5926 | 0.6700 | 0.2898 |
| C27 | 0.7402 | 0.9250 | 0.0751 | H381 | 0.7774 | 0.7584 | 0.4029 |
| C28 | 0.8131 | 0.6094 | 0.1371 | H401 | 0.9327 | 0.8057 | 0.2786 |
| C29 | 0.7701 | 0.6544 | 0.2121 | H421 | 0.9857 | 0.9635 | 0.1915 |
| C30 | 0.7717 | 0.8043 | 0.2077 | H431 | 1.1158 | 0.9753 | 0.2564 |
| C31 | 0.8027 | 0.7716 | 0.1627 | H451 | 1.1859 | 0.6960 | 0.2540 |
| C32 | 0.7219 | 0.8101 | 0.1292 | H461 | 1.0744 | 0.6816 | 0.1855 |
| C33 | 0.9024 | 0.8865 | 0.1214 | H491 | 0.3411 | 0.8849 | 0.0142 |
| C34 | 0.9311 | 0.8026 | 0.1498 | H511 | 0.6916 | 0.7851 | 0.0122 |
| C35 | 0.7611 | 0.7375 | 0.2795 | H981 | 0.2470 | 0.7390 | 0.3823 |
| C36 | 0.6671 | 0.7049 | 0.3034 | H982 | 0.2876 | 0.7289 | 0.4362 |
| C37 | 0.6772 | 0.7140 | 0.3461 | H983 | 0.3275 | 0.6462 | 0.3996 |

TABLE 8

Positional Parameters for 5-[(5S, 9R)-9-(4-Cyanophenyl)-
3-(3,5-dichlorophenyl)-1-methyl-2,4-dioxo-1,3,7-
triazaspiro[4.4]non-7-ylmethyl]-thiophene-3-carboxylic
acid form M.5-2 at −50° C.

| Atom | X | Y | Z | Atom | X | Y | Z |
|---|---|---|---|---|---|---|---|
| CL12 | 0.4585 | 0.8644 | 0.2246 | C20 | 0.2533 | 0.5154 | 0.2069 |
| CL15 | 0.1640 | 1.0118 | 0.1112 | C20 | 0.7273 | 0.9278 | 0.0747 |
| CL52 | 0.5307 | 0.6942 | 0.3746 | C21 | 0.2733 | 0.4913 | 0.1659 |
| CL54 | 0.9787 | 0.7972 | 0.3661 | C22 | 0.3343 | 0.5682 | 0.2747 |
| S25 | 0.8290 | 0.4428 | 0.0542 | C23 | 0.6154 | 0.4998 | 0.0163 |
| S65 | 0.4922 | 0.9532 | 0.0560 | C24 | 0.7161 | 0.4347 | 0.0178 |
| O2 | 0.0960 | 0.6625 | 0.1002 | C26 | 0.8927 | 0.3472 | 0.0353 |
| O4 | 0.4979 | 0.6620 | 0.0908 | C27 | 0.8333 | 0.3090 | 0.0036 |
| O30 | 0.7998 | 0.1880 | −0.0398 | C28 | 0.7295 | 0.3601 | −0.0068 |
| O31 | 0.9671 | 0.1876 | −0.0025 | C29 | 0.8611 | 0.2233 | −0.0145 |
| O42 | 0.7597 | 0.5770 | 0.2261 | C41 | 0.8040 | 0.6103 | 0.1355 |
| O44 | 0.7505 | 0.8825 | 0.2182 | C42 | 0.7616 | 0.6513 | 0.2111 |
| O70 | 0.3547 | 0.7698 | −0.0450 | C44 | 0.7581 | 0.8049 | 0.2063 |
| O71 | 0.5218 | 0.6884 | −0.0339 | C45 | 0.7890 | 0.7698 | 0.1644 |
| N1 | 0.2263 | 0.5610 | 0.0729 | C46 | 0.7018 | 0.8135 | 0.1304 |
| N3 | 0.2987 | 0.6855 | 0.1001 | C48 | 0.8900 | 0.8892 | 0.1230 |
| N7 | 0.5083 | 0.4645 | 0.0372 | C49 | 0.9168 | 0.8058 | 0.1504 |
| N23 | 0.3131 | 0.5893 | 0.3097 | C50 | 0.7438 | 0.7363 | 0.2770 |
| N41 | 0.7826 | 0.6763 | 0.1704 | C51 | 0.6469 | 0.7164 | 0.3007 |
| N43 | 0.7461 | 0.7341 | 0.2331 | C52 | 0.6549 | 0.7195 | 0.3465 |
| N47 | 0.7832 | 0.8548 | 0.0990 | C53 | 0.7575 | 0.7438 | 0.3660 |
| N63 | 1.2747 | 0.8673 | 0.3264 | C54 | 0.8481 | 0.7626 | 0.3427 |
| C1 | 0.1381 | 0.4963 | 0.0602 | C55 | 0.8537 | 0.7612 | 0.2975 |
| C2 | 0.1939 | 0.6393 | 0.0908 | C56 | 0.9959 | 0.8209 | 0.1885 |
| C4 | 0.4001 | 0.6383 | 0.0882 | C57 | 1.0109 | 0.9045 | 0.2082 |
| C5 | 0.3529 | 0.5482 | 0.0717 | C58 | 1.0828 | 0.9177 | 0.2431 |
| C6 | 0.4046 | 0.5252 | 0.0294 | C59 | 1.1416 | 0.8422 | 0.2582 |
| C8 | 0.5189 | 0.4565 | 0.0835 | C60 | 1.1324 | 0.7607 | 0.2386 |
| C9 | 0.4000 | 0.4737 | 0.1012 | C61 | 1.0639 | 0.7495 | 0.2035 |
| C10 | 0.3022 | 0.7693 | 0.1223 | C62 | 1.2179 | 0.8572 | 0.2954 |
| C11 | 0.3734 | 0.7757 | 0.1591 | C64 | 0.6195 | 0.8968 | 0.0501 |
| C12 | 0.3763 | 0.8537 | 0.1792 | C66 | 0.4230 | 0.8839 | 0.0190 |
| C13 | 0.3166 | 0.9306 | 0.1665 | C67 | 0.5005 | 0.8211 | 0.0044 |
| C15 | 0.2434 | 0.9213 | 0.1308 | C68 | 0.6101 | 0.8285 | 0.0218 |
| C16 | 0.2342 | 0.8433 | 0.1064 | C69 | 0.4573 | 0.7540 | −0.0275 |
| C16 | 0.3900 | 0.4939 | 0.1478 | O98 | 0.2331 | 0.6353 | 0.3878 |
| C17 | 0.4811 | 0.5184 | 0.1726 | C99 | 0.2696 | 0.6818 | 0.4138 |
| C18 | 0.4645 | 0.5422 | 0.2153 | H311 | 0.9778 | 0.1227 | −0.0189 |
| C19 | 0.3463 | 0.5420 | 0.2302 | H471 | 0.8091 | 0.8071 | 0.0783 |

Solvent occupancy: 0.25

TABLE 9

Positional Parameters for 5-[(5S, 9R)-9-(4-Cyanophenyl)-
3-(3,5-dichlorophenyl)-1-methyl-2,4-dioxo-1,3,7-
triazaspiro[4.4]non-7-ylmethyl]-thiophene-3-carboxylic
acid form E.5-2 at −50° C.

| Atom | X | Y | Z | Atom | X | Y | Z |
|---|---|---|---|---|---|---|---|
| CL12 | 0.4771 | 0.8528 | 0.2236 | O42 | 0.7697 | 0.5814 | 0.2275 |
| CL15 | 0.1860 | 1.0015 | 0.1115 | O44 | 0.7685 | 0.8820 | 0.2163 |
| S25 | 0.8494 | 0.4416 | 0.0506 | O70 | 0.3753 | 0.7734 | −0.0446 |
| O2 | 0.1148 | 0.6599 | 0.0987 | O71 | 0.5356 | 0.6892 | −0.0332 |
| O4 | 0.5195 | 0.6573 | 0.0892 | N41 | 0.7998 | 0.6748 | 0.1706 |
| O30 | 0.8148 | 0.1871 | −0.0423 | N43 | 0.7613 | 0.7352 | 0.2335 |
| O31 | 0.9788 | 0.1892 | −0.0049 | N47 | 0.8050 | 0.8452 | 0.0976 |
| N1 | 0.2454 | 0.5606 | 0.0700 | N63 | 1.2854 | 0.8602 | 0.3267 |
| N3 | 0.3198 | 0.6804 | 0.0991 | C71 | 0.7479 | 0.9198 | 0.0758 |
| N7 | 0.5280 | 0.4638 | 0.0360 | C41 | 0.8192 | 0.6069 | 0.1386 |
| N23 | 0.3423 | 0.5799 | 0.3071 | C42 | 0.7788 | 0.6534 | 0.2115 |
| C1 | 0.1583 | 0.4968 | 0.0564 | C44 | 0.7773 | 0.8068 | 0.2064 |
| C2 | 0.2129 | 0.6346 | 0.0898 | C45 | 0.8082 | 0.7675 | 0.1639 |
| C4 | 0.4181 | 0.6344 | 0.0871 | C46 | 0.7238 | 0.8059 | 0.1297 |
| C5 | 0.3734 | 0.5468 | 0.0706 | C48 | 0.9089 | 0.8764 | 0.1224 |
| C6 | 0.4254 | 0.5215 | 0.0274 | C49 | 0.9357 | 0.7989 | 0.1504 |
| C8 | 0.5412 | 0.4546 | 0.0817 | C50 | 0.7635 | 0.7426 | 0.2781 |
| C9 | 0.4184 | 0.4704 | 0.0993 | C51 | 0.6706 | 0.7088 | 0.3019 |
| C10 | 0.3215 | 0.7628 | 0.1217 | C52 | 0.6782 | 0.7173 | 0.3457 |
| C11 | 0.3921 | 0.7671 | 0.1573 | C53 | 0.7695 | 0.7569 | 0.3651 |
| C12 | 0.3925 | 0.8464 | 0.1780 | C54 | 0.8589 | 0.7935 | 0.3396 |
| C13 | 0.3314 | 0.9212 | 0.1642 | C55 | 0.8571 | 0.7866 | 0.2970 |
| C15 | 0.2642 | 0.9124 | 0.1284 | C56 | 1.0201 | 0.8139 | 0.1870 |
| C16 | 0.2574 | 0.8342 | 0.1070 | C57 | 1.0380 | 0.8977 | 0.2046 |
| C16 | 0.4058 | 0.4921 | 0.1456 | C58 | 1.1095 | 0.9075 | 0.2394 |
| C17 | 0.5017 | 0.5147 | 0.1705 | C59 | 1.1616 | 0.8358 | 0.2573 |
| C18 | 0.4863 | 0.5361 | 0.2124 | C60 | 1.1489 | 0.7517 | 0.2393 |
| C19 | 0.3741 | 0.5358 | 0.2291 | C61 | 1.0793 | 0.7434 | 0.2029 |
| C20 | 0.2757 | 0.5137 | 0.2050 | C62 | 1.2340 | 0.8493 | 0.2941 |
| C21 | 0.2930 | 0.4905 | 0.1638 | C64 | 0.6402 | 0.8898 | 0.0499 |
| C22 | 0.3590 | 0.5596 | 0.2728 | C66 | 0.4416 | 0.8837 | 0.0207 |
| C23 | 0.6367 | 0.4968 | 0.0146 | C67 | 0.5155 | 0.8218 | 0.0052 |
| C24 | 0.7341 | 0.4324 | 0.0160 | C68 | 0.6295 | 0.8268 | 0.0221 |
| C26 | 0.9142 | 0.3491 | 0.0332 | C69 | 0.4785 | 0.7536 | −0.0263 |
| C27 | 0.8518 | 0.3094 | 0.0020 | O100 | 0.2388 | 0.6744 | 0.4062 |
| C28 | 0.7464 | 0.3581 | −0.0081 | C99 | 0.0637 | 0.6040 | 0.4251 |
| C29 | 0.8801 | 0.2238 | −0.0165 | C98 | 0.1414 | 0.6354 | 0.3934 |
| CL52 | 0.5665 | 0.6733 | 0.3752 | H71 | 0.5119 | 0.4040 | 0.0234 |
| CL54 | 0.9777 | 0.8477 | 0.3625 | H701 | 0.3517 | 0.7208 | −0.0664 |
| S65 | 0.5118 | 0.9480 | 0.0567 | — | — | — | — |

Solvent occupancy: 0.75

TABLE 10

Positional Parameters for 5-[(5S, 9R)-9-(4-Cyanophenyl)-
3-(3,5-dichlorophenyl)-1-methyl-2,4-dioxo-1,3,7-
triazaspiro[4.4]non-7-ylmethyl]-thiophene-3-carboxylic
acid form IPA.5-2 at −50° C.

| Atom | X | Y | Z | Atom | X | Y | Z |
|---|---|---|---|---|---|---|---|
| CL3 | 0.4892 | 0.8390 | 0.2267 | O42 | 0.7858 | 0.5878 | 0.2307 |
| CL5 | 0.2082 | 0.9940 | 0.1128 | O44 | 0.7830 | 0.8803 | 0.2151 |
| S25 | 0.8606 | 0.4400 | 0.0463 | O70 | 0.3897 | 0.7713 | −0.0454 |
| O2 | 0.1267 | 0.6584 | 0.1000 | O71 | 0.5486 | 0.6909 | −0.0338 |
| O4 | 0.5323 | 0.6550 | 0.0885 | N41 | 0.8139 | 0.6745 | 0.1727 |
| O30 | 0.8108 | 0.1806 | −0.0392 | N43 | 0.7778 | 0.7356 | 0.2345 |
| O31 | 0.9867 | 0.1900 | −0.0084 | N47 | 0.8178 | 0.8451 | 0.0983 |
| N1 | 0.2551 | 0.5591 | 0.0709 | N63 | 1.2965 | 0.8448 | 0.3290 |
| N3 | 0.3330 | 0.6779 | 0.0994 | C41 | 0.8343 | 0.6067 | 0.1424 |
| N7 | 0.5347 | 0.4624 | 0.0346 | C42 | 0.7919 | 0.6563 | 0.2139 |
| N23 | 0.3675 | 0.5651 | 0.3084 | C44 | 0.7924 | 0.8037 | 0.2077 |
| C1 | 0.1677 | 0.4980 | 0.0544 | C45 | 0.8212 | 0.7664 | 0.1644 |
| C2 | 0.2266 | 0.6332 | 0.0902 | C46 | 0.7415 | 0.8031 | 0.1284 |
| C4 | 0.4270 | 0.6340 | 0.0866 | C48 | 0.9256 | 0.8739 | 0.1233 |
| C5 | 0.3830 | 0.5454 | 0.0698 | C49 | 0.9508 | 0.7953 | 0.1503 |
| C6 | 0.4346 | 0.5242 | 0.0244 | C65 | 0.6557 | 0.8878 | 0.0519 |
| C8 | 0.5517 | 0.4545 | 0.0805 | C50 | 0.7749 | 0.7459 | 0.2800 |
| C9 | 0.4267 | 0.4701 | 0.0979 | C51 | 0.6781 | 0.7088 | 0.3026 |

TABLE 10-continued

Positional Parameters for 5-[(5S, 9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid form IPA.5-2 at −50° C.

| Atom | X | Y | Z | Atom | X | Y | Z |
|---|---|---|---|---|---|---|---|
| C10 | 0.3368 | 0.7578 | 0.1220 | C52 | 0.6882 | 0.7245 | 0.3456 |
| C11 | 0.4016 | 0.7597 | 0.1585 | C53 | 0.7776 | 0.7703 | 0.3675 |
| C12 | 0.4057 | 0.8386 | 0.1784 | C54 | 0.8619 | 0.8036 | 0.3429 |
| C13 | 0.3512 | 0.9098 | 0.1654 | C55 | 0.8646 | 0.7912 | 0.2987 |
| C14 | 0.2831 | 0.9055 | 0.1289 | C56 | 1.0343 | 0.8061 | 0.1881 |
| C15 | 0.2741 | 0.8281 | 0.1067 | C57 | 1.0524 | 0.8883 | 0.2063 |
| C16 | 0.4182 | 0.4935 | 0.1456 | C58 | 1.1265 | 0.8997 | 0.2426 |
| C17 | 0.5148 | 0.5116 | 0.1711 | C59 | 1.1757 | 0.8237 | 0.2572 |
| C18 | 0.5011 | 0.5340 | 0.2133 | C60 | 1.1613 | 0.7426 | 0.2407 |
| C19 | 0.3905 | 0.5321 | 0.2293 | C61 | 1.0894 | 0.7348 | 0.2052 |
| C20 | 0.2906 | 0.5107 | 0.2061 | C62 | 1.2451 | 0.8362 | 0.2964 |
| C21 | 0.3063 | 0.4885 | 0.1634 | C64 | 0.7626 | 0.9128 | 0.0757 |
| C22 | 0.3747 | 0.5498 | 0.2737 | C66 | 0.4562 | 0.8795 | 0.0221 |
| C23 | 0.6414 | 0.4918 | 0.0104 | C67 | 0.5272 | 0.8220 | 0.0067 |
| C24 | 0.7416 | 0.4297 | 0.0145 | C68 | 0.6424 | 0.8249 | 0.0243 |
| C26 | 0.9240 | 0.3480 | 0.0300 | C69 | 0.4907 | 0.7534 | −0.0248 |
| C27 | 0.8572 | 0.3069 | 0.0006 | C95 | 0.2488 | 0.6697 | 0.4087 |
| C28 | 0.7498 | 0.3541 | −0.0093 | C96 | 0.0549 | 0.6010 | 0.4213 |
| C29 | 0.8822 | 0.2198 | −0.0176 | C97 | 0.1209 | 0.6407 | 0.3902 |
| CL52 | 0.5711 | 0.6808 | 0.3759 | C98 | 0.1230 | 0.6032 | 0.3555 |
| CL54 | 0.9771 | 0.8607 | 0.3643 | H71 | 0.5134 | 0.4038 | 0.0227 |
| S4 | 0.5262 | 0.9445 | 0.0574 | H701 | 0.3681 | 0.7182 | −0.0665 |

Solvent occupancy: 0.8; solvent disordered

TABLE 11

Positional Parameters for 5-[(5S, 9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid form PR.5-2 at −50° C.

| Atom | X | Y | Z | Atom | X | Y | Z |
|---|---|---|---|---|---|---|---|
| CL12 | 0.4833 | 0.8488 | 0.2241 | C21 | 0.3019 | 0.4922 | 0.1634 |
| CL15 | 0.2019 | 1.0009 | 0.1102 | C22 | 0.3751 | 0.5586 | 0.2706 |
| CL52 | 0.5688 | 0.6863 | 0.3752 | C23 | 0.6408 | 0.4968 | 0.0143 |
| CL54 | 0.9782 | 0.8612 | 0.3629 | C24 | 0.7358 | 0.4291 | 0.0143 |
| S25 | 0.8549 | 0.4415 | 0.0484 | C26 | 0.9213 | 0.3482 | 0.0300 |
| S65 | 0.5248 | 0.9468 | 0.0563 | C27 | 0.8523 | 0.3079 | 0.0020 |
| O2 | 0.1214 | 0.6620 | 0.0985 | C28 | 0.7471 | 0.3543 | −0.0079 |
| O4 | 0.5274 | 0.6564 | 0.0894 | C29 | 0.8767 | 0.2216 | −0.0164 |
| O30 | 0.8114 | 0.1832 | −0.0398 | C41 | 0.8289 | 0.6095 | 0.1418 |
| O31 | 0.9797 | 0.1901 | −0.0045 | C42 | 0.7840 | 0.6570 | 0.2145 |
| O42 | 0.7772 | 0.5888 | 0.2313 | C44 | 0.7868 | 0.8081 | 0.2064 |
| O44 | 0.7800 | 0.8861 | 0.2148 | C45 | 0.8194 | 0.7699 | 0.1639 |
| O70 | 0.3864 | 0.7759 | −0.0452 | C46 | 0.7362 | 0.8055 | 0.1300 |
| O71 | 0.5440 | 0.6887 | −0.0339 | C48 | 0.9234 | 0.8726 | 0.1211 |
| O99 | 0.3061 | 0.6127 | 0.3990 | C49 | 0.9438 | 0.7972 | 0.1512 |
| N1 | 0.2518 | 0.5617 | 0.0695 | C50 | 0.7689 | 0.7478 | 0.2787 |
| N3 | 0.3257 | 0.6815 | 0.0982 | C51 | 0.6759 | 0.7165 | 0.3022 |
| N7 | 0.5314 | 0.4633 | 0.0344 | C52 | 0.6861 | 0.7250 | 0.3467 |
| N23 | 0.3672 | 0.5774 | 0.3063 | C53 | 0.7751 | 0.7723 | 0.3646 |
| N41 | 0.8035 | 0.6774 | 0.1732 | C54 | 0.8629 | 0.8048 | 0.3400 |
| N43 | 0.7744 | 0.7430 | 0.2339 | C55 | 0.8613 | 0.7949 | 0.2962 |
| N47 | 0.8164 | 0.8431 | 0.0986 | C56 | 1.0303 | 0.8122 | 0.1885 |
| N63 | 1.2934 | 0.8524 | 0.3257 | C57 | 1.0500 | 0.8941 | 0.2051 |
| C1 | 0.1617 | 0.5001 | 0.0555 | C58 | 1.1179 | 0.9036 | 0.2406 |
| C2 | 0.2214 | 0.6349 | 0.0902 | C59 | 1.1716 | 0.8315 | 0.2575 |
| C4 | 0.4255 | 0.6356 | 0.0859 | C60 | 1.1559 | 0.7459 | 0.2414 |
| C5 | 0.3811 | 0.5464 | 0.0696 | C61 | 1.0867 | 0.7374 | 0.2050 |
| C6 | 0.4314 | 0.5263 | 0.0266 | C62 | 1.2422 | 0.8406 | 0.2950 |
| C8 | 0.5476 | 0.4554 | 0.0810 | C64 | 0.6526 | 0.8877 | 0.0510 |
| C9 | 0.4178 | 0.4725 | 0.0980 | C66 | 0.4535 | 0.8828 | 0.0208 |
| C10 | 0.3298 | 0.7606 | 0.1205 | C67 | 0.5254 | 0.8239 | 0.0050 |
| C11 | 0.3970 | 0.7661 | 0.1567 | C68 | 0.6397 | 0.8238 | 0.0219 |
| C12 | 0.4018 | 0.8446 | 0.1762 | C69 | 0.4864 | 0.7529 | −0.0264 |
| C13 | 0.3430 | 0.9174 | 0.1635 | C71 | 0.7632 | 0.9155 | −0.0742 |
| C15 | 0.2789 | 0.9077 | 0.1271 | C96 | 0.0793 | 0.6269 | 0.3475 |
| C16 | 0.2682 | 0.8302 | 0.1055 | C97 | 0.2176 | 0.6740 | 0.4050 |
| C16 | 0.4156 | 0.4930 | 0.1449 | C98 | 0.0957 | 0.6373 | 0.3957 |

TABLE 11-continued

Positional Parameters for 5-[(5S, 9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid form PR.5-2 at −50° C.

| Atom | X | Y | Z | Atom | X | Y | Z |
|---|---|---|---|---|---|---|---|
| C17 | 0.5105 | 0.5146 | 0.1706 | H311 | 0.9903 | 0.1256 | −0.0187 |
| C18 | 0.5009 | 0.5341 | 0.2117 | H701 | 0.3603 | 0.7245 | −0.0672 |
| C19 | 0.3867 | 0.5356 | 0.2284 | H991 | 0.3193 | 0.6051 | 0.3632 |
| C20 | 0.2865 | 0.5174 | 0.2048 | — | — | — | — |

TABLE 12

Positional Parameters for 5-[(5S, 9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid form NMP.5-2 at −50°

| Atom | X | Y | Z | Atom | X | Y | Z |
|---|---|---|---|---|---|---|---|
| CL1 | 0.4926 | 0.8451 | 0.2236 | O7 | 0.3834 | 0.7646 | −0.0449 |
| CL2 | 0.2167 | 0.9906 | 0.1066 | O8 | 0.5475 | 0.6896 | −0.0329 |
| S1 | 0.8590 | 0.4282 | 0.0478 | N5 | 0.8193 | 0.6875 | 0.1701 |
| O1 | 0.1288 | 0.6610 | 0.0992 | N6 | 0.7853 | 0.7488 | 0.2316 |
| O2 | 0.5371 | 0.6547 | 0.0891 | N7 | 0.8088 | 0.8537 | 0.0964 |
| O3 | 0.8099 | 0.1839 | −0.0439 | N8 | 1.3003 | 0.8700 | 0.3211 |
| O4 | 0.9910 | 0.1936 | −0.0151 | C27 | 0.7471 | 0.9220 | 0.0745 |
| N1 | 0.2592 | 0.5614 | 0.0726 | C28 | 0.8383 | 0.6229 | 0.1386 |
| N2 | 0.3348 | 0.6786 | 0.0988 | C29 | 0.7999 | 0.6687 | 0.2109 |
| N3 | 0.5368 | 0.4627 | 0.0369 | C30 | 0.7933 | 0.8159 | 0.2044 |
| N4 | 0.3773 | 0.5662 | 0.3114 | C31 | 0.8222 | 0.7785 | 0.1616 |
| C1 | 0.1694 | 0.5015 | 0.0573 | C32 | 0.7329 | 0.8094 | 0.1284 |
| C2 | 0.2275 | 0.6347 | 0.0909 | C33 | 0.9161 | 0.8860 | 0.1194 |
| C3 | 0.4335 | 0.6330 | 0.0870 | C34 | 0.9475 | 0.8110 | 0.1468 |
| C4 | 0.3860 | 0.5473 | 0.0714 | C35 | 0.7791 | 0.7578 | 0.2762 |
| C5 | 0.4370 | 0.5220 | 0.0287 | C36 | 0.6907 | 0.7216 | 0.2995 |
| C6 | 0.5563 | 0.4591 | 0.0834 | C37 | 0.6916 | 0.7345 | 0.3421 |
| C7 | 0.4309 | 0.4760 | 0.1008 | C38 | 0.7781 | 0.7815 | 0.3628 |
| C8 | 0.3409 | 0.7578 | 0.1206 | C39 | 0.8656 | 0.8175 | 0.3375 |
| C9 | 0.4080 | 0.7619 | 0.1566 | C40 | 0.8707 | 0.8067 | 0.2945 |
| C10 | 0.4144 | 0.8382 | 0.1769 | C41 | 1.0326 | 0.8271 | 0.1828 |
| C11 | 0.3561 | 0.9110 | 0.1617 | C42 | 1.0496 | 0.9062 | 0.2002 |
| C12 | 0.2884 | 0.9021 | 0.1264 | C43 | 1.1194 | 0.9181 | 0.2353 |
| C13 | 0.2779 | 0.8265 | 0.1046 | C44 | 1.1765 | 0.8469 | 0.2530 |
| C14 | 0.4240 | 0.4980 | 0.1475 | C45 | 1.1673 | 0.7669 | 0.2343 |
| C15 | 0.5212 | 0.5214 | 0.1708 | C46 | 1.0951 | 0.7579 | 0.1997 |
| C16 | 0.5091 | 0.5416 | 0.2135 | C47 | 1.2501 | 0.8588 | 0.2906 |
| C17 | 0.3966 | 0.5371 | 0.2314 | C48 | 0.6402 | 0.8902 | 0.0493 |
| C18 | 0.2968 | 0.5155 | 0.2081 | C49 | 0.4441 | 0.8803 | 0.0163 |
| C19 | 0.3110 | 0.4968 | 0.1663 | C50 | 0.5191 | 0.8184 | 0.0038 |
| C20 | 0.3826 | 0.5540 | 0.2762 | C51 | 0.6327 | 0.8237 | 0.0230 |
| C21 | 0.6439 | 0.4875 | 0.0124 | C52 | 0.4823 | 0.7517 | −0.0268 |
| C22 | 0.7390 | 0.4214 | 0.0136 | O93 | 0.0710 | 0.5720 | 0.4456 |
| C23 | 0.9227 | 0.3387 | 0.0284 | N99 | 0.2148 | 0.6495 | 0.4122 |
| C24 | 0.8539 | 0.3032 | −0.0023 | C97 | 0.0338 | 0.6392 | 0.3787 |
| C25 | 0.7496 | 0.3516 | −0.0108 | C98 | 0.1032 | 0.6156 | 0.4158 |
| C26 | 0.8816 | 0.2213 | −0.0228 | C95 | 0.2263 | 0.7040 | 0.3751 |
| CL3 | 0.5808 | 0.6875 | 0.3721 | C94 | 0.3058 | 0.6478 | 0.4438 |
| CL4 | 0.9758 | 0.8776 | 0.3609 | C96 | 0.1250 | 0.6744 | 0.3462 |
| S2 | 0.5106 | 0.9465 | 0.0513 | H41 | 0.9987 | 0.1283 | −0.0255 |
| O5 | 0.7967 | 0.6018 | 0.2283 | H71 | 0.8349 | 0.8105 | 0.0750 |
| O6 | 0.7828 | 0.8898 | 0.2124 | — | — | — | — |

TABLE 13

Positional Parameters for 5-[(5S, 9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid form THF.5-2 at −50°

| Atom | X | Y | Z | Atom | X | Y | Z |
|---|---|---|---|---|---|---|---|
| CL2 | 0.5727 | 0.6611 | 0.3759 | C42 | 0.5110 | 0.5167 | 0.1729 |
| CL3 | 0.1919 | 0.9945 | 0.1136 | C43 | 0.4937 | 0.5362 | 0.2121 |
| CL4 | 0.4824 | 0.8407 | 0.2252 | C44 | 0.3751 | 0.5305 | 0.2318 |
| S5 | 0.8645 | 0.4424 | 0.0474 | C45 | 0.2880 | 0.5092 | 0.2059 |

TABLE 13-continued

Positional Parameters for 5-[(5S, 9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid form THF.5-2 at −50°

| Atom | X | Y | Z | Atom | X | Y | Z |
|---|---|---|---|---|---|---|---|
| S6 | 0.5127 | 0.9391 | 0.0591 | C46 | 0.3015 | 0.4917 | 0.1660 |
| O7 | 0.1229 | 0.6561 | 0.0991 | C47 | 0.3652 | 0.5497 | 0.2759 |
| O8 | 0.5287 | 0.6539 | 0.0898 | C48 | 0.6462 | 0.4967 | 0.0133 |
| O9 | 0.8222 | 0.1905 | −0.0447 | C49 | 0.7462 | 0.4290 | 0.0153 |
| O10 | 0.9962 | 0.1980 | −0.0112 | C50 | 0.9305 | 0.3496 | 0.0300 |
| O11 | 0.7823 | 0.5858 | 0.2288 | C51 | 0.8665 | 0.3097 | −0.0022 |
| O12 | 0.7783 | 0.8759 | 0.2164 | C52 | 0.7519 | 0.3622 | −0.0096 |
| O13 | 0.3811 | 0.7764 | −0.0458 | C53 | 0.8881 | 0.2290 | −0.0181 |
| O14 | 0.5427 | 0.6898 | −0.0354 | C54 | 0.7539 | 0.9174 | 0.0781 |
| O15 | 0.1794 | 0.6070 | 0.4484 | C55 | 0.8246 | 0.6033 | 0.1428 |
| N16 | 0.2553 | 0.5598 | 0.0701 | C56 | 0.7896 | 0.6477 | 0.2102 |
| N17 | 0.3273 | 0.6784 | 0.1007 | C57 | 0.7820 | 0.8028 | 0.2108 |
| N18 | 0.5369 | 0.4621 | 0.0373 | C58 | 0.8121 | 0.7636 | 0.1674 |
| N19 | 0.3527 | 0.5615 | 0.3098 | C59 | 0.7304 | 0.7980 | 0.1309 |
| N20 | 0.8066 | 0.6691 | 0.1717 | C60 | 0.9104 | 0.8722 | 0.1217 |
| N21 | 0.7732 | 0.7253 | 0.2321 | C61 | 0.9433 | 0.7953 | 0.1493 |
| N22 | 0.8057 | 0.8420 | 0.0991 | C62 | 1.0212 | 0.8100 | 0.1898 |
| N23 | 1.2928 | 0.8597 | 0.3265 | C63 | 1.0323 | 0.8933 | 0.2052 |
| C24 | 0.2700 | 0.9039 | 0.1306 | C64 | 1.1104 | 0.8998 | 0.2398 |
| C25 | 0.3365 | 0.9106 | 0.1672 | C65 | 1.1656 | 0.8276 | 0.2576 |
| C26 | 0.3939 | 0.8442 | 0.1772 | C66 | 1.1591 | 0.7461 | 0.2415 |
| C27 | 0.3274 | 0.7525 | 0.1214 | C67 | 1.0832 | 0.7407 | 0.2039 |
| C28 | 0.3984 | 0.7639 | 0.1580 | C68 | 1.2342 | 0.8435 | 0.2950 |
| C29 | 0.2606 | 0.8289 | 0.1083 | C69 | 0.6395 | 0.8811 | 0.0499 |
| C30 | 0.1692 | 0.4825 | 0.0529 | C70 | 0.4435 | 0.8799 | 0.0221 |
| C31 | 0.2258 | 0.6308 | 0.0875 | C71 | 0.5184 | 0.8219 | 0.0054 |
| C32 | 0.2488 | 0.6981 | 0.3980 | C72 | 0.6350 | 0.8191 | 0.0234 |
| C33 | 0.4207 | 0.6313 | 0.0846 | C73 | 0.4845 | 0.7548 | −0.0244 |
| C34 | 0.1502 | 0.6531 | 0.3793 | C74 | 0.6779 | 0.7007 | −0.3038 |
| C35 | 0.2849 | 0.6511 | 0.4360 | C75 | 0.6822 | 0.7098 | 0.3451 |
| C36 | 0.3841 | 0.5490 | 0.0698 | C76 | 0.7683 | 0.7487 | 0.3672 |
| C37 | 0.4332 | 0.5250 | 0.0264 | C77 | 0.8559 | 0.7901 | 0.3401 |
| C38 | 0.0870 | 0.6187 | 0.4172 | C78 | 0.8561 | 0.7844 | 0.2989 |
| C39 | 0.5534 | 0.4625 | 0.0809 | C79 | 0.7674 | 0.7383 | 0.2763 |
| C40 | 0.4253 | 0.4763 | 0.0995 | H101 | 1.0023 | 0.1302 | −0.0231 |
| C41 | 0.4155 | 0.4921 | 0.1423 | H131 | 0.3597 | 0.7212 | −0.0665 |

TABLE 14

Positional Parameters for 5-[(5S, 9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid form (S)-2Bu.5-2 at −50° C.

| Atom | X | Y | Z | Atom | X | Y | Z |
|---|---|---|---|---|---|---|---|
| CL1 | 0.4965 | 0.8384 | 0.2253 | O6 | 0.7907 | 0.8838 | 0.2140 |
| CL2 | 0.2226 | 0.9912 | 0.1104 | O7 | 0.4005 | 0.7709 | −0.0448 |
| S1 | 0.8694 | 0.4394 | 0.0437 | O8 | 0.5600 | 0.6887 | −0.0339 |
| O1 | 0.1364 | 0.6578 | 0.0991 | N5 | 0.8197 | 0.6789 | 0.1726 |
| O2 | 0.5436 | 0.6539 | 0.0879 | N6 | 0.7868 | 0.7422 | 0.2334 |
| O3 | 0.8180 | 0.1837 | −0.0416 | N7 | 0.8298 | 0.8435 | 0.0988 |
| O4 | 0.9891 | 0.1872 | −0.0065 | N8 | 1.3015 | 0.8544 | 0.3262 |
| N1 | 0.2645 | 0.5608 | 0.0698 | C27 | 0.7719 | 0.9129 | 0.0735 |
| N2 | 0.3403 | 0.6771 | 0.0990 | C28 | 0.8428 | 0.6131 | 0.1418 |
| N3 | 0.5420 | 0.4631 | 0.0335 | C29 | 0.7997 | 0.6632 | 0.2130 |
| N4 | 0.3774 | 0.5723 | 0.3053 | C30 | 0.7977 | 0.8087 | 0.2056 |
| C1 | 0.1750 | 0.5002 | 0.0555 | C31 | 0.8303 | 0.7700 | 0.1640 |
| C2 | 0.2337 | 0.6342 | 0.0894 | C32 | 0.7497 | 0.8047 | 0.1295 |
| C3 | 0.4378 | 0.6314 | 0.0865 | C33 | 0.9342 | 0.8739 | 0.1221 |
| C4 | 0.3913 | 0.5464 | 0.0694 | C34 | 0.9605 | 0.7985 | 0.1505 |
| C5 | 0.4436 | 0.5239 | 0.0258 | C35 | 0.7789 | 0.7538 | 0.2775 |
| C6 | 0.5646 | 0.4566 | 0.0797 | C36 | 0.6899 | 0.7165 | 0.3013 |
| C7 | 0.4358 | 0.4710 | 0.0976 | C37 | 0.6913 | 0.7281 | 0.3437 |
| C8 | 0.3469 | 0.7549 | 0.1213 | C38 | 0.7795 | 0.7764 | 0.3632 |
| C9 | 0.4139 | 0.7580 | 0.1576 | C39 | 0.8663 | 0.8109 | 0.3397 |
| C10 | 0.4167 | 0.8352 | 0.1796 | C40 | 0.8703 | 0.8013 | 0.2970 |
| C11 | 0.3613 | 0.9069 | 0.1664 | C41 | 1.0421 | 0.8128 | 0.1869 |
| C12 | 0.2959 | 0.9014 | 0.1291 | C42 | 1.0601 | 0.8935 | 0.2040 |
| C13 | 0.2845 | 0.8257 | 0.1063 | C43 | 1.1320 | 0.9033 | 0.2398 |
| C14 | 0.4292 | 0.4918 | 0.1431 | C44 | 1.1814 | 0.8328 | 0.2576 |

TABLE 14-continued

Positional Parameters for 5-[(5S, 9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid form (S)-2Bu.5-2 at −50° C.

| Atom | X | Y | Z | Atom | X | Y | Z |
|---|---|---|---|---|---|---|---|
| C15 | 0.5277 | 0.5144 | 0.1673 | C45 | 1.1690 | 0.7509 | 0.2405 |
| C16 | 0.5108 | 0.5350 | 0.2104 | C46 | 1.0978 | 0.7426 | 0.2046 |
| C17 | 0.4007 | 0.5336 | 0.2267 | C47 | 1.2492 | 0.8433 | 0.2955 |
| C18 | 0.3024 | 0.5090 | 0.2032 | C48 | 0.6665 | 0.8838 | 0.0507 |
| C19 | 0.3177 | 0.4896 | 0.1634 | C49 | 0.4683 | 0.8771 | 0.0205 |
| C20 | 0.3890 | 0.5544 | 0.2705 | C50 | 0.5381 | 0.8183 | 0.0048 |
| C21 | 0.6501 | 0.4912 | 0.0103 | C51 | 0.6533 | 0.8221 | 0.0219 |
| C22 | 0.7477 | 0.4258 | 0.0119 | C52 | 0.5006 | 0.7529 | −0.0264 |
| C23 | 0.9313 | 0.3476 | 0.0272 | C98 | 0.2372 | 0.6911 | 0.4010 |
| C24 | 0.8650 | 0.3066 | −0.0004 | C99 | 0.3012 | 0.6565 | 0.4313 |
| C25 | 0.7552 | 0.3523 | −0.0108 | C97 | 0.1404 | 0.6489 | 0.3798 |
| C26 | 0.8896 | 0.2199 | −0.0185 | O95 | 0.1745 | 0.5773 | 0.3621 |
| CL3 | 0.5755 | 0.6847 | 0.3726 | C96 | 0.0428 | 0.6307 | 0.4025 |
| CL4 | 0.9772 | 0.8690 | 0.3631 | H951 | 0.2506 | 0.5903 | 0.3416 |
| S2 | 0.5360 | 0.9397 | 0.0560 | H7 | 0.3750 | 0.7257 | −0.0655 |
| O5 | 0.7941 | 0.5941 | 0.2304 | H4 | 0.9993 | 0.1242 | −0.0202 |

Solvent occupancy: 0.7

TABLE 15

Positional Parameters for 5-[(5S, 9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid form (R)-2BU.5-2 at −50° C.

| Atom | X | Y | Z | Atom | X | Y | Z |
|---|---|---|---|---|---|---|---|
| CL1 | 0.4953 | 0.8466 | 0.2221 | O6 | 0.7920 | 0.8890 | 0.2118 |
| CL2 | 0.2175 | 0.9990 | 0.1084 | O7 | 0.4036 | 0.7758 | −0.0456 |
| S1 | 0.8717 | 0.4379 | 0.0482 | O8 | 0.5600 | 0.6891 | −0.0341 |
| O1 | 0.1365 | 0.6585 | 0.0984 | N5 | 0.8190 | 0.6804 | 0.1715 |
| O2 | 0.5441 | 0.6567 | 0.0886 | N6 | 0.7861 | 0.7449 | 0.2313 |
| O3 | 0.8323 | 0.1904 | −0.0447 | N7 | 0.8333 | 0.8428 | 0.0969 |
| O4 | 0.9923 | 0.1849 | −0.0036 | N8 | 1.2971 | 0.8523 | 0.3226 |
| N1 | 0.2675 | 0.5601 | 0.0687 | C27 | 0.7794 | 0.9132 | 0.0726 |
| N2 | 0.3418 | 0.6803 | 0.0982 | C28 | 0.8403 | 0.6121 | 0.1408 |
| N3 | 0.5503 | 0.4668 | 0.0331 | C29 | 0.7973 | 0.6634 | 0.2103 |
| N4 | 0.3665 | 0.5772 | 0.2999 | C30 | 0.7991 | 0.8123 | 0.2035 |
| C1 | 0.1814 | 0.4973 | 0.0561 | C31 | 0.8310 | 0.7742 | 0.1636 |
| C2 | 0.2349 | 0.6337 | 0.0881 | C32 | 0.7485 | 0.8088 | 0.1294 |
| C3 | 0.4391 | 0.6337 | 0.0851 | C33 | 0.9379 | 0.8748 | 0.1212 |
| C4 | 0.3971 | 0.5473 | 0.0681 | C34 | 0.9614 | 0.7997 | 0.1498 |
| C5 | 0.4485 | 0.5278 | 0.0265 | C35 | 0.7794 | 0.7552 | 0.2755 |
| C6 | 0.5650 | 0.4581 | 0.0800 | C36 | 0.6870 | 0.7175 | 0.2963 |
| C7 | 0.4397 | 0.4722 | 0.0961 | C37 | 0.6851 | 0.7274 | 0.3388 |
| C8 | 0.3454 | 0.7589 | 0.1190 | C38 | 0.7746 | 0.7768 | 0.3597 |
| C9 | 0.4123 | 0.7618 | 0.1550 | C39 | 0.8642 | 0.8100 | 0.3367 |
| C10 | 0.4171 | 0.8422 | 0.1760 | C40 | 0.8687 | 0.8018 | 0.2941 |
| C11 | 0.3612 | 0.9150 | 0.1626 | C41 | 1.0426 | 0.8139 | 0.1853 |
| C12 | 0.2928 | 0.9074 | 0.1255 | C42 | 1.0621 | 0.8959 | 0.2025 |
| C13 | 0.2829 | 0.8290 | 0.1042 | C43 | 1.1291 | 0.9039 | 0.2383 |
| C14 | 0.4305 | 0.4929 | 0.1414 | C44 | 1.1827 | 0.8324 | 0.2572 |
| C15 | 0.5261 | 0.5142 | 0.1657 | C45 | 1.1665 | 0.7509 | 0.2393 |
| C16 | 0.5097 | 0.5340 | 0.2074 | C46 | 1.1027 | 0.7417 | 0.2046 |
| C17 | 0.3979 | 0.5341 | 0.2238 | C47 | 1.2498 | 0.8428 | 0.2946 |
| C18 | 0.2991 | 0.5112 | 0.2002 | C48 | 0.6737 | 0.8853 | 0.0480 |
| C19 | 0.3165 | 0.4906 | 0.1601 | C49 | 0.4687 | 0.8794 | 0.0198 |
| C20 | 0.3821 | 0.5586 | 0.2661 | C50 | 0.5420 | 0.8197 | 0.0036 |
| C21 | 0.6590 | 0.4957 | 0.0123 | C51 | 0.6577 | 0.8206 | 0.0203 |
| C22 | 0.7541 | 0.4312 | 0.0135 | C52 | 0.5045 | 0.7549 | −0.0270 |
| C23 | 0.9378 | 0.3464 | 0.0298 | O95 | 0.3165 | 0.5780 | 0.3815 |
| C24 | 0.8746 | 0.3084 | −0.0011 | C97 | 0.2637 | 0.6599 | 0.3932 |
| C25 | 0.7681 | 0.3578 | −0.0112 | C98 | 0.1240 | 0.6499 | 0.3904 |
| C26 | 0.8989 | 0.2227 | −0.0188 | C99 | 0.0818 | 0.6321 | 0.3511 |
| CL3 | 0.5716 | 0.6815 | 0.3668 | C96 | 0.3077 | 0.6792 | 0.4338 |
| CL4 | 0.9755 | 0.8693 | 0.3604 | H711 | 0.3788 | 0.7242 | −0.0666 |
| S2 | 0.5415 | 0.9432 | 0.0549 | H951 | 0.3357 | 0.5781 | 0.3488 |
| O5 | 0.7900 | 0.5938 | 0.2277 | H31 | 0.5290 | 0.4057 | 0.0213 |

Solvent occupancy: 0.8

TABLE 16

Positional Parameters for 5-[(5S, 9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid form T1E.5-2 at +90°

| Atom | X | Y | Z | Atom | X | Y | Z |
|---|---|---|---|---|---|---|---|
| CL1 | 0.4488 | 0.8557 | 0.2276 | C17 | 0.3439 | 0.5325 | 0.2330 |
| CL2 | 0.5042 | 0.7019 | 0.3765 | C18 | 0.2497 | 0.5087 | 0.2085 |
| CL3 | 0.1594 | 1.0014 | 0.1128 | C19 | 0.2627 | 0.4861 | 0.1656 |
| CL4 | 0.9633 | 0.7474 | 0.3759 | C20 | 0.3215 | 0.5514 | 0.2770 |
| S1 | 0.8184 | 0.4427 | 0.0526 | C21 | 0.6049 | 0.4965 | 0.0160 |
| S2 | 0.4869 | 0.9478 | 0.0595 | C22 | 0.7018 | 0.4300 | 0.0183 |
| O1 | 0.0889 | 0.6591 | 0.1009 | C23 | 0.8794 | 0.3434 | 0.0375 |
| O2 | 0.7783 | 0.1800 | −0.0359 | C24 | 0.8177 | 0.3044 | 0.0083 |
| O3 | 0.4889 | 0.6565 | 0.0926 | C25 | 0.7135 | 0.3527 | −0.0033 |
| O4 | 0.9430 | 0.1823 | 0.0020 | C26 | 0.8465 | 0.2159 | −0.0099 |
| O5 | 0.7546 | 0.5675 | 0.2271 | C27 | 0.7207 | 0.9211 | 0.0799 |
| O6 | 0.5121 | 0.6904 | −0.0341 | C28 | 0.7996 | 0.6014 | 0.1375 |
| O8 | 0.7402 | 0.8666 | 0.2237 | C29 | 0.7592 | 0.6432 | 0.2120 |
| O7 | 0.3527 | 0.7720 | −0.0442 | C30 | 0.7510 | 0.7912 | 0.2116 |
| N1 | 0.2196 | 0.5621 | 0.0719 | C31 | 0.7859 | 0.7592 | 0.1670 |
| N2 | 0.2920 | 0.6835 | 0.1021 | C32 | 0.7019 | 0.7998 | 0.1335 |
| N3 | 0.4982 | 0.4646 | 0.0363 | C33 | 0.8813 | 0.8755 | 0.1268 |
| N4 | 0.3063 | 0.5685 | 0.3139 | C34 | 0.9077 | 0.7962 | 0.1547 |
| N5 | 0.7802 | 0.6660 | 0.1729 | C35 | 0.7356 | 0.7185 | 0.2820 |
| N6 | 0.7407 | 0.7175 | 0.2367 | C36 | 0.6330 | 0.7057 | 0.3036 |
| N7 | 0.7782 | 0.8435 | 0.1022 | C37 | 0.6344 | 0.7130 | 0.3479 |
| N8 | 1.2577 | 0.8656 | 0.3327 | C38 | 0.7356 | 0.7249 | 0.3704 |
| C1 | 0.1320 | 0.4944 | 0.0589 | C39 | 0.8318 | 0.7371 | 0.3469 |
| C2 | 0.1908 | 0.6351 | 0.0924 | C40 | 0.8351 | 0.7360 | 0.3037 |
| C3 | 0.3859 | 0.6317 | 0.0891 | C41 | 0.9911 | 0.8118 | 0.1926 |
| C4 | 0.3433 | 0.5481 | 0.0718 | C42 | 1.0032 | 0.8945 | 0.2105 |
| C5 | 0.3956 | 0.5243 | 0.0272 | C43 | 1.0770 | 0.9051 | 0.2475 |
| C6 | 0.5102 | 0.4539 | 0.0834 | C44 | 1.1352 | 0.8344 | 0.2626 |
| C7 | 0.3894 | 0.4685 | 0.1005 | C45 | 1.1302 | 0.7547 | 0.2437 |
| C8 | 0.2959 | 0.7609 | 0.1246 | C46 | 1.0571 | 0.7438 | 0.2088 |
| C9 | 0.3621 | 0.7671 | 0.1605 | C47 | 1.2065 | 0.8468 | 0.3020 |
| C10 | 0.3655 | 0.8516 | 0.1809 | C48 | 0.6138 | 0.8906 | 0.0540 |
| C11 | 0.3015 | 0.9209 | 0.1667 | C49 | 0.4223 | 0.8813 | 0.0217 |
| C12 | 0.2367 | 0.9111 | 0.1314 | C50 | 0.4895 | 0.8210 | 0.0056 |
| C13 | 0.2282 | 0.8341 | 0.1093 | C51 | 0.6039 | 0.8235 | 0.0241 |
| C14 | 0.3760 | 0.4887 | 0.1481 | C52 | 0.4553 | 0.7560 | −0.0257 |
| C15 | 0.4710 | 0.5122 | 0.1741 | H71 | 0.3329 | 0.7191 | −0.0666 |
| C16 | 0.4538 | 0.5334 | 0.2153 | H31 | 0.4830 | 0.4050 | 0.0230 |

TABLE 17

Several Peaks (2θ values) from Powder X-Ray Diffraction Pattern (CuKα λ = 1.5418 Å)

| Form | | | | | | | |
|---|---|---|---|---|---|---|---|
| M.5-2 | 6.45 | 10.26 | 14.47 | 15.88 | 18.73 | 19.66 | — |
| E.5-2 | 6.44 | 10.16 | 14.30 | 15.90 | 18.45 | 19.38 | 28.68 |
| IPA.5-2 | 6.33 | 10.12 | 13.95 | 15.98 | 18.54 | 19.68 | 28.70 |
| AN.5.-2 | 6.47 | 10.26 | 14.33 | 15.89 | 18.66 | 19.43 | 28.12 |
| IPA.5-2 | 6.38 | 10.10 | 14.22 | 15.96 | 18.42 | 19.72 | 28.69 |
| NMP.5-2 | 6.27 | 10.01 | 14.0 | 16.0 | 18.8 | 19.4 | 28.7 |
| THF.5-2 | 6.35 | 10.09 | 14.13 | 15.86 | 18.41 | 19.71 | 28.55 |
| (R)-2BU.5-2 | 6.34 | 10.12 | 14.20 | 15.67 | 18.98 | 19.76 | 28.69 |
| (S)-2BU.5-2 | 6.28 | 10.01 | 14.05 | 16.0 | 18.93 | 19.53 | 28.64 |

Example 5

Crystalline Form of the Mono Isopropanol Solvate of 4-[(5S*,9R*)-3-(3,5-Dichlorophenyl)-1-methyl-2,4-dioxo-1,3,7-triazaspiro[4.4]non-9-yl]-benzonitrile To a 500 ml 2-necked flask equipped with a stirbar, a condenser, and nitrogen sweep, were added 20.0 g of Preparation 2, 7.68 glycine, and 2.48 g hexamethylenetetramine. Next, 100 ml N-methyl pyrrolidone and 50 mL toluene were added. The contents of the flask was heated to 145° C. and maintained at this temperature for approximately 6 hours. The reaction mixture was allowed to cool to room temperature and held for 21 hours. Next, the contents of the flask was heated to 50° C., followed by the addition of 6 mL ethylene diamine. Next, 100 mL of tetrahydrofuran was added and the reaction mixture was held at 50° C. for 1 hour. The reaction mixture was cooled to room temperature and held 16-24 hours. Next, 260 mL of brine solution (20 wt. %), was added to the flask. The aqueous phase was split from the organic phase with 370 mL of the aqueous phase isolated. Half of the organic phase (67 mL) was removed and 100 mL of MeOH was charged. Solids were filtered and washed with two portions of 12.5 mL MeOH. After drying overnight at 60° C. under vacuum, 7.2423 g of 4-[(5S*,9R*)-3-(3,5-Dichlorophenyl)-1-methyl-2,4-dioxo-1,3,7-triazaspiro[4.4]non-9-yl]-benzonitrile (freebase hydrate) was collected as a white solid (65% yield).

Approximately 10-15 ml of isopropyl alcohol was added to a vial. 4-[(5S*, 9R*)-3-(3,5-Dichlorophenyl)-1-methyl-2,4-dioxo-1,3,7-triazaspiro[4.4]non-9-yl]-benzonitrile (freebase hydrate) was added until a saturated solution was obtained. The saturated supernatant was filtered into a second vial and allow to stand for 4 days. A crystal formed and was removed with tweezers. The crystal was characterized by X-ray crystallography according to the procedure described in Example 4. The unit cell parameters for the resulting crystal, the crystalline form of the mono isopropanol solvate of 4-[(5S*,9R*)-3-(3,5-Dichlorophenyl)-1-methyl-2,4-dioxo-1,3,7-triazaspiro[4.4]non-9-yl]-benzonitrile, Form IPA-1, are listed in Tables 18a and 18b.

TABLE 18a

Unit Cell Parameters

| Form | a(Å) | b(Å) | c(Å) | α | β | γ | V(Å$^3$) | T(° C.) |
|---|---|---|---|---|---|---|---|---|
| IPA-1 | 9.93 | 10.76 | 12.80 | 111.7 | 89.8 | 107.6 | 1202.7 | −50 |

TABLE 18b

Unit Cell Parameters (continued)

| Form | Z | $V_m$ | SG | $D_{calc}$ (g/cm$^3$) | MP (° C.) |
|---|---|---|---|---|---|
| IPA-1 | 1 | 601 | P-1 | 1.313 | 90-99(t), 104(t), 152 |

TABLE 19

Positional Parameters for 4-[(5S*, 9R*)-3-(3,5-Dichlorophenyl)-1-methyl-2,4-dioxo-1,3,7-triazaspiro[4.4]non-9-yl]-benzonitrile from IPA-1 at −50° C.

| Atom | X | Y | Z | Atom | X | Y | Z |
|---|---|---|---|---|---|---|---|
| C112 | 0.74018 | 0.36282 | 1.01032 | C11 | 0.7056 | 0.5292 | 0.9056 |
| C114 | 0.24762 | 0.26610 | 0.77367 | C12 | 0.6402 | 0.4115 | 0.9298 |
| O2 | 0.7610 | 0.8581 | 0.9889 | C13 | 0.4996 | 0.3281 | 0.8902 |
| O4 | 0.6663 | 0.5628 | 0.6154 | C14 | 0.4252 | 0.3662 | 0.8239 |
| O99 | 1.0793 | 0.8420 | 0.3894 | C15 | 0.4846 | 0.4819 | 0.7966 |
| N1 | 0.8157 | 0.8981 | 0.8260 | C16 | 0.5303 | 0.8357 | 0.6825 |
| N3 | 0.6883 | 0.6803 | 0.8082 | C17 | 0.4231 | 0.7078 | 0.6225 |
| N7 | 0.8617 | 0.8537 | 0.5361 | C18 | 0.2907 | 0.6774 | 0.6609 |
| N23 | 0.0192 | 0.7213 | 0.8318 | C19 | 0.2651 | 0.7767 | 0.7577 |
| C2 | 0.7576 | 0.8202 | 0.8879 | C20 | 0.3685 | 0.9044 | 0.8163 |
| C4 | 0.7047 | 0.6699 | 0.7000 | C21 | 0.5008 | 0.9318 | 0.7780 |
| C5 | 0.7789 | 0.8181 | 0.7054 | C22 | 0.1274 | 0.7445 | 0.7990 |
| C6 | 0.9030 | 0.8217 | 0.6308 | C31 | 0.8998 | 1.0471 | 0.8788 |
| C8 | 0.7050 | 0.8140 | 0.5259 | C96 | 1.0790 | 0.6181 | 0.3759 |

TABLE 19-continued

Positional Parameters for 4-[(5S*, 9R*)-3-(3,5-Dichlorophenyl)-1-methyl-2,4-dioxo-1,3,7-triazaspiro[4.4]non-9-yl]-benzonitrile from IPA-1 at −50° C.

| Atom | X | Y | Z | Atom | X | Y | Z |
|---|---|---|---|---|---|---|---|
| C9 | 0.6793 | 0.8691 | 0.6499 | C97 | 1.2990 | 0.7898 | 0.3779 |
| C10 | 0.6247 | 0.5626 | 0.8382 | C98 | 1.1578 | 0.7550 | 0.4037 |

Example 6

Crystalline Forms of the Aminal Dimers of 4-[3-(3,5-Dichlorophenyl)-1-methyl-2,4-dioxo-1,3,7-triazaspiro[4.4]non-9-yl]-benzonitrile

Example 6a

Isolation of Meso Aminal Dimer of 4-[3-(3,5-Dichlorophenyl)-1-methyl-2,4-dioxo-1,3,7-triazaspiro[4.4]non-9-yl]-benzonitrile (Compound IVb)

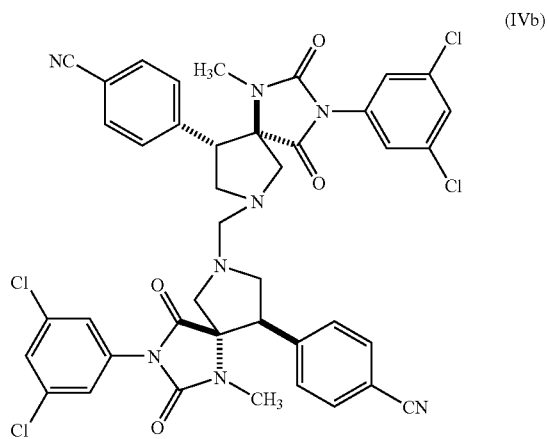

(IVb)

To a 500 ml 2-necked flask equipped with a stirbar, a condenser, and nitrogen sweep, was added 19.99 g Preparation 2, 7.68 glycine, and 2.48 g hexamethylenetetramine. Next, 100 ml N-methyl pyrrolidone and 50 mL toluene were added. The contents of the flask was heated to 145° C. and maintained at this temperature for approximately 6 hours. The reaction mixture was allowed to cool to room temperature and remained at room temperature for 3 days. Distillation of the reaction mixture was started at a pressure of 50 torr and heated until distillate was remove (pot temperature was approximately 100° C.). Testing of the sample showed that the reaction was approximately 70% complete. Next, 35 mL of the distillate was recharged to the flask and heated to 145° C. for 2 hours. The contents of the flask was distilled at 50 torr until the pot temperature reached 109° C. Approximately 25 mL of distillate was collected. The contents of the flask was allowed to cool to 50° C., followed by the addition of 5 mL ethylene diamine. The contents of the flask were maintained at a temperature of 50° C. for 145 minutes. Next, 260 mL of brine solution (14 wt. %), 100 mL tetrahydrofuran, and 100 mL MTBE were added to the flask. The aqueous phase was split from the organic phase with 373 mL of the aqueous phase isolated. Material precipitated from the organic phase. The organic phase was heated to 45° C. and 100 mL of tetrahydrofuran was added. The contents of the flask was distilled and 230 mL of distillate was collected. The remaining contents of the flask was allowed to cool to room temperature followed by the addition of 200 mL methanol and then redistilled. After the addition of 120 mL methylene chloride, the contents of the flask was heated to 20° C. Next, 150 mL methylene chloride was added. The resulting solution was polish filtered and the filter was washed with 10 mL methylene chloride. To the filtrate was added 3.5339 g (+)-DTTA, followed by stirring for 10 minutes and the addition of 247.2 mg of seed crystals of Example 2a. The filtrate was filtered and washed twice with a mixture of $CH_2Cl_2$:MTBE (1:3). A minute amount of crystals were observed to precipitate from the wash after 2 to 3 weeks in a closed container. Crystals were isolated with tweezers.

Example 6b

Isolation of Racemic Aminal Dimer of 4-[3-(3,5-Dichlorophenyl)-1-methyl-2,4-dioxo-1,3,7-triazaspiro[4.4]non-9-yl]-benzonitrile (Compound IVb)

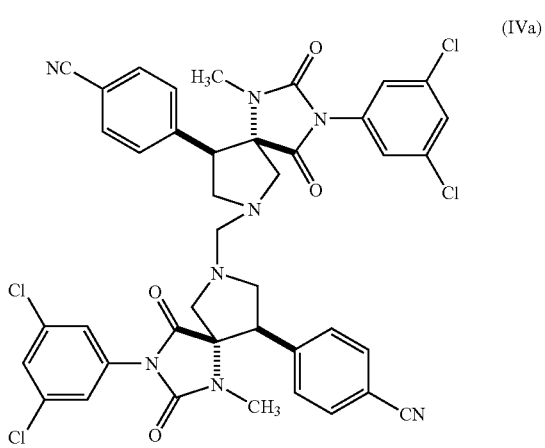

(IVa)

To a 250 ml 3-necked flask equipped with a stirbar was added 10.0 g 4-[(5S*, 9R*)-3-(3,5-Dichlorophenyl)-1-methyl-2,4-dioxo-1,3,7-triazaspiro[4.4]non-9-yl]-benzonitrile (freebase) and 2.65 g hexamethylenetetramine. Next, 20 mL N-methyl pyrrolidone and 25 mL toluene were added. The contents of the flask was distilled and then 25 mL toluene was added to the flask. The contents of the flask was maintained at a temperature of 145° C. for 4 hours. To the flask was added 260 ml of a 20 wt % brine solution and 100 mL tetrahydrofuran. The phases were split and the organic phase was dried over $Mg_2SO_4$. The organic phase was then filtered and concentrated on a rotovap. Next, 50 mL methylene chloride was added to the organic phase followed by the slow addition of 75 mL MTBE until the solution turned cloudy. The resulting precipitate was filtered from solution. A sample of the precipitate was dissolved in a minimum volume of warm MeCN/MeOH and allowed to cool slowly to ambient temperature. Crystals appeared as the solvents were evaporated from the sample solution.

TABLE 20a

Unit Cell Parameters

| Form | a(Å) | b(Å) | c(Å) | α | β | γ | V(Å³) | T(° C.) |
|---|---|---|---|---|---|---|---|---|
| MTBE2-1 | 10.22 | 11.51 | 22.23 | 85.4 | 86.0 | 87.6 | 2597.7 | −50 |
| AN1.5-1 | 13.33 | 17.95 | 19.13 | 85.2 | 83.3 | 83.1 | 4477.8 | −50 |

TABLE 20b

Unit Cell Parameters (continued)

| Form | Z | $V_m$ | SG | $D_{calc}$ (g/cm³) | MP (° C.) |
|---|---|---|---|---|---|
| MTBE2-1 | 1 | 1299 | P-1 | 1.305 | 79-109(t), 137-150 |
| AN1.5-1 | 2 | 1119 | P-1 | 1.341 | 31-47(t), 196-202 |

TABLE 21

Positional Parameters for the Aminal Dimer of 4-[3-(3,5-Dichlorophenyl)-1-methyl-2,4-dioxo-1,3,7-triazaspiro[4.4]non-9-yl]-benzonitrile form MTBE2-1 at −50 C.

| Atom | X | Y | Z | Atom | X | Y | Z |
|---|---|---|---|---|---|---|---|
| CL12 | 0.8896 | 0.1274 | 0.3754 | C21 | 0.6820 | 0.4479 | 0.5190 |
| CL14 | 1.3218 | 0.0124 | 0.4933 | C22 | 0.516 | 0.3049 | 0.4018 |
| CL42 | 0.6286 | 1.1408 | 0.9361 | C24 | 0.938 | 0.565 | 0.6427 |
| CL44 | 0.1065 | 1.1361 | 0.9720 | C30 | 0.6250 | 0.3808 | 0.7973 |
| O2 | 1.0935 | 0.4399 | 0.5537 | C32 | 0.290 | 0.8040 | 0.8190 |
| O4 | 0.7971 | 0.1673 | 0.6271 | C34 | 0.4379 | 0.7152 | 0.8826 |
| O32 | 0.2150 | 0.8778 | 0.7966 | C35 | 0.4025 | 0.6255 | 0.8399 |
| O34 | 0.5143 | 0.6984 | 0.9223 | C36 | 0.5235 | 0.5764 | 0.8053 |

TABLE 21-continued

Positional Parameters for the Aminal Dimer of 4-[3-(3,5-Dichlorophenyl)-1-methyl-2,4-dioxo-1,3,7-triazaspiro[4.4]non-9-yl]-benzonitrile form MTBE2-1 at −50 C.

| Atom | X | Y | Z | Atom | X | Y | Z |
|---|---|---|---|---|---|---|---|
| O89 | 0.693 | 0.841 | 0.8115 | C38 | 0.4485 | 0.4205 | 0.8707 |
| O99 | 0.323 | 0.1778 | 0.6723 | C39 | 0.3376 | 0.5152 | 0.8744 |
| N1 | 0.9196 | 0.4464 | 0.6253 | C40 | 0.369 | 0.9206 | 0.8963 |
| N3 | 0.9568 | 0.2856 | 0.5774 | C41 | 0.485 | 0.9676 | 0.9014 |
| N7 | 0.6766 | 0.4152 | 0.7347 | C42 | 0.483 | 1.074 | 0.9300 |
| N23 | 0.484 | 0.288 | 0.3551 | C43 | 0.362 | 1.123 | 0.9525 |
| N31 | 0.3104 | 0.6931 | 0.8026 | C44 | 0.255 | 1.071 | 0.9456 |
| N33 | 0.3668 | 0.8161 | 0.8677 | C45 | 0.252 | 0.971 | 0.9191 |
| N37 | 0.5061 | 0.4501 | 0.8094 | C46 | 0.2710 | 0.5325 | 0.9363 |
| N53 | 0.007 | 0.585 | 1.1502 | C47 | 0.159 | 0.6062 | 0.9399 |
| C2 | 0.9998 | 0.3973 | 0.5824 | C48 | 0.090 | 0.622 | 0.9950 |
| C4 | 0.8496 | 0.2580 | 0.6186 | C49 | 0.135 | 0.5648 | 1.0467 |
| C5 | 0.8135 | 0.3710 | 0.6489 | C50 | 0.245 | 0.491 | 1.0445 |
| C6 | 0.7997 | 0.3504 | 0.7183 | C51 | 0.3138 | 0.4747 | 0.9888 |
| C8 | 0.5891 | 0.3909 | 0.6892 | C52 | 0.063 | 0.577 | 1.1045 |
| C9 | 0.6743 | 0.4223 | 0.6313 | C54 | 0.249 | 0.650 | 0.7528 |
| C10 | 1.0070 | 0.2135 | 0.5302 | C84 | 0.840 | 0.783 | 0.743 |
| C11 | 1.1279 | 0.1588 | 0.5343 | C85 | 0.870 | 0.970 | 0.779 |
| C12 | 1.1728 | 0.0888 | 0.4886 | C86 | 0.858 | 0.807 | 0.866 |
| C13 | 1.103 | 0.0781 | 0.4394 | C87 | 0.819 | 0.857 | 0.795 |
| C14 | 0.982 | 0.1368 | 0.4360 | C88 | 0.616 | 0.916 | 0.749 |
| C15 | 0.935 | 0.2065 | 0.4823 | C94 | 0.210 | 0.341 | 0.7033 |
| C16 | 0.6301 | 0.3871 | 0.5727 | C95 | 0.300 | 0.207 | 0.7817 |
| C17 | 0.539 | 0.3007 | 0.5686 | C96 | 0.103 | 0.153 | 0.7223 |
| C18 | 0.503 | 0.2726 | 0.5129 | C97 | 0.232 | 0.214 | 0.7233 |
| C19 | 0.5576 | 0.3325 | 0.4597 | C98 | 0.386 | 0.044 | 0.6663 |
| C20 | 0.6461 | 0.4187 | 0.4633 | — | — | — | — |

TABLE 22

Positional Parameters for the Aminal Dimer of 4-[3-(3,5-Dichlorophenyl)-1-methyl-2,4-dioxo-1,3,7-triazaspiro[4.4]non-9-yl]-benzonitrile form AN1.5-1 at −50 C.

| Atom | X | Y | Z | Atom | X | Y | Z |
|---|---|---|---|---|---|---|---|
| Cl1 | 0.90486 | −0.45750 | 0.30051 | O6 | 0.7959 | 0.36735 | 0.36824 |
| Cl2 | 1.02030 | −0.36501 | 0.52958 | O7 | 0.1270 | 0.5817 | 0.0962 |
| Cl3 | −0.16561 | 0.25028 | 0.14891 | O8 | 0.3718 | 0.7263 | 0.1293 |
| Cl4 | 0.12168 | 0.34831 | −0.05307 | N9 | 0.5432 | 0.3293 | 0.40123 |
| O1 | 0.5825 | −0.30346 | 0.42138 | N10 | 0.6980 | 0.26901 | 0.40258 |
| O2 | 0.8062 | −0.12437 | 0.38013 | N11 | 0.5632 | 0.50863 | 0.31704 |
| O3 | 0.1059 | 0.0102 | 0.1133 | N12 | 0.8469 | 0.3775 | 0.729 |
| O4 | 0.3134 | 0.1845 | 0.14565 | N13 | 0.5225 | 0.5480 | 0.2003 |
| N1 | 0.5577 | −0.1735 | 0.39980 | N14 | 0.2865 | 0.5496 | 0.1340 |
| N2 | 0.7159 | −0.22816 | 0.40650 | N15 | 0.2359 | 0.6714 | 0.1038 |
| N3 | 0.5534 | 0.00202 | 0.31947 | N16 | 0.4192 | 0.7445 | −0.2501 |
| N4 | 0.8651 | −0.0821 | 0.7207 | C42 | 0.4342 | 0.3419 | 0.3988 |
| N5 | 0.5034 | 0.0311 | 0.20417 | C43 | 0.5933 | 0.2594 | 0.4125 |
| N6 | 0.2695 | −0.0025 | 0.14658 | C44 | 0.7146 | 0.3431 | 0.382 |
| N7 | 0.1938 | 0.1131 | 0.11994 | C45 | 0.6108 | 0.3885 | 0.3803 |
| N8 | 0.3404 | 0.2292 | −0.2319 | C46 | 0.5994 | 0.4315 | 0.3059 |
| C1 | 0.4502 | −0.1655 | 0.3910 | C47 | 0.6120 | 0.5225 | 0.3768 |
| C2 | 0.6127 | −0.2417 | 0.4102 | C48 | 0.5938 | 0.4526 | 0.4294 |
| C3 | 0.7275 | −0.1527 | 0.3891 | C49 | 0.7769 | 0.2065 | 0.4013 |
| C4 | 0.6221 | −0.1113 | 0.3828 | C50 | 0.7853 | 0.1623 | 0.3472 |
| C5 | 0.6135 | −0.0687 | 0.3077 | C51 | 0.8619 | 0.1033 | 0.3459 |
| C6 | 0.5937 | 0.0247 | 0.3801 | C52 | 0.9288 | 0.0878 | 0.3971 |
| C7 | 0.5925 | −0.0478 | 0.4321 | C53 | 0.9188 | 0.1342 | 0.4496 |
| C8 | 0.7973 | −0.2880 | 0.4101 | C54 | 0.8429 | 0.1935 | 0.4533 |
| C9 | 0.8100 | −0.3367 | 0.3592 | C55 | 0.6515 | 0.4393 | 0.4944 |
| C10 | 0.8882 | −0.3947 | 0.3632 | C56 | 0.7147 | 0.4893 | 0.5097 |
| C11 | 0.9521 | −0.4049 | 0.4158 | C57 | 0.7642 | 0.4756 | 0.5698 |
| C12 | 0.9378 | −0.3545 | 0.4646 | C58 | 0.7536 | 0.4101 | 0.6158 |
| C13 | 0.8600 | −0.2956 | 0.4628 | C59 | 0.6895 | 0.3590 | 0.6021 |
| C14 | 0.6513 | −0.0530 | 0.4952 | C60 | 0.6380 | 0.3747 | 0.5428 |

TABLE 22-continued

Positional Parameters for the Aminal Dimer of 4-[3-(3,5-Dichlorophenyl)-1-methyl-2,
4-dioxo-1,3,7-triazaspiro[4.4]non-9-yl]-benzonitrile form AN1.5-1 at −50 C.

| Atom | X | Y | Z | Atom | X | Y | Z |
|------|---|---|---|------|---|---|---|
| C15 | 0.7064 | 0.0048 | 0.5067 | C61 | 0.8067 | 0.3940 | 0.6794 |
| C16 | 0.7605 | −0.0010 | 0.5640 | C62 | 0.5836 | 0.5616 | 0.2538 |
| C17 | 0.7618 | −0.0673 | 0.6128 | C63 | 0.5541 | 0.5825 | 0.1284 |
| C18 | 0.7072 | −0.1260 | 0.6022 | C64 | 0.4682 | 0.5687 | 0.0886 |
| C19 | 0.6528 | −0.1187 | 0.5442 | C65 | 0.3730 | 0.5887 | 0.1415 |
| C20 | 0.8195 | −0.0746 | 0.6720 | C66 | 0.4147 | 0.5741 | 0.2142 |
| C21 | 0.5575 | 0.0569 | 0.2560 | C67 | 0.2817 | 0.4691 | 0.1498 |
| C22 | 0.5185 | 0.0718 | 0.1336 | C68 | 0.2073 | 0.5982 | 0.1103 |
| C23 | 0.4390 | 0.0434 | 0.0962 | C69 | 0.3294 | 0.6712 | 0.1254 |
| C24 | 0.3450 | 0.0480 | 0.1530 | C70 | 0.1699 | 0.7384 | 0.0841 |
| C25 | 0.3928 | 0.0361 | 0.2229 | C71 | 0.0777 | 0.7494 | 0.1221 |
| C26 | 0.2865 | −0.0841 | 0.1534 | C72 | 0.0149 | 0.8151 | 0.1030 |
| C27 | 0.1814 | 0.0358 | 0.1258 | C73 | 0.0435 | 0.8677 | 0.0478 |
| C28 | 0.2838 | 0.1248 | 0.1401 | C74 | 0.1378 | 0.8551 | 0.0116 |
| C29 | 0.1196 | 0.1735 | 0.0961 | C75 | 0.2024 | 0.7904 | 0.0285 |
| C30 | 0.0234 | 0.1792 | 0.1297 | C76 | 0.4620 | 0.6068 | 0.0140 |
| C31 | −0.0444 | 0.2400 | 0.1057 | C77 | 0.3882 | 0.5902 | −0.0263 |
| C32 | −0.0160 | 0.2916 | 0.0492 | C78 | 0.3787 | 0.6254 | −0.0944 |
| C33 | 0.0817 | 0.2834 | 0.0171 | C79 | 0.4452 | 0.6763 | −0.1249 |
| C34 | 0.1513 | 0.2241 | 0.0396 | C80 | 0.5219 | 0.6916 | −0.0873 |
| C35 | 0.4184 | 0.0829 | 0.0235 | C81 | 0.5300 | 0.6566 | −0.0181 |
| C36 | 0.3508 | 0.0565 | −0.0149 | C82 | 0.4330 | 0.7148 | −0.1949 |
| C37 | 0.3294 | 0.0929 | −0.0814 | N17 | 0.2144 | 0.8365 | 0.3465 |
| C38 | 0.3779 | 0.1559 | −0.1107 | C83 | 0.0465 | 0.8439 | 0.2973 |
| C39 | 0.4474 | 0.1806 | −0.0744 | C84 | 0.1425 | 0.8398 | 0.3261 |
| C40 | 0.4682 | 0.1442 | −0.0079 | N18 | −0.1930 | 0.4729 | 0.1179 |
| C41 | 0.3567 | 0.1959 | −0.1781 | C85 | −0.0171 | 0.4544 | 0.1409 |
| Cl5 | 10.87458 | 0.04737 | 0.27732 | C86 | −0.1168 | 0.4516 | 0.1261 |
| Cl6 | 11.00576 | 0.11801 | 0.51280 | N19 | 0.1983 | 0.3389 | 0.3154 |
| Cl7 | 10.10232 | 0.83017 | 0.15200 | C87 | 0.0395 | 0.2857 | 0.2979 |
| Cl8 | 10.17612 | 0.92111 | −0.05765 | C88 | 0.1290 | 0.3166 | 0.3081 |
| O5 | 0.5593 | 0.19977 | 0.42894 | — | — | — | — |

TABLE 23

Several Peaks (2θ values) from Powder X-Ray Diffraction Pattern
(CuKα λ = 1.5418 Å) at T = −50° C.

| MTBE2-1 | AN1.5-1 |
|---------|---------|
| 8.0 | 5.0 |
| 9.8 | 9.4 |
| 11.4 | 11.4 |
| 16.3 | 12.1 |
| 17.3 | 18.8 |
| 20.0 | 21.2 |
| 23.5 | 22.3 |
| — | 26.8 |

What is claimed is:

1. A process for preparing a spiro-hydantoin compound (II) of formula

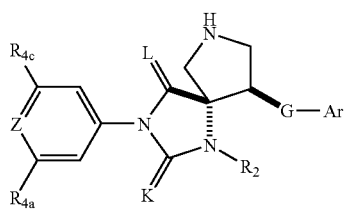

(II)

comprising: contacting alkene compound (I) of formula:

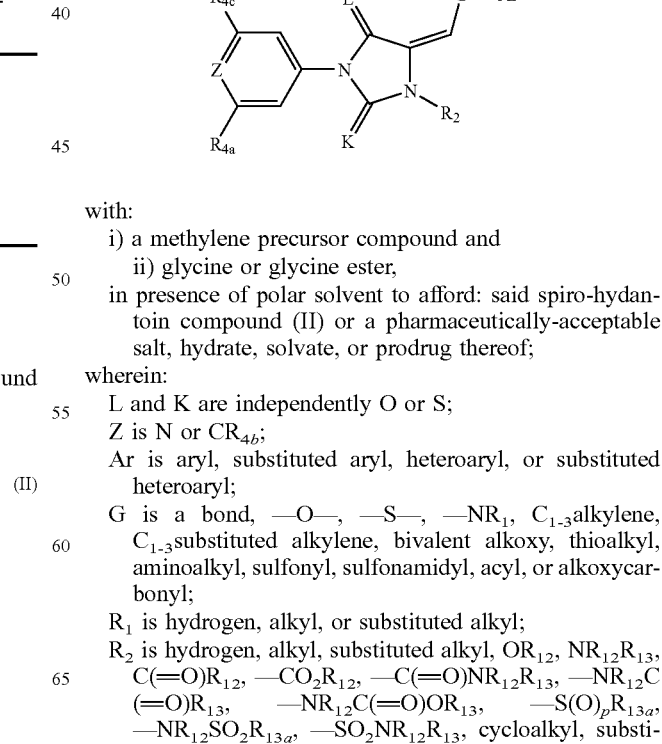

(I)

with:
i) a methylene precursor compound and
ii) glycine or glycine ester,
in presence of polar solvent to afford: said spiro-hydantoin compound (II) or a pharmaceutically-acceptable salt, hydrate, solvate, or prodrug thereof;

wherein:
L and K are independently O or S;
Z is N or $CR_{4b}$;
Ar is aryl, substituted aryl, heteroaryl, or substituted heteroaryl;
G is a bond, —O—, —S—, —$NR_1$, $C_{1-3}$alkylene, $C_{1-3}$substituted alkylene, bivalent alkoxy, thioalkyl, aminoalkyl, sulfonyl, sulfonamidyl, acyl, or alkoxycarbonyl;
$R_1$ is hydrogen, alkyl, or substituted alkyl;
$R_2$ is hydrogen, alkyl, substituted alkyl, $OR_{12}$, $NR_{12}R_{13}$, C(=O)$R_{12}$, —$CO_2R_{12}$, —C(=O)$NR_{12}R_{13}$, —$NR_{12}$C(=O)$R_{13}$, —$NR_{12}$C(=O)$OR_{13}$, —S(O)$_pR_{13a}$, —$NR_{12}SO_2R_{13a}$, —$SO_2NR_{12}R_{13}$, cycloalkyl, substituted cycloalkyl, heterocyclo, substituted heterocyclo, aryl, substituted aryl, heteroaryl, or substituted heteroaryl;

$R_{4a}$, $R_{4b}$, and $R_{4c}$ are independently hydrogen, halogen, alkyl, substituted alkyl, alkenyl, substituted alkenyl, nitro, cyano, —$SR_{14}$, —$OR_{14}$, —$NR_{14}R_{15}$, —$NR_{14}C(=O)R_{15}$, —$CO_2R_{14}$, —$C(=O)R_{14}$, —$C(=O)NR_{14}R_{15}$, aryl, substituted aryl, heterocyclo, substituted heterocyclo, cycloalkyl, substituted cycloalkyl heteroaryl, and/or substituted heteroaryl;

$R_{12}$, $R_{13}$, $R_{14}$, and $R_{15}$ are independently hydrogen, alkyl, substituted alkyl, cycloalkyl, substituted cycloalkyl, aryl, substituted aryl, heteroaryl, substituted heteroaryl, heterocyclo, and/or substituted heterocyclo; or (ii) $R_{12}$ is taken together with $R_{13}$, and/or $R_{14}$ is taken together with $R_{15}$ to form a heteroaryl, substituted heteroaryl, heterocyclo, or substituted heterocyclo ring;

$R_{13a}$ is alkyl, substituted alkyl, cycloalkyl, substituted cycloalkyl, aryl, substituted aryl, heteroaryl, substituted heteroaryl, heterocyclo, or substituted heterocyclo; and p is 1 or 2.

2. The process according to claim 1 wherein said methylene precursor compound is formaldehyde, hexamethylenetriamine, dimethoxymethane, trioxane, paraformaldehyde, or a mixture thereof.

3. The process according to claim 1 wherein said methylene precursor compound and said glycine or glycine ester are provided as condensation product of said methylene precursor and said glycine or glycine ester.

4. The process according to claim 1 wherein said polar solvent is 1-methyl-2-pyrrolidinone, dimethylacetamide, dimethylformamide, or a mixture thereof.

5. The process according to claim 1 conducted in a reaction mixture comprising said polar solvent and nonpolar solvent.

6. The process according to claim 1 further affording aminal of said spiro-hydantoin compound (II)

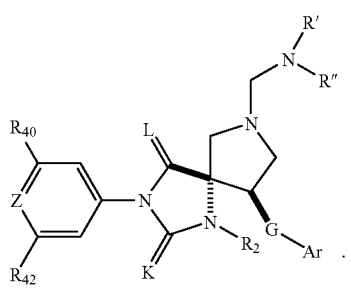
(II')

7. The process according to claim 6 further comprising the step of cleaving said aminal of said spiro-hydantoin compound (II) to afford said spiro-hydantoin compound (II).

8. The process according to claim 7 wherein said aminal of said spiro-hydantoin compound (II) is cleaved by contacting with aqueous acid, bisulfite salt, ethylene diamine, or propylene diamine.

9. The process according to claim 1 further comprising the step of: resolving said spiro-hydantoin compound (II) to provide at least one separated enantiomer.

10. The process according to claim 9 wherein said at least one separated enantiomer is resolved by crystallizing with an enantiomeric acid.

11. The process according to claim 10 wherein said at least one separated enantiomer is resolved in the presence of alcohol, water, or a combination thereof.

12. The process according to claim 10 wherein said enantiomeric acid is di-toluoyl-tartaric acid.

13. The process according to claim 1 wherein:
Z is $CR_{4b}$;
K is O; and
L is O.

14. The process according to claim 13 wherein:
G is a bond, $C_{1-3}$alkylene, or $C_{1-3}$substituted alkylene;
Ar is aryl or substituted aryl; and
$R_2$ is alkyl or substituted alkyl.

15. The process according to claim 14 wherein said spiro-hydantoin compound (II) has the formula

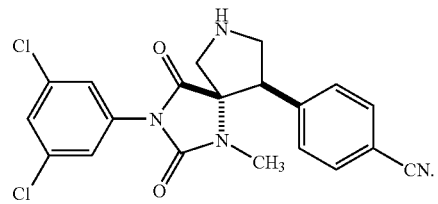

16. The process according to claim 15 wherein said spiro-hydantoin compound (II) is a spiro-hydantoin compound of formula IId:

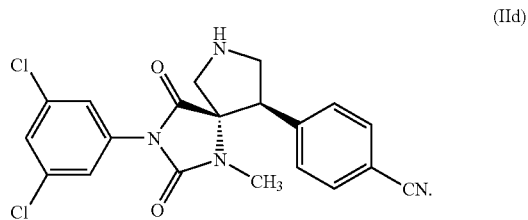
(IId)

17. The process according to claim 1 further comprising the step of: contacting said spiro-hydantoin compound (II) with an aldehyde containing compound, $HC(O)-Q-A_2-R_{16}$ in the presence of a reducing agent, to afford a substituted spiro-hydantoin compound (IIIc) of formula:

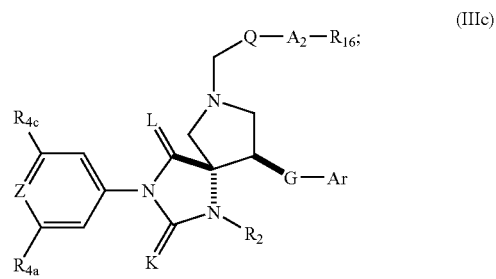
(IIIc)

wherein:
$A_2$ is a bond, $C_{1-3}$alkylene, $C_{2-3}$alkenylene, —$C_{1-4}$alkylene-$NR_{16}$—, —$C_{1-4}$alkylene-$NR_{16}C(=O)$—, —$C_{1-4}$alkylene-S—, —$C_{1-4}$alkylene-$SO_2$—, or —$C_{1-4}$alkylene-O—, wherein the $A_2$ alkylene groups are branched or straight chain, and, optionally, substituted alkylene;

Q is a bond, —$C(=O)$—, —$C(=O)NR_{16}$—, —$C(=S)NR_{16}$—, —$SO_2$—, —$SO_2NR_{16}$—, —$CO_2$—, or —$NR_{16}CO_2$—;

$R_{16}$ is hydrogen, alkyl, substituted alkyl, alkenyl, substituted alkenyl, aryl, substituted aryl, heteroaryl, substituted heteroaryl, heterocyclo, substituted heterocyclo, cycloalkyl, or substituted cycloalkyl, provided that $R_{16}$ is not hydrogen when $A_2$ and Q are each bonds; and $R_2$ is alkyl or substituted alkyl.

18. The process according to claim 17 wherein:

Z is $CR_{4b}$;

K is O; and

L is O.

19. The process according to claim 18 wherein:

G is a bond, $C_{1-3}$alkylene, or $C_{1-3}$substituted alkylene;

Ar is aryl or substituted aryl; and $R_2$ is alkyl or substituted alkyl.

20. The process according to claim 19 wherein said substituted spiro-hydantoin compound (IIIc) is:

21. The process according to claim 19 wherein said substituted spiro-hydantoin compound (IIIc) is:

22. The process according to claim 1 further comprising the step of: contacting said spiro-hydantoin compound (II) with a halogen containing compound, $X-A_1-Q-A_2-R_{16}$, to afford a substituted spiro-hydantoin compound (III) of formula:

(III)

wherein:

$A_1$ is a bond, $C_{1-2}$alkylene, or $C_{2-3}$alkenylene;

$A_2$ is a bond, $C_{1-3}$alkylene, $C_{2-3}$alkenylene, —$C_{1-4}$alkylene-$NR_{16}$—, —$C_{1-4}$alkylene-$NR_{16}C(=O)$—, —$C_{1-4}$alkylene-S—, —$C_{1-4}$alkylene-$SO_2$—, or —$C_{1-4}$alkylene-O—, wherein the $A_2$ alkylene groups are branched or straight chain, and, optionally, substituted alkylene;

Q is a bond, —C(=O)—, —C(=O)$NR_{16}$—, —C(=S)$NR_{16}$—, —$SO_2$—, —$SO_2NR_{16}$—, —$CO_2$—, or —$NR_{16}CO_2$—;

$R_{16}$ is hydrogen, alkyl, substituted alkyl, aryl, substituted aryl, heteroaryl, substituted heteroaryl, heterocyclo, substituted heterocyclo, cycloalkyl, or substituted cycloalkyl, provided that $R_{16}$ is not hydrogen when $A_1$, $A_2$, and Q are each bonds;

$R_2$ is alkyl or substituted alkyl; and

X is a halogen.

23. The process according to claim 22 wherein:

Z is $CR_{4b}$;

K is O; and

L is O.

24. The process according to claim 23 wherein:

G is a bond, $C_{1-3}$alkylene, or $C_{1-3}$substituted alkylene;

Ar is aryl or substituted aryl; and $R_2$ is alkyl or substituted alkyl.

25. The process according to claim 24 wherein said substituted spiro-hydantoin compound (IIIc) is:

26. The process according to claim 24 wherein said substituted spiro-hydantoin compound (IIIc) has the formula IIIn:

(IIIn)

27. A process for the preparation of a substituted spiro-hydantoin compound (IIIn) of formula

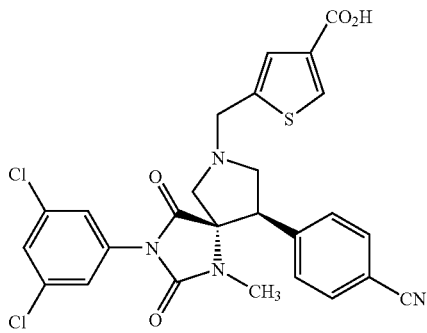

comprising:
a) contacting alkene compound (Ia) of formula

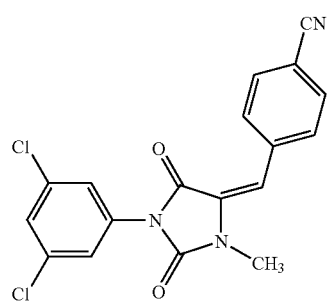

with:
i) a methylene precursor compound and
ii) glycine or glycine ester,
in presence of polar solvent to afford spiro-hydantoin compound (IIc) of formula

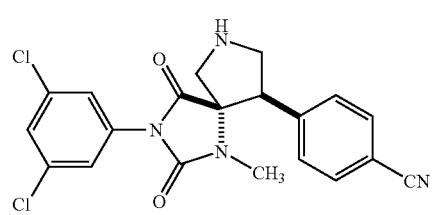

b) resolving enantiomers of said spiro-hydantoin compound (IIc) to afford spiro-hydantoin compound (IId) of formula

c) contacting said spiro-hydantoin compound (IId) with methyl 5-formylthiophene-3-carboxylate in the presence of a reducing agent to afford substituted spiro-hydantoin compound (IIIj) of formula

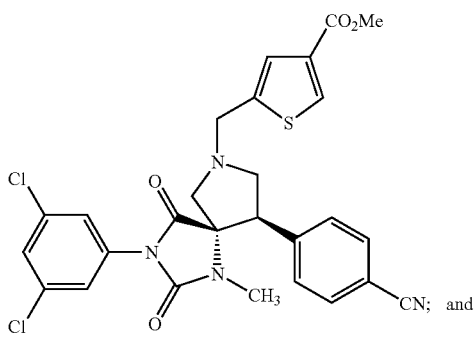

d) hydrolyzing methyl ester group of said substituted spiro-hydantoin compound (IIIj) to afford said substituted spiro-hydantoin compound (IIIn) or a pharmaceutically-acceptable salt, hydrate, solvate, or prodrug thereof.

28. The process according to claim 27, further affording aminal dimer of said spiro-hydantoin compound (IIc) selected from the group consisting of

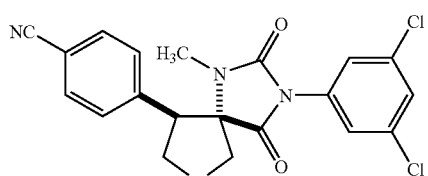

and

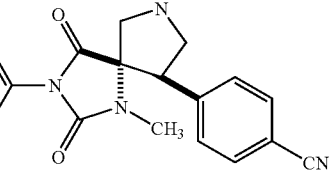

-continued

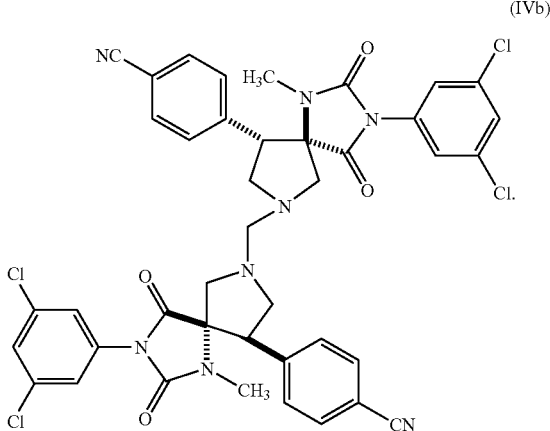

(IVb)

29. The process according to claim 28, further including the step of cleaving said aminal dimer of said spiro-hydantoin compound (IIc) to provide said spiro-hydantoin compound (IIc).

30. A crystalline Form N-1 of Compound (IIIn)

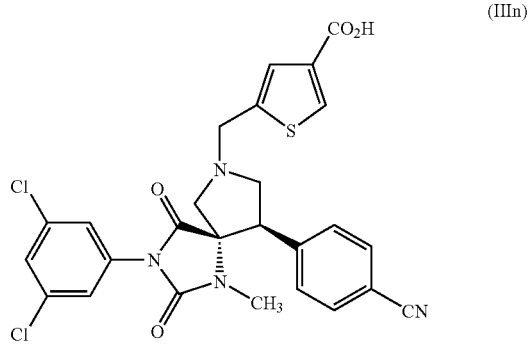

(IIIn)

consisting essentially of said Form N-1 characterized by unit cell parameters substantially equal to the following:

| Cell dimensions: | a = 12.07 Å |
| --- | --- |
|  | b = 17.76 Å |
|  | c = 13.12 Å |
|  | α = 90.0 degrees |
|  | β = 111.9 degrees |
|  | γ = 90.0 degrees |
| Space group | $P2_1$ |
| Molecules/unit cell | 2 | wherein said crystalline form is at a temperature of about +22° C.

31. The crystalline form according to claim 30, wherein said Form N-1 is in substantially pure form.

32. The crystalline form according to claim 30 characterized by a powder x-ray diffraction pattern comprising four or more 2θ values (CuKα λ=1.5418 Å) selected from 7.3, 8.5, 8.8, 13.1, 13.7, 15.4, and 17.0, at a temperature of about 22° C.

33. The crystalline form according to claim 32 further characterized by a powder x-ray diffraction pattern comprising five or more 2θ values (CuKα λ=1.5418 Å) selected from 7.3, 8.5, 8.8, 13.1, 13.7, 15.4, and 17.0, at a temperature of about 22° C.

34. The crystalline form according to claim 30 characterized by unit cell parameters substantially equal to the following:

| Cell dimensions: | a = 12.05 Å |
| --- | --- |
|  | b = 17.72 Å |
|  | c = 13.07 Å |
|  | α = 90.0 degrees |
|  | β = 112.0 degrees |
|  | γ = 90.0 degrees |
| Space group | $P2_1$ |
| Molecules/unit cell | 2 | wherein said crystalline form is at a temperature of about −50° C.

35. The crystalline form according to claim 30 characterized by a powder x-ray diffraction pattern comprising four or more 2θ values (CuKα λ=1.5418 Å) selected from 7.9, 8.5, 8.8, 13.1, 15.4, 17.0, and 17.1, at a temperature of about −50° C.

36. The crystalline form according to claim 35 further characterized by a powder x-ray diffraction pattern comprising five or more 2θ values (CuKα λ=1.5418 Å) selected from 7.9, 8.5, 8.8, 13.1, 15.4, 17.0, and 17.1, at a temperature of about −50° C.

37. A crystalline form of a methanesulfonic acid salt of

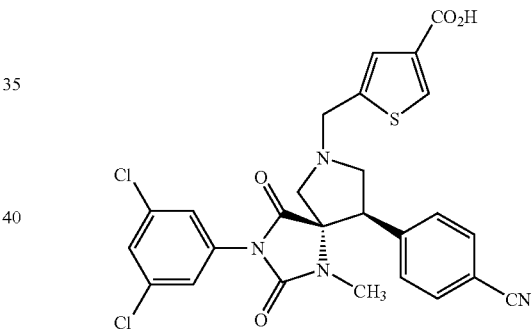

characterized by unit cell parameters substantially equal to the following:

| Cell dimensions: | a = 8.44 Å |
| --- | --- |
|  | b = 14.67 Å |
|  | c = 25.01 Å |
|  | α = 90.0 degrees |
|  | β = 97.1 degrees |
|  | γ = 90.0 degrees |
| Space group | $P2_1$ |
| Molecules/unit cell | 2 | wherein said crystalline form is at a temperature of about +22° C.

38. The crystalline form according to claim 37 characterized by a powder x-ray diffraction pattern comprising four or more 2θ values (CuKα λ=1.5418 Å) selected from 7.1, 9.3, 10.6, 14.1, 17.0, 21.1, 24.8, and 28.6, at a temperature of about 22° C.

39. The crystalline form according to claim 38 further characterized by a powder x-ray diffraction pattern comprising five or more 2θ values (CuKα λ=1.5418 Å) selected from 7.1, 9.3, 10.6, 14.1, 17.0, 21.1, 24.8, and 28.6, at a temperature of about 22° C.

40. A crystalline form of hydrochloric acid salt of

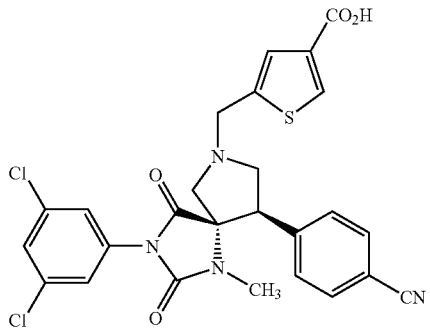

characterized by unit cell substantially equal to the following:

| Cell dimensions: | a = 8.26 Å |
| --- | --- |
| | b = 12.56 Å |
| | c = 13.22 Å |
| | α = 90.0 degrees |
| | β = 90.2 degrees |
| | γ = 90.0 degrees |
| Space group | $P2_1$ |
| Molecules/unit cell | 1 | wherein said crystalline form is at a temperature of about +22° C.

41. The crystalline form according to claim 40 characterized by a powder x-ray diffraction pattern comprising four or more 2θ values (CuKα λ=1.5418 Å) selected from 9.7, 12.8, 14.1, 14.5, 18.6, 19.0, 21.4, 23.8, and 26.7, at a temperature of about 22° C.

42. The crystalline form according to claim 41 further characterized by a powder x-ray diffraction pattern comprising five or more 2θ values (CuKα λ=1.5418 Å) selected from 9.7, 12.8, 14.1, 14.5, 18.6, 19.0, 21.4, 23.8, and 26.7, at a temperature of about 22° C.

43. A crystalline form of

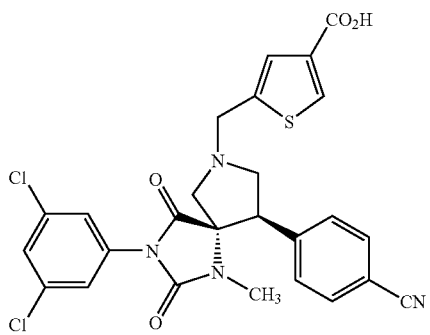

or zwitterion thereof, characterized by unit cell parameters substantially equal to the following:

Volume is in the range of about 5300 to 5800 Å³;
Space group $P2_12_12_1$;
Z=8;
and, optionally, comprising solvent.

44. The crystalline form according to claim 43 further comprising solvent.

45. The crystalline form according to claim 44 wherein said solvent is a polar solvent.

46. The crystalline form according to claim 44 wherein said solvent is a nonpolar solvent.

47. The crystalline form according to claim 44, wherein said solvent is methanol, ethanol, n-propanol, isopropanol, acetonitrile, N-methylpyrrolidinone, S-(+)-2-butanol, R-(−)-2-butanol, or tetrahydrofuran.

48. The crystalline form according to claim 44 comprising an asymmetric unit of 2 molecules of said compound or zwitterion thereof, and one molecule of said solvent.

49. The crystalline form according to claim 44 characterized by unit cell parameters substantially equal to the following:

Cell dimensions:
  a is in the range of from about 11.1 to about 11.4 Å;
  b is in the range of from about 14.9 to about 16.0 Å;
  c is in the range of from about 31.4 to about 32.8 Å;
  volume is in the range of from about 5300 to about 5800 Å³;
Space group $P2_12_12_1$
Molecules/unit cell 2
Density (calculated) (g/cm³) is in the range of from about 1.380 to about 1.420; wherein said crystalline form is at a temperature of about −50° C.

50. A pharmaceutical composition comprising at least one compound according to claim 30 and a pharmaceutically acceptable carrier or diluent.

51. A pharmaceutical composition comprising at least one compound according to claim 37, and a pharmaceutically acceptable carrier or diluent.

52. A pharmaceutical composition comprising at least one compound according to claim 40 and a pharmaceutically acceptable carrier or diluent.

53. A pharmaceutical composition comprising at least one compound according to claim 43 and a pharmaceutically acceptable carrier or diluent.

54. A crystalline IPA-1 form of Compound (IIc)

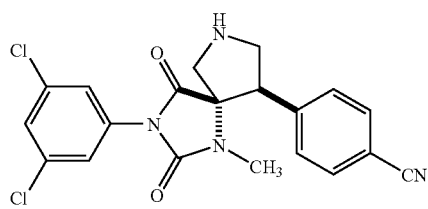

characterized by unit cell parameters substantially equal to the following:
  Cell dimensions: a=9.93 Å
    b=10.76 Å
    c=12.80 Å
    α=111.7 degrees
    β=89.8 degrees
    γ=107.6 degrees
  Space group P-1
  Molecules/unit cell I
wherein said crystalline form is at a temperature of about −50° C.

55. A crystalline form of Compound (IVa)

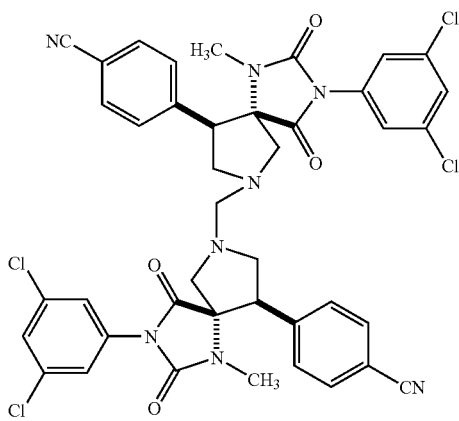

comprising Form AN1.5-1.

56. The crystalline form according to claim 55 characterized by unit cell parameters substantially equal to the following:

| Cell dimensions: | a = 13.33 Å |
| --- | --- |
| | b = 17.95 Å |
| | c = 19.13 Å |
| | α = 85.2 degrees |
| | β = 83.3 degrees |
| | γ = 83.1 degrees |
| Space group | P-1 |
| Molecules/unit cell | 2 | wherein said crystalline form is at a temperature of about −50° C.

57. The crystalline form according to claim 55 characterized by a powder x-ray diffraction pattern comprising four or more 2θ values (CuKα λ=1.5418 Å) selected from 5.0, 9.4, 11.4, 12.1, 18.8, 21.2, 22.3, and 26.8, at a temperature of about −50° C.

58. A crystalline form of Compound (IVb)

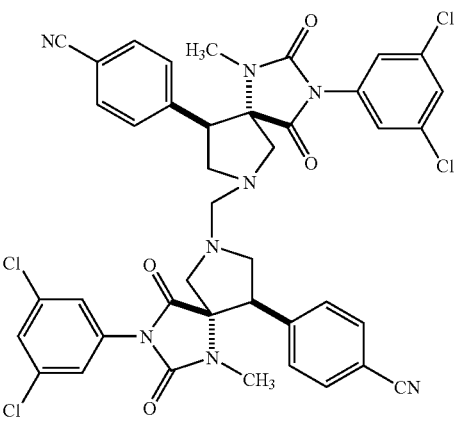

comprising Form MTBE2-1.

59. The crystalline form according to claim 58 characterized by unit cell parameters substantially equal to the following:

| Cell dimensions: | a = 10.22 Å |
| --- | --- |
| | b = 11.51 Å |
| | c = 22.23 Å |
| | α = 85.4 degrees |
| | β = 86.0 degrees |
| | γ = 87.6 degrees |
| Space group | P-1 |
| Molecules/unit cell | 1 | wherein said crystalline form is at a temperature of about −50° C.

60. The crystalline form according to claim 58 characterized by a powder x-ray diffraction pattern comprising four or more 2θ values (CuKα λ=1.5418 Å) selected from 8.0, 9.8, 11.4, 16.3, 17.3, 20.0, and 23.5, at a temperature of about −50° C.

* * * * *

UNITED STATES PATENT AND TRADEMARK OFFICE
CERTIFICATE OF CORRECTION

PATENT NO. : 7,381,737 B2 Page 1 of 2
APPLICATION NO. : 11/238427
DATED : June 3, 2008
INVENTOR(S) : Albert J. DelMonte et al.

It is certified that error appears in the above-identified patent and that said Letters Patent is hereby corrected as shown below:

In the Claims:

Claim 6:

Column 71, lines 40 to 50, change " 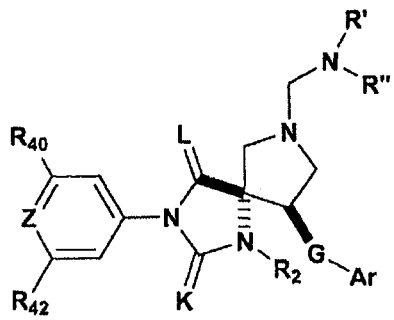 " to

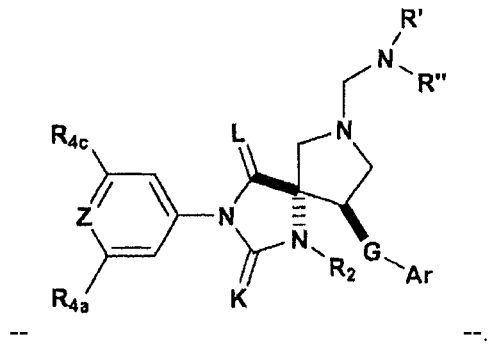

--    --.

Claim 54:

Column 80, line 65, change "I" to -- 1 --.

CERTIFICATE OF CORRECTION (continued)
U.S. Pat. No. 7,381,737 B2

Page 2 of 2

In the Claims:

Claim 58:

Column 82, lines 4 to 19, change " 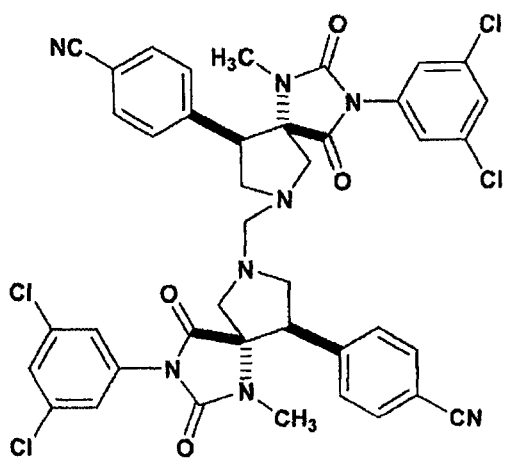 " to

-- 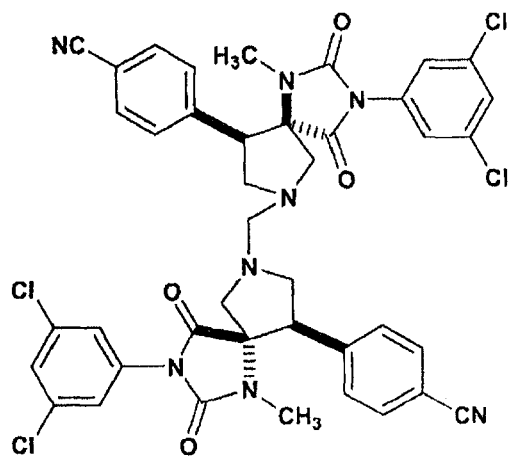 --.

Signed and Sealed this

Sixteenth Day of March, 2010

David J. Kappos
*Director of the United States Patent and Trademark Office*